United States Patent
Du Bois et al.

(10) Patent No.: US 6,977,265 B2
(45) Date of Patent: Dec. 20, 2005

(54) PIPERIDINE CCR-3 RECEPTOR ANTAGONISTS

(75) Inventors: Daisy Joe Du Bois, Palo Alto, CA (US); Denis John Kertesz, Mountain View, CA (US); Eric Brian Sjogren, Mountain View, CA (US); David Bernard Smith, San Mateo, CA (US); Beihan Wang, Santa Clara, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 72 days.

(21) Appl. No.: 10/307,130

(22) Filed: Nov. 29, 2002

(65) Prior Publication Data

US 2003/0229121 A1 Dec. 11, 2003

Related U.S. Application Data

(60) Provisional application No. 60/334,653, filed on Nov. 30, 2001, provisional application No. 60/334,819, filed on Nov. 30, 2001, and provisional application No. 60/334,655, filed on Nov. 30, 2001.

(51) Int. Cl.[7] .................... A61K 31/445; C07D 211/16
(52) U.S. Cl. ................ 514/331; 514/256; 514/300; 514/307; 514/311; 514/316; 514/326; 544/333; 546/122; 546/139; 546/152; 546/202; 546/205; 546/212
(58) Field of Search .................. 514/316, 326, 514/331, 256, 300, 307, 311; 546/187, 188, 208, 229, 233, 234, 122, 139, 152, 202, 205, 212; 544/333

(56) References Cited

U.S. PATENT DOCUMENTS 5,147,876 A * 9/1992 Mizuchi et al. ............. 514/275
6,331,541 B1 * 12/2001 Ko et al. .................. 514/237.2

FOREIGN PATENT DOCUMENTS

| WO | WO 00/35449 | 6/2000 |
|----|-------------|--------|
| WO | WO 00/35451 | 6/2000 |
| WO | WO 00/35452 | 6/2000 |
| WO | WO 00/35453 | 6/2000 |
| WO | WO 00/35454 | 6/2000 |
| WO | WO 01/87838 | * 11/2001 |

* cited by examiner

*Primary Examiner*—Celia Chang
(74) *Attorney, Agent, or Firm*—Grant D. Green

(57) ABSTRACT

The invention provides compounds of Formula (I):

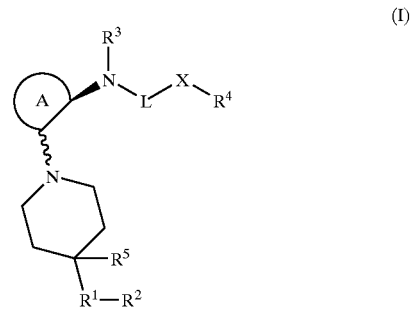

(I)

wherein: $R^1$–$R^5$, A, L, and X have any of the values defined in the specification that are CCR-3 receptor antagonists, pharmaceutical compositions containing them, methods for their use, and methods and intermediates useful for preparing them.

23 Claims, No Drawings

PIPERIDINE CCR-3 RECEPTOR ANTAGONISTS

This application claims the priority benefit under Title 35 U.S.C. 119(e) of U.S. Provisional application Ser. No. 60/334,653, filed Nov. 30, 2001, the disclosure of which is herein incorporated by reference.

This application also incorporates by reference U.S. Provisional application Ser. No. 60/334,819, filed Nov. 30, 2001, entitled "CCR-3 Receptor Antagonists (I)," and U.S. Provisional application Ser. No. 60/334,655, filed Nov. 11, 2001, entitled "Piperazine CCR-3 Receptor Antagonists," both filed concurrently on Nov. 30, 2001; and submitted as U.S. application Ser. No. 09/134,013 filed Aug. 14, 1998 issued U.S. Pat. No. 6,323,223, and U.S. application Ser. No. 09/247,905 filed Feb. 11, 1999 issued U.S. Pat. No. 6,116,015.

FIELD OF THE INVENTION

The invention relates to certain piperidine derivatives that are CCR-3 receptor antagonists, pharmaceutical compositions containing them, methods for their use, and methods and intermediates useful for preparing them.

BACKGROUND INFORMATION

Tissue eosinophilia is a feature of a number of pathological conditions such as asthma, rhinitis, eczema and parasitic infections (see Bousquet, J. et al., N. Eng. J. Med. 323: 1033–1039 (1990) and Kay, A. B. and Corrigan, C. J., Br. Med. Bull. 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils (see Baggiolini, M. and Dahinden, C. A., Immunol. Today. 15:127–133 (1994), Rot, A. M. et al., J. Exp. Med. 176, 1489–1495 (1992) and Ponath, P. D. et al., J. Clin. Invest., Vol. 97, #3, 604–612 (1996)). However, unlike RANTES and MCP-3 which also induce the migration of other leukocyte cell types, eotaxin is selectively chemotactic for eosinophils (see Griffith-Johnson, D. A. et al., Biochem. Biophy. Res. Commun. 197:1167 (1993) and Jose, P. J. et al., Biochem. Biophy. Res. Commun. 207, 788 (1994)). Specific eosinophil accumulation was observed at the site of administration of eotaxin whether by intradermal or intraperitoneal injection or aerosol inhalation (see Griffith-Johnson, D. A. et al., Biochem. Biophy. Res. Commun. 197:1167 (1993); Jose, P. J. et al., J. Exp. Med. 179, 881–887 (1994); Rothenberg, M. E. et al., J. Exp. Med. 181, 1211 (1995) and Ponath, P. D., J. Clin. Invest., Vol. 97, #3, 604–612 (1996)).

Glucocorticoids such as dexamethasone, methprednisolone and hydrocortisone have been used for treating many eosinophil-related disorders, including bronchial asthma (R. P. Schleimer et al., Am. Rev. Respir. Dis., 141, 559 (1990)). The glucocorticoids are believed to inhibit IL-5 and IL-3 mediated eosinophil survival in these diseases. However, prolonged use of glucocorticoids can lead to side effects such as glaucoma, osteoporosis and growth retardation in the patients (see Hanania, N. A. et al., J. Allergy and Clin. Immunol., Vol. 96, 571–579 (1995) and Saha, M. T. et al., Acta Paediatrica, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES and MCP-3. When transfected into a murine pre-beta. lymphoma line, CCR-3 bound eotaxin, RANTES and MCP-3 conferred chemotactic responses on these cells to eotaxin, RANTES and MCP-3 (see Ponath, P. D. et al., J. Exp. Med. 183, 2437–2448 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 (see Heath, H. et al., J. Clin. Invest., Vol. 99, #2, 178–184 (1997)). Applicants' issued U.S. patents U.S. Pat. Nos. 6,140,344 and 6,166,015 and published EP application EP903349, published Mar. 24, 1999 disclose CCR-3 antagonists that inhibit eosinophilic recruitment by chemokine such as eotaxin.

Therefore, blocking the ability of the CCR-3 receptor to bind RANTES, MCP-3 and eotaxin and thereby preventing the recruitment of eosinophils should provide for the treatment of eosinophil-mediated inflammatory diseases.

SUMMARY OF THE INVENTION

The present invention concerns novel piperidine derivatives which are capable of inhibiting the binding of eotaxin to the CCR-3 receptor and thereby provide a means of combating eosinophil induced diseases, such as asthma.

In a first aspect, this invention provides a compound of Formula (I):

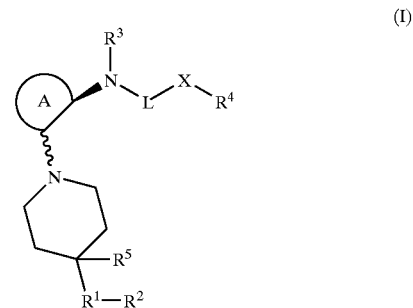

(I)

wherein:

$R^1$ is $(C_1-C_2)$alkylene;

$R^2$ is optionally substituted phenyl;

$R^3$ is hydrogen, alkyl, acyl, aryl, or arylalkyl;

ring A is a cycloalkyl, heterocyclyl, or optionally substituted phenyl;

L is —C(=O)—, —C(=S)—, —SO$_2$—, —C(=O)N(R$_a$)—, —C(=S) N(R$_a$)—, —SO$_2$N(R$_a$)—, —C(=O)O—, —C(=S)O—, —S(=O)$_2$O—;

where $R_a$ is hydrogen, alkyl, acyl, aryl, arylalkyl, alkoxycarbonyl, or benzyloxycarbonyl;

X is absent, —(CR'R")O—, —(CR'R")S—, —(CR'R")NR$_b$— or alkylene;

where R' and R" are independently hydrogen or alkyl, and $R_b$ is hydrogen or alkyl;

$R^4$ is aryl or heteroaryl; and $R^5$ is hydrogen or alkyl;

provided that when $R^1$ is —CH$_2$—, $R^2$ is phenyl, $R^3$ is hydrogen, $R^5$ is hydrogen, A is phenyl, L is —C(=O)NH— and X is absent, then $R^4$ is not 2,5-difluorophenyl; or prodrugs, individual isomers, ramecic and non-racemic mixtures of isomers, and pharmaceutically acceptable salts thereof.

In a second aspect, this invention provides pharmaceutical compositions containing a therapeutically effective amount of a compound of Formula (I) or a pharmaceutically acceptable salt thereof, and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or a pharmaceutically acceptable salt thereof. The disease states include respiratory diseases such as asthma.

In a fourth aspect, this invention provides processes disclosed herein for preparing compounds of Formula (I).

In a fifth aspect, this invention provides novel intermediates disclosed herein that are useful for preparing compounds of Formula (I).

In a sixth aspect, this invention provides a compound of Formula (I) or a pharmaceutically acceptable salt thereof for use in medical therapy or diagnosis (e.g. for treating asthma).

In a seventh aspect, this invention provides the use of a compound of Formula (I) or a pharmaceutically acceptable salt thereof for the manufacture of a medicament useful for treating a disease in a mammal treatable by administration of a CCR-3 receptor antagonist (e.g. asthma).

DETAILED DESCRIPTION OF THE INVENTION

Definitions

Unless otherwise stated, the following terms used in the specification and claims have the meanings given below.

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cyclohexylcarbonyl, cyclohexylmethylcarbonyl, benzoyl, benzylcarbonyl, and the like.

"Acylalkyl" means a radical -alkylene-C(O)R where R is hydrogen, alkyl, haloalkyl, cycloalkyl, cycloalkyl-alkyl, optionally substituted phenyl, benzyl, hydroxy, alkoxy, amino, monoalkylamino or dialkylamino. Representative examples include methylcarbonyl-methyl, 2-(ethoxycarbonyl)ethyl, 2-(methoxycarbonyl)ethyl, 2-carboxyethyl and the like.

"Acylamino" means a radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkoxy" means a radical —OR where R is an alkyl as defined herein e.g., methoxy, ethoxy, propoxy, butoxy and the like.

"Alkoxycarbonyl" means a radical —C(O)—R where R is alkoxy is as defined herein.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylamino" or "Monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylsulfonyl" means a radical —S(O)$_2$R where R is an alkyl, cycloalkyl or cycloalkyl-alkyl group as defined herein, e.g., methylsulfonyl, ethylsulfonyl, propylsulfonyl, butylsulfonyl, cyclohexylsulfonyl and the like.

"Alkylsulfinyl" means a radical —S(O)R where R is an alkyl, cycloalkyl or cycloalkylalkyl group as defined herein e.g., methylsulfinyl, ethylsulfinyl, propylsulfinyl, butylsulfinyl, cyclohexylsulfinyl and the like.

"Alkylthio" means a radical —SR where R is an alkyl as defined above e.g., methylthio, ethylthio, propylthio, butylthio, and the like.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

"Arylene" means a divalent aryl group as defined above.

"Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like.

"Aryloxy" means a radical —O—R where R is an aryl group as defined herein.

"Carbamoyl" means the radical —C(=O)NH$_2$.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkyl-alkyl" means a radical —R$^x$R$^y$ where R$^x$ is an alkylene group and R$^y$ is cycloalkyl group as defined herein, e.g., cyclohexylmethyl, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl) (methyl)amino, (cyclohexyl)(ethyl)amino, (cyclohexyl) (propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy, ethylenedioxy or optionally substituted phenyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, 5-(3,4-dimethoxyphenyl)-pyrimidin-2-yl, 5-(4-methoxyphenyl)-pyrimidin-2-yl, 5-(3,4-methylenedioxyphenyl)-pyrimidin-2-yl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl and derivatives thereof.

"Heteroarylene" means a divalent heteroaryl group as defined above.

"Heteroarylalkyl means an alkyl radical as defined herein in which one of the hydrogen atoms of the alkyl group is replaced with a heteroaryl group.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heterocyclyl" means a saturated or unsaturated non-aromatic cyclic radical of 3 to 8 ring atoms in which one or two ring atoms are heteroatoms selected from NR$^x$ {wherein each R$^x$ is independently hydrogen, alkyl, acyl, alkylsulfonyl, aminosulfonyl, (alkylamino)sulfonyl, (dialkylamino)sulfonyl, carbamoyl, (alkylamino)carbonyl, (dialkylamino)carbonyl, (carbamoyl)alkyl, (alkylamino)carbonylalkyl, or dialkylaminocarbonylalkyl}, O, or S(O)$_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy, alkoxy, amino, monoalkylamino, dialkylamino or optionally substituted phenyl, and R' is hydrogen or alkyl), -alkylene-C(O)R (where R is hydrogen, alkyl, haloalkyl, hydroxy, alkoxy, amino, monoalkylamino, dialkylamino or optionally substituted phenyl) or —S(O)$_n$R$^d$ (where n is an integer from 0 to 2, and R is hydrogen (provided that n is 0), alkyl, haloalkyl, cycloalkyl, cycloalkylalkyl, amino, monoalkylamino, dialkylamino, or hydroxyalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide,tetrahydrothiophenyl-S,S-dioxide, pyrrolinyl, imidazolinyl, and the derivatives thereof.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl group which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term includes, but is not limited to, phenyl, chlorophenyl, fluorophenyl, bromophenyl, methylphenyl, ethylphenyl, methoxyphenyl, cyanophenyl, 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-methylphenyl, 3-chloro-4-fluorophenyl or 3,4-dichlorophenyl and the derivatives thereof.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Phenylalkyl" refers to an alkyl radical as defined herein in which one of the hydrogen atoms of the alkyl radical has been replaced by an optionally substituted phenyl.

"Prodrugs" means any compound which releases an active parent drug according to Formula I in vivo when such a prodrug is administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The nomenclature used in this application is generally based on the IUPAC recommendations. For example, a compound of Formula (I) wherein $R_1$ is methylene; $R_2$ is 4-chlorophenyl; L is C(=O)NH; X is absent; A is cyclopentyl; $R_3$ is hydrogen; and $R_4$ is 2-quinolyl (Compound 1 in Table 1), is named (±)-trans-1-{2-[4-(4-chlorobenzyl) piperidin-1-yl]cyclopentyl}-3-quinolin-2-yl-urea Representative compounds of Formula (I) are shown in the following table.

TABLE I

| Compound | Structure | M.P. (° C.) |
|---|---|---|
| 1 | 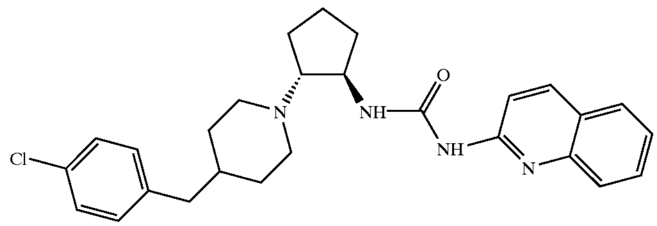 | |
| 2 | 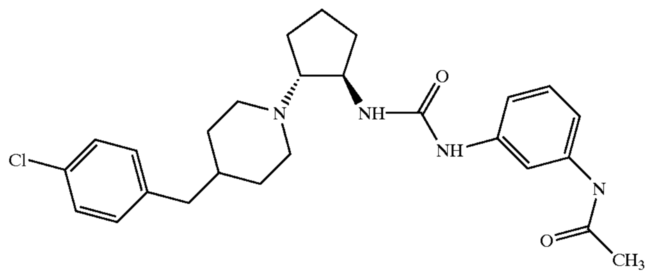 | |
| 3 | 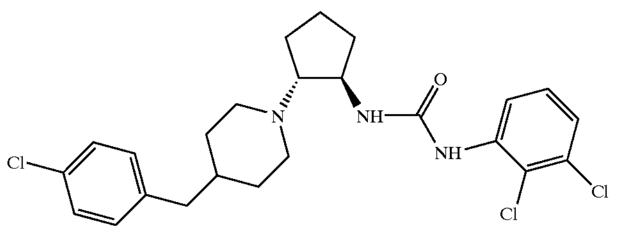 | |
| 4 | 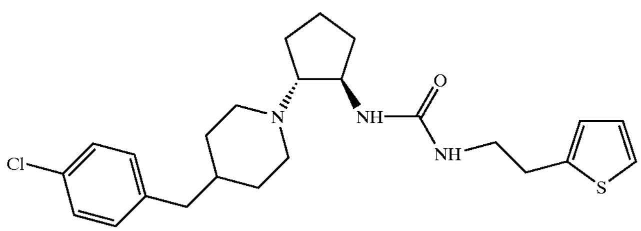 | |
| 5 | 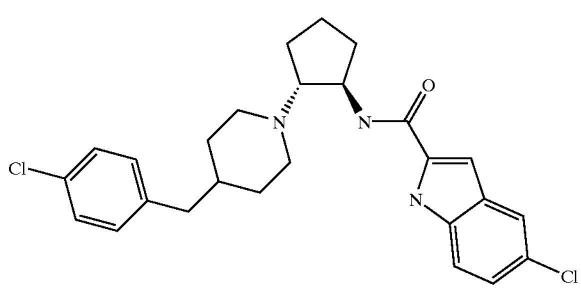 | |
| 6 | 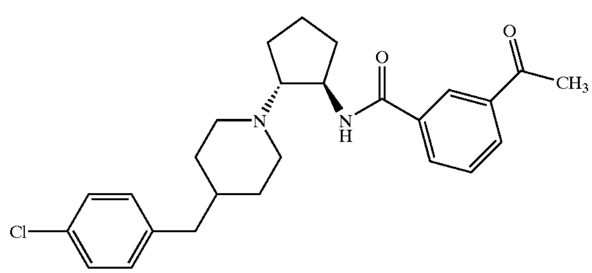 | |

TABLE I-continued

| Compound | Structure | M.P. (° C.) |
|---|---|---|
| 7 | 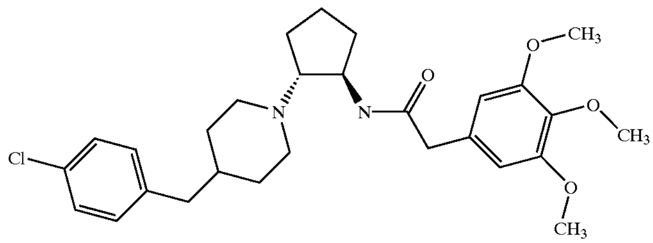 | |
| 8 | 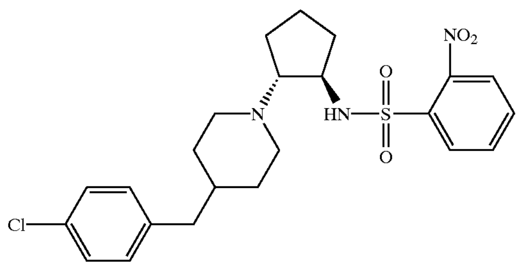 | |
| 9 | 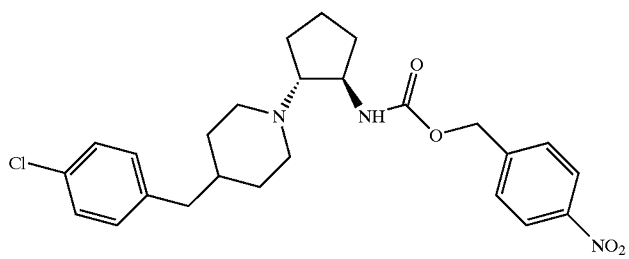 | |
| 10 | 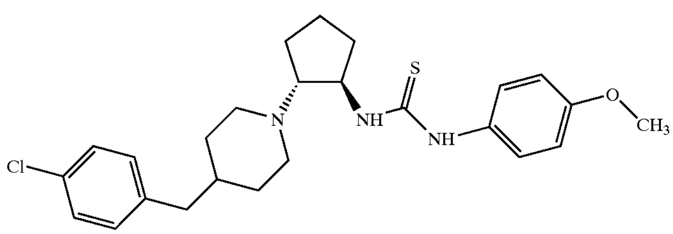 | |

PREFERRED EMBODIMENTS

While the broadest definition of this invention is set forth in the Summary of the Invention, certain compounds of Formula (I) are preferred.

A preferred compound of the invention is a compound of Formula (I) wherein $R^1$ is methylene.

One aspect of the invention relates to compounds of Formula (I) where ring A is cycloalkyl, heterocyclyl or substituted phenyl. Another preferred compound of the invention are compounds of Formula (I) wherein ring A is cyclopentyl. Compounds where ring A is cyclopentyl are bind unexpectedly potently to the CCR-3 receptor. Other preferred compounds of the invention are compounds of Formula (I) wherein ring A is heterocyclyl (particularly tetrahydropyranyl, S,S-dioxo-tetrahydothiophenyl, tetrahydrothiophenyl or pyrrolidinyl) or compounds of Formula (I) wherein ring A is substituted phenyl.

A preferred compound of the invention is a compound of Formula (I) wherein $R^2$ is phenyl ring substituted with one, or two substituents selected from alkyl, alkoxy, haloalkyl, halo, cyano or nitro; preferably methyl, ethyl, methoxy, trifluoromethyl, chloro, fluoro or bromo; most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-methylphenyl, 3-chloro-4-fluorophenyl or 3,4-dichlorophenyl. Particularly preferred are 4-chlorophenyl or 3,4-dichlorophenyl.

A preferred compound of the invention is a compound of Formula (I) wherein $R^3$ is hydrogen or methyl, preferably hydrogen.

A preferred compound of the invention is a compound of Formula (I) wherein L is —C(=O)—, —SO$_2$—, —C(=O)N(R$_a$)—, —C(=S)N(R$_a$)—, or —C(=O)O—. More preferred are compounds where L is —C(=O)—, —C(=O)N(R$_a$)—, most preferably —C(=O)N(R$_a$)—. In the preceding R$_a$ is preferably hydrogen or methyl, most preferably hydrogen.

A preferred compound of the invention is a compound of Formula (I) wherein X is absent, methylene, 1,2-ethanediyl, 1,3-propanediyl, or 1,4-butanediyl.

A preferred compound of the invention is a compound of Formula (I) wherein R⁴ is optionally substituted phenyl, optionally substituted heteroaryl wherein the heteroaryl ring is indolyl, thienyl, quinolinyl, substituted pyrimidin-2-yl, e.g. (5-(3,4-dimethoxyphenyl)pyrimidin-2-yl, 5-(3,4-methylenedioxy)-pyrimidin-2-yl or 5-(4-methoxyphenyl)pyrimidin-2-yl) or 1,8-naphthyridinyl. Preferably R⁴ is selected from 3,4-dichlorophenyl, 3,4,5-trimethoxyphenyl, 4-methanesulfonyl-phenyl, 3-methanesulfonylphenyl, 4-methoxynaphthalen-2-yl, 5-(3,4-dimethoxyphenyl)pyrimidin-2-yl, phenyl, 3-fluorophenyl, 4-ethylphenyl, 3-methoxyphenyl, 2,4-difluorophenyl, 3-trifluoromethylphenyl, 4-methylphenyl, 4-fluorophenyl, 2-fluorophenyl, 4-carboxamidophenyl, 4-acetylphenyl, 4-nitrophenyl, 2-methylphenyl, 2-chloro-4-fluorophenyl, 3,4-dimethoxyphenyl, 2,5-dimethoxyphenyl, 2,3-dichlorophenyl, 2,4-dichlorophenyl, 4-bromophenyl, 4-chloro-3-nitrophenyl, 2-nitrophenyl, 2-nitro-4-trifluoromethylphenyl, 4-chlorophenyl, 3-chlorophenyl, 2-chlorophenyl, 3-methylphenyl, 2-trifluoromethylphenyl, 2-methoxyphenyl, 3-bromophenyl, 4-trifluoromethylphenyl, 3-trifluoromethylphenyl, 3,5-bis-trifluoromethylphenyl, 4-tert-butylphenyl, 4-ethoxyphenyl, 3-cyanophenyl, 4-cyanophenyl, 4-methoxyphenyl, 3-nitrophenyl, 3,5-dimethoxyphenyl, 4-iodophenyl, 4-isopropylphenyl, 3-methoxycarbonylphenyl, 3-acetylphenyl, 2-methylphenyl, indol-2-yl, 5-methoxyindol-2-yl, 5-chloroindol-2-yl, 2-methoxycarbonylphenyl, 3,5-dichlorophenyl, 1-naphthyl, 3-chloro-2-methylphenyl, 2,5-dimethylphenyl, 2-thienyl, 3-ethoxyphenyl, 3-isoquinolyl, 2-methylquinolin-6-yl, 3-methylaminophenyl, 3-quinolyl, 2-quinolyl, 5-hydroxynaphthalen-2-yl, 8-hydroxyquinolin-2-yl, 5,7-dimethyl-[1,8]naphthyridin-2-yl, 6-quinolyl, 3-(acetylamino)phenyl, or 2,3,4-trimethoxyphenyl. Particularly preferred are R⁴ being trimethoxyphenyl, e.g 3,4,5-trimethoxyphenyl, 4-acetyl-phenyl, 4-carboxamido-phenyl and 4-methanesulfonyl-phenyl.

Also preferred are compounds where X is —CH₂S—, —CH₂O—, —CH₂CH₂— and R⁴ is heteroaryl, preferably optionally substituted pyrimidinyl, pyrazolyl or thienyl. Particularly preferred are compounds where X is —CH₂S— and R⁴ is 5-(3,4-dimethoxyphenyl)-pyrimidin-2-yl, 5-(3,4-methylenedioxyphenyl)-pyrimidin-2-yl, 5-(4-methoxyphenyl)pyrimidin-2-yl A specific compound of Formula (I) is a compound of Formula (II):

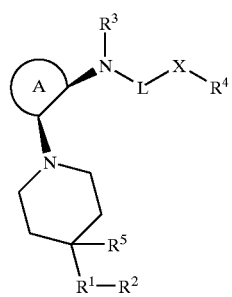

(II)

wherein R¹–R⁵, A, L, and X have any of the values described herein.

A specific compound of Formula (I) is a compound of Formula (III):

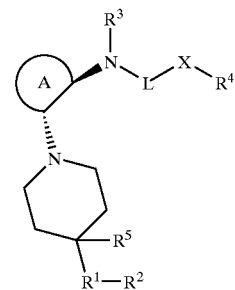

(III)

wherein R¹–R⁵, A, L, and X have any of the values described herein.

A specific compound of Formula (I) is a compound of formula (IV):

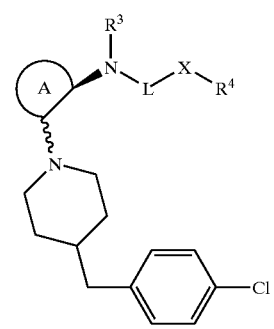

(IV)

wherein R³, R⁴, A, L, and X have any of the values described herein.

A specific compound of Formula (I) is a compound of formula (V):

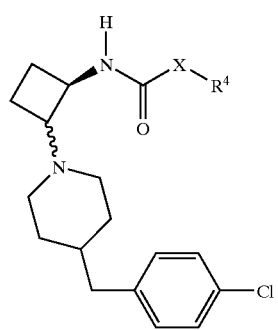

(V)

wherein X and R⁴ have any of the values defined herein.

A specific compound of Formula (I) is a compound of formula (VI):

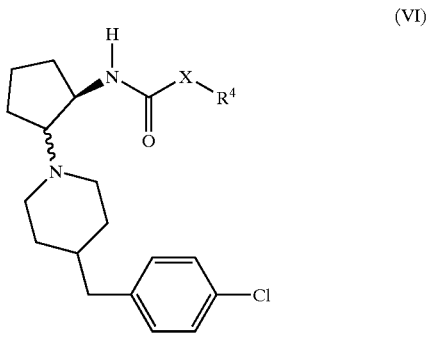

(VI)

wherein X and R⁴ have any of the values defined herein.

A specific compound of Formula (I) is a compound of formula (VII):

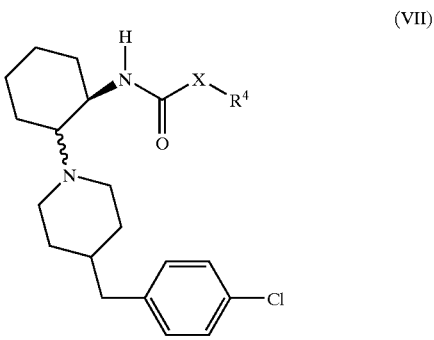

(VII)

wherein X and R⁴ have any of the values defined herein.

A specific compound of Formula (I) is a compound of formula (VIII):

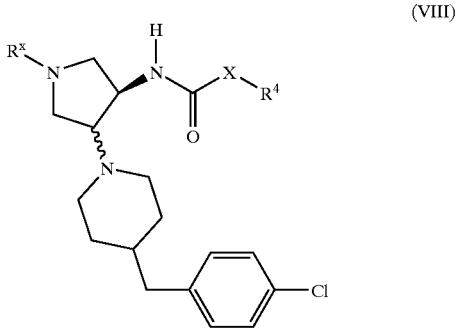

(VIII)

wherein X and R⁴ have any of the values defined herein; and R$^x$ is hydrogen, alkyl, acyl, alkylsulfonyl, aminosulfonyl, (alkylamino)sulfonyl, (dialkylamino)sulfonyl, carbamoyl, (alkylamino)carbonyl, (dialkylamino)carbonyl, (carbamoyl) alkyl, (alkylamino)carbonylalkyl, or dialkylaminocarbonylalkyl.

A specific compound of Formula (I) is a compound of formula (IX):

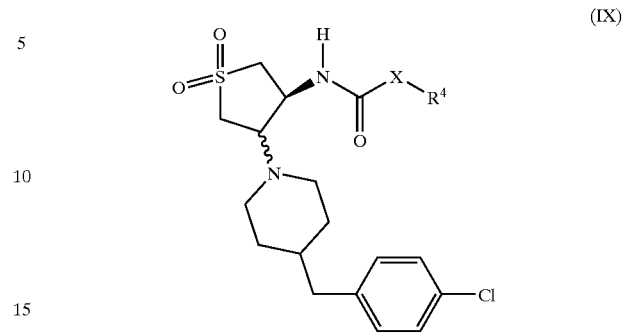

(IX)

wherein X and R⁴ have any of the values defined herein.

A specific compound of Formula (I) is a compound of formula (X):

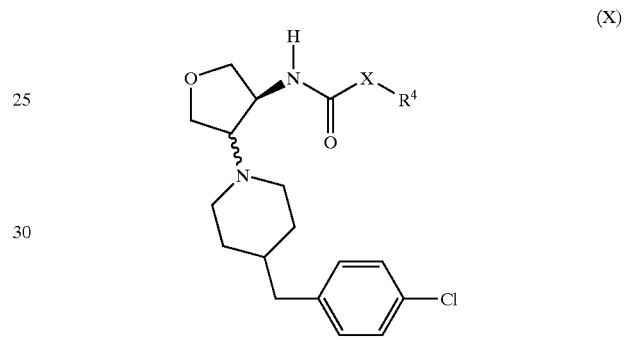

(X)

wherein X and R⁴ have any of the values defined herein.

A particularly preferred compound of the invention is:

trans-1-{2-[4-(4-chlorobenzyl)-piperidin-1-yl]-cyclopentyl}-3-(3,4,5-trimethoxy-phenyl)urea hydrochloride;

trans-1-{4-[4-(4-chlorobenzyl)-piperidin-1-yl]-tetrahydro-furan-3-yl}-3-(3,4,5-trimethoxy-phenyl)urea;

(±)-1-{(1R,2R,4S)-2-[4-(4-chlorobenzyl)piperidin-1-yl]-4-hydroxy-cyclopentyl}-3-(3,4,5-trimethoxyphenyl)urea;

(±)-1-{(1R,2R,4S)-2-[4-(4-chlorobenzyl)piperidin-1-yl]-4-hydroxymethyl-cyclopentyl}-3-(3,4,5-trimethoxyphenyl) urea; and (±)-1-{(1R,2R,4S)-2-[4-(4-chlorobenzyl)piperidin-1-yl]-4-methoxymethyl-cyclopentyl}-3-(3,4,5-trimethoxyphenyl) urea or prodrugs, individual isomers, racemic and non-racemic mixtures of isomers, and pharmaceutically acceptable salts and solvates thereof.

General Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Testing

The CCR-3 antagonistic activity of the compounds of this invention can be measured by in vitro assays such as ligand binding and chemotaxis assays as described in more detail in Examples 45, 46, and 47. In vivo activity was assayed in the Ovalbumin induced Asthma in Balb/c Mice Model as described in more detail in Example 48.

Administration and Pharmaceutical Composition

In general, the compounds of this invention can be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, transdermal, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices—nebulizer inhalers, metered-dose inhalers (MDI) and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lyopholized and the lipid mixture is suspended in an aqueous buffer and allowed to form a liposome. If necessary, the liposome size can be reduced by sonification. (see, Frank Szoka, Jr. and Demetrios Papahadjopoulos, "Comparative Properties and Methods of Preparation of Lipid Vesicles (Liposomes)", Ann. Rev. Biophys. Bioeng., 9:467–508 (1980), and D. D. Lasic, "Novel Applications of Liposomes", Trends in Biotech., 16:467–608, (1998)).

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 44.

General Synthetic Scheme

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Enika Chemie, or Sigma (St. Louis, Mo., USA), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), Butt Park Ltd., (Dist. Interchim, Montlucon Cedex, France) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 1992), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Synthesis of Compounds of Formula (I)

Compounds of Formula (I) are generally prepared from the precursor amine of Formula (Ia) as shown below.

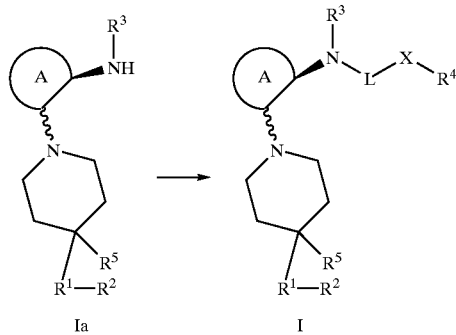

Preparation of compounds of Formula (Ia) and their conversion to compounds of Formula I is illustrated in the following Schemes 1–8.

Schemes 1–5 show methods of preparing compounds of Formula Ia having different rings A. Specific exemplification is provided for $R^1$–$R^2$ being 4-chlorobenzyl in Preparations 1–6. Preparation of analogous compounds where $R^1$ and $R^2$ vary within the full scope of the Summary of the Invention may be readily prepared by one of skill in the art in light of this specification and incorporated references.

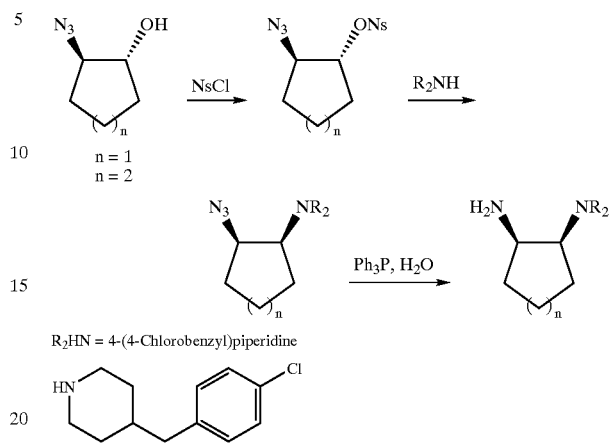

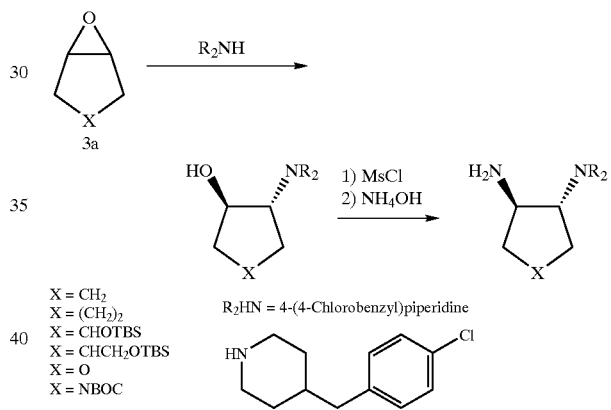

Scheme 1.
Synthesis of Cyclobutlamines-Ring A = Phenyl.

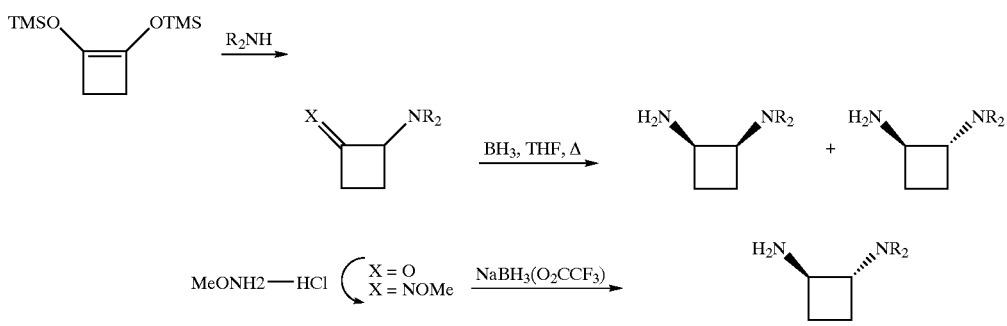

$R_2N$ = 4-(4-Chlorobenzyl)piperidine

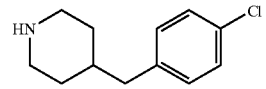

General Procedure A: (Amine Alkylation with Epoxides)

A 0.5–1.5 M solution of the amine, $R_2NH$ (1 equiv), and the specified epoxide, 3a (1.1–10 equiv) in EtOH is stirred at 80–95° C. for 2–4.5 d, allowed to cool to room temperature, and concentrated. The crude amino alcohol is purified by chromatography or recrystallization.

General Procedure B: (Amine Formation Using Methanesulfonyl Chloride and Ammonium Hydroxide)

A 0.2–0.3 M solution of the amino alcohol (1 equiv) in $CH_2Cl_2$ at 0° C. is treated successively with $Et_3N$ (2 equiv) and $MeSO_2Cl$ (2 equiv), stirred at 0° C. for 1–2 hours, and partitioned between $CH_2Cl_2$ and 10–15% $NH_4OH$. The aqueous phase is extracted with $CH_2Cl_2$ and the extracts are dried and concentrated. A 0.13M solution of the residue in 2.5:1 dioxane:28–30 wt % $NH_4OH$ is stirred at 70–80° C. 2.5–18 hours, allowed to cool to room temperature, and concentrated. The residue is partitioned between EtOAc and 1 N NaOH, the aqueous phase is extracted with EtOAc, and the extracts are washed with brine, dried and concentrated. The crude product is purified by chromatography or used without further purification.

Scheme 4.
Synthesis of Sulfone-Ring A = Sulfolane (IS THIS CORRECT??).

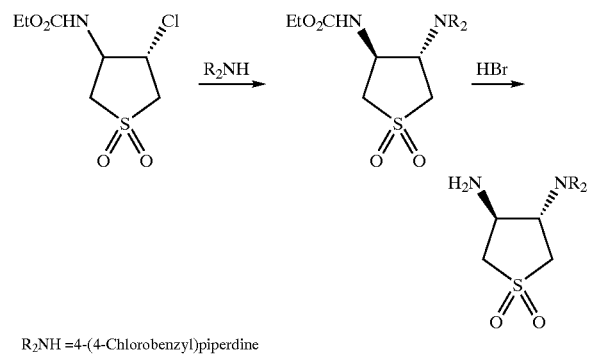

$R_2NH$ =4-(4-Chlorobenzyl)piperdine

Scheme 5.
Synthesis of Aniline - Ring A = Phenyl.

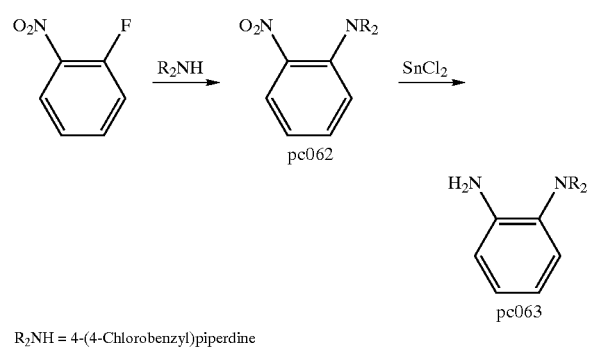

$R_2NH$ = 4-(4-Chlorobenzyl)piperdine

Schemes 6 and 7 show preparation of compounds of Formula Ia where ring A is substituted. Scheme 6 shows preparation of compounds of Formula Ia with a substituted cyclopentyl ring A. Scheme 7 shows preparation of compounds of Formula Ia with a substituted pyrrolidine ring A by treatment of the unsubstituted pyrrolidine 7a (R=H) with the appropriate reagent to produce the substituted pyrrolidine 7b.

Scheme 6.
Synthesis of Cycloalkyl Derivatives.

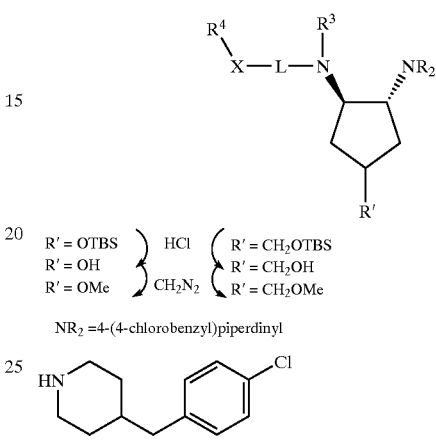

$NR_2$ =4-(4-chlorobenzyl)piperdinyl

Scheme 7.
Synthesis of Pyrrolidine Derivatives.

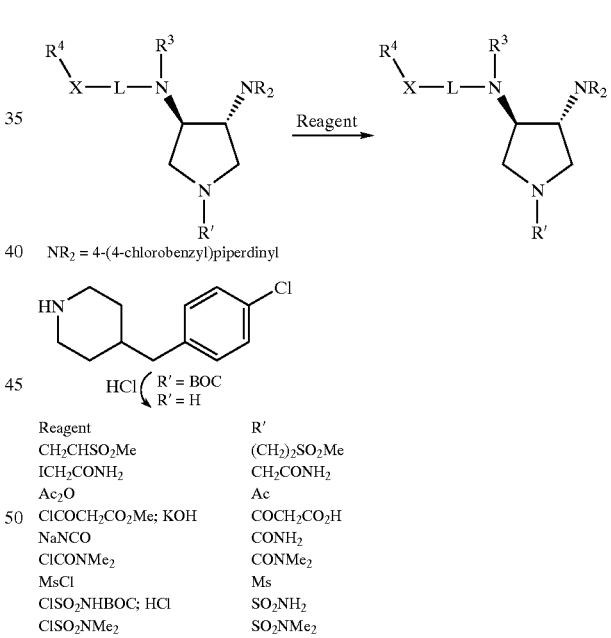

$NR_2$ = 4-(4-chlorobenzyl)piperdinyl

| Reagent | R' |
|---|---|
| $CH_2CHSO_2Me$ | $(CH_2)_2SO_2Me$ |
| $ICH_2CONH_2$ | $CH_2CONH_2$ |
| $Ac_2O$ | Ac |
| $ClCOCH_2CO_2Me$; KOH | $COCH_2CO_2H$ |
| NaNCO | $CONH_2$ |
| $ClCONMe_2$ | $CONMe_2$ |
| MsCl | Ms |
| $ClSO_2NHBOC$; HCl | $SO_2NH_2$ |
| $ClSO_2NMe_2$ | $SO_2NMe_2$ |

Schemes 8 and 9 show methods of converting compounds of Formula (Ia) to compounds of Formula (I) where L and A are varied.

Scheme 8. Conversion of Primary Amines to Ureas and Benzamides

Compounds of Formula (I) where L is —C(=O)$NR_a$ and X is absent are made as shown below in Scheme 8 (exemplified with $R^4$ being 3,4,5-trimethoxyphenyl) and General Procedures C and D. Compounds of Formula (I) where L is —C(=O)— and X is absent are made as shown below in Scheme 8 (exemplified with $R^4$ being 3,4,5-trimethoxyphenyl) and General Procedures E and F.

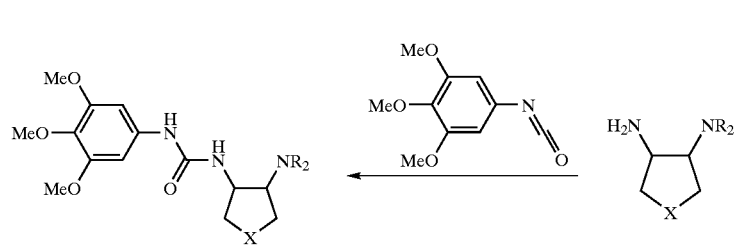
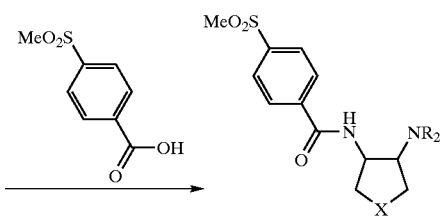

X = C, O, S(O)ₙ, NRˣ
where n = 0–2 and
Rˣ is as defined in the
Heterocyclyl definition R₂N = 4-(4-chlorobenzyl)piperdinyl

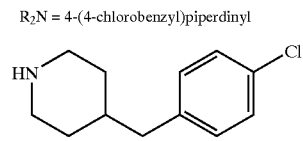

General Procedure C: (Urea Formation Using Isocyanates)

A 0.1–0.6 M solution of the amine (1 equiv) in CH₂Cl₂ or CH₂Cl₂ and DMF at 0–20° C. is treated with the specified isocyanate (1.1–2 equiv), stirred for 0.5–1.5 hours, and partitioned between CH₂Cl₂ and saturated NaHCO₃. The aqueous phase is extracted with CH₂Cl₂ and the extracts are dried and concentrated. The crude urea is purified by column chromatography or preparative TLC or used in the next step without further purification.

General Procedure D: (Urea Formation Using Isocyanates Followed by Salt Formation)

A 0.1–0.6 M solution of the amine (1 equiv) in CH₂Cl₂ or CH₂Cl₂ and DMF at 0–20° C. is treated with the specified isocyanate (1.1–2 equiv), stirred for 0.5–1.5 hours, and partitioned between CH₂Cl₂ and saturated NaHCO₃. The aqueous phase is extracted with CH₂Cl₂ and the extracts are dried and concentrated. The crude urea is purified by column chromatography or preparative TLC or used in the next step without further purification. A solution of the free base in CH₂Cl₂ is treated with 1 N HCl in Et₂O and concentrated to give the hydrochloride salt.

General Procedure E: (Amide Formation Using 1-Hydroxybenzotriazole and 1-(3-Dimethylaminopropyl)-3-ethylcarbodiimide Hydrochloride)

A 0.1–0.4 M solution of the amine (1 equiv) and the specified carboxylic acid (1.2–1.5 equiv) in CH₂Cl₂ at 0° C. is treated successively with 1-hydroxybenzotriazole hydrate (HOBt) (0.2–0.5 equiv) and 1-[3-(dimethylamino)propyl]-3-ethylcarbodiimide hydrochloride (DEC) (1.3–2 equiv), stirred at 0–20° C. for 2–72 hours, and partitioned between CH₂Cl₂ and saturated NaHCO₃. The aqueous phase is extracted with CH₂Cl₂ and the extracts are dried and concentrated. The crude amide is purified by column chromatography and/or preparative TLC.

General Procedure F: (Amide Formation Using 1-Hydroxybenzotriazole and 1-(3-Dimethylaminopropyl)-3-ethylcarbodiimide Hydrochloride Followed by Salt Formation)

A 0.1–0.4 M solution of the amine (1 equiv) and the specified carboxylic acid (1.2–1.5 equiv) in CH₂Cl₂ at 0° C. is treated successively with 1-hydroxybenzotriazole hydrate (HOBt) (0.2–0.5 equiv) and 1-[3-(dimethylamino)propyl]-3-ethylcarbodiimide hydrochloride (DEC) (1.3–2 equiv), stirred at 0–20 C. for 2–72 hours, and partitioned between CH₂Cl₂ and saturated NaHCO₃. The aqueous phase is extracted with CH₂Cl₂ and the extracts are dried and concentrated. The crude amide is purified by column chromatography and/or preparative TLC. A solution of the free base in CH₂Cl₂ is treated with 1 N HCl in Et₂O and concentrated to provide the hydrochloride salt.

Scheme 9 and following procedures G–O describe the various methods used to convert compounds of Formula Ia to compounds of Formula I where L is varied.

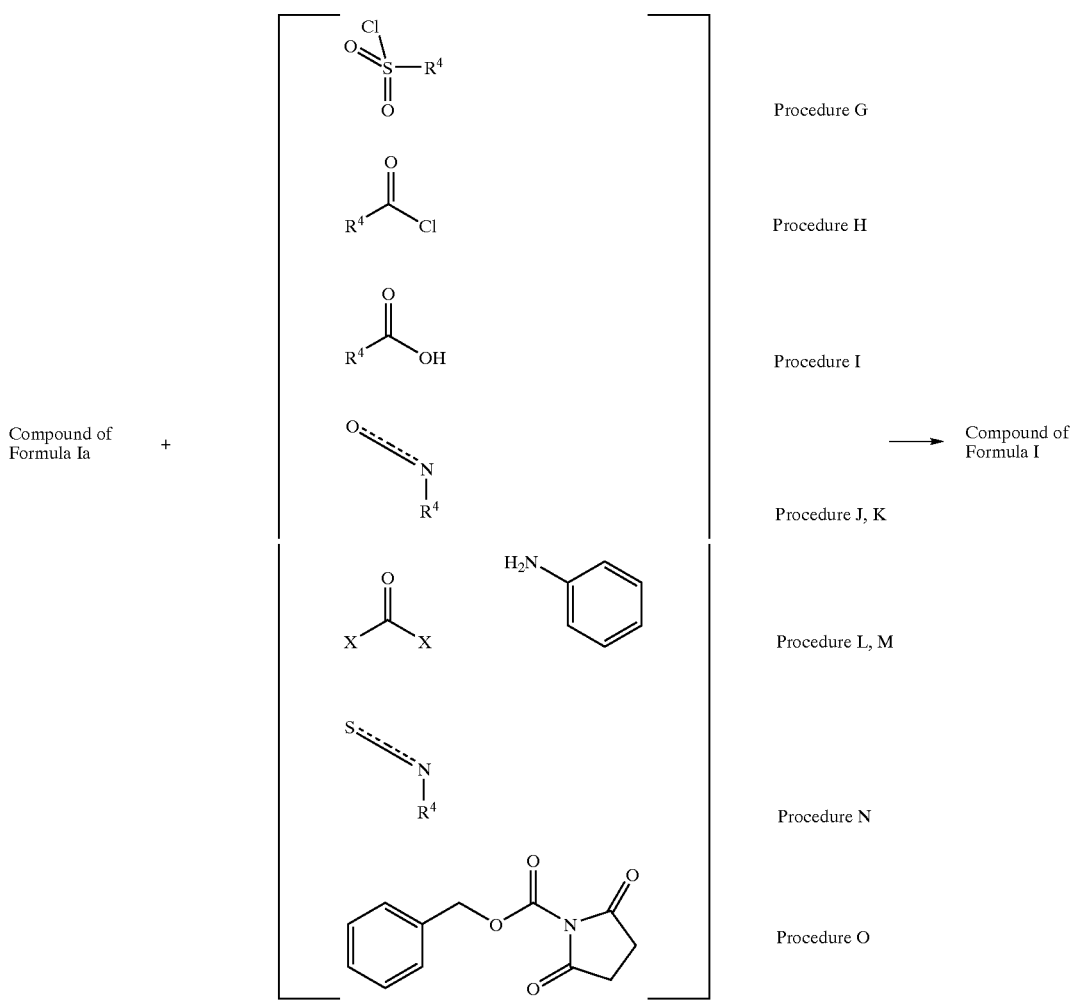

General Procedure G (Parallel Synthesis of Sulfonamides)

A mixture of the requisite amine Ia (1 equiv), the appropriate sulfonyl chloride (1.5 equiv), and Amberlite IRA67 (2 equiv) in $CH_2Cl_2$ (2 mL) was rotated overnight. The mixture was treated with PS-trisamine (1.2 equiv) (Argonaut Technologies Inc., San Carlos, Calif., USA) and rotated overnight. The solid was collected by filtration and washed with $CH_2Cl_2$, MeOH, and $CH_2Cl_2$. The filtrate was concentrated to give the product.

General Procedure H (Parallel Synthesis of Amides from Acid Chlorides)

A mixture of the requisite amine Ia (1 equiv), the appropriate acid chloride (1.5 equiv), and Amberlite IRA67 (2 equiv) in $CH_2Cl_2$ (2 mL) was rotated overnight. The mixture was treated with PS-trisamine (1.2 equiv) and MP-carbonate (2 equiv) (Argonaut Technologies, San Carlos, Calif.) and rotated overnight. The solid was collected by filtration and washed with $CH_2Cl_2$, MeOH, and $CH_2Cl_2$. The filtrate was concentrated to give the product.

General Procedure I (Parallel Synthesis of Amides from Carboxylic Acids)

A mixture of the requisite amine Ia (1 equiv), the appropriate carboxylic acid (1.5 equiv), and PS-carobodiimide (2 equiv) (Argonaut Technologies Inc., San Carlos, Calif., USA) in $CH_2Cl_2$ (2 mL) was rotated overnight. The mixture was treated with MP-carbonate (2 equiv) and rotated overnight. The solid was collected by filtration and washed with $CH_2Cl_2$, MeOH, and $CH_2Cl_2$. The filtrate was concentrated to give the product.

General Procedure J (Parallel Synthesis of Ureas from Isocyanates and Purification by Parallel Chromatography)

A mixture of the requisite amine Ia (1 equiv) and the appropriate isocyanate (1.2 equiv) in $CH_2Cl_2$ (2 mL) was stirred overnight. The mixture was concentrated to give the crude product, which was purified by parallel chromatography using a step gradient (2.5% MeOH/$CH_2Cl_2$, 10% MeOH/$CH_2Cl_2$).

General Procedure K (Parallel Synthesis of Ureas from Isocyanates and Purification by Catch and Release Scavenger)

A mixture of the requisite amine Ia (1 equiv) and the appropriate isocyanate (1.2 equiv) in $CH_2Cl_2$ (2 mL) was stirred overnight. The mixture was treated with MP-TsOH and rotated for 3 h. The solid was collected by filtration and washed with $CH_2Cl_2$, MeOH, and $CH_2Cl_2$. The solid was rotated with 2 M $NH_3$ in MeOH for 2 h. The solid was collected by filtration and washed with CH$_2$Cl$_2$, MeOH, and CH$_2$Cl$_2$. The filtrate was concentrated to give the purified product.

General Procedure L (Parallel Synthesis of Ureas from Anilines Using Phoxime Resin)

A mixture of the appropriate aniline (3 equiv) and Phoxime resin (1 equiv) in CH$_2$Cl$_2$ (2 mL) was rotated for 3 h. If the aniline had not dissolved, triethylamine (3.5 equiv) was added. The mixture was rotated overnight. The solid was collected by filtration and washed with CH$_2$Cl$_2$, MeOH, CH$_2$Cl$_2$, MeOH, and CH$_2$Cl$_2$. A mixture of the solid and the requisite amine Ia (1.1 equiv) in CH$_2$Cl$_2$ (0.5 mL) and toluene (1.5 mL) were heated at 80° C. with shaking overnight and allowed to cool to room temperature. The solid was collected by filtration and washed with CH$_2$Cl$_2$, MeOH, and CH$_2$Cl$_2$. The filtrate was concentrated to give the product.

General Procedure M (Parallel Synthesis of Ureas from Anilines Using Triphosgene)

A mixture of the appropriate aniline (1.2 equiv), triphosgene (0.4 equiv), and triethylamine (1.4 equiv) in CH$_2$Cl$_2$ was heated at 35° C. for 1 h. After cooling to room temperature, the requisite amine Ia (1 equiv) was added. The mixture was stirred overnight, washed with H$_2$O and brine, passed through Na$_2$SO$_4$, and concentrated to give crude product which was purified by parallel chromatography.

General Procedure N (Parallel Synthesis of Thioureas from Thioisocyanates)

A mixture of the requisite amine Ia (1 equiv) and the appropriate thioisocyanate (1.2 equiv) in CH$_2$Cl$_2$ (2 mL) was stirred overnight. The mixture was treated with MP-TsOH and rotated for 3 h. The solid was collected by filtration and washed with CH$_2$Cl$_2$, MeOH, and CH$_2$Cl$_2$. The solid was rotated with 2 M NH$_3$ in MeOH for 2 h. The solid was collected by filtration and washed with CH$_2$Cl$_2$, MeOH, and CH$_2$Cl$_2$. The filtrate was concentrated to give the purified product.

General Procedure O (Parallel Synthesis of Carbamates)

A mixture of the requisite amine Ia (1 equiv) and the appropriate succinimide (1.5 equiv) in CH$_2$Cl$_2$ (2 mL) was stirred overnight. If the reaction was not complete, it was heated at 38° C. for 1 hour. The mixture was washed with H$_2$O and brine, passed through Na$_2$SO$_4$ and concentrated to give the crude product which was purified via parallel purification (step gradient 5% MeOH/CH$_2$Cl$_2$, 10% MeOH/CH$_2$Cl$_2$).

Experimental Section

General

Unless otherwise noted, all non-aqueous reactions were run under a nitrogen atmosphere and Na$_2$SO$_4$ was used to dry all organic layers. Purifications were typically carried out by flash chromatography on silica gel (230–400 mesh) or preparative TLC on Uniplate Silica Gel GF PLC Plates (20×20 cm, 1000 microns) from Analtech, Inc., Newark, Del. Alumina used was basic with 6 wt % H$_2$O (Brockmann Ill.). Melting points taken in capillary tubes are uncorrected. IR spectra were determined in KBr. NMR spectra were run in CDCl3, unless otherwise indicated. $^1$H NMR spectra were recorded on 300 MHz instruments and $^{13}$C NMR spectra were recorded at 75.5 MHz. Mass spectral analyses were accomplished using electrospray ionization. Analytical reverse-phase HPLC was performed on Shimadzu system equipped with a diode array spectrometer (range 190–300 nm; Hewlett Packard). The stationary phase was a Zorbax SB-Phenyl Rapid Resolution column (4.6 mm×50 mm; Hewlett Packard), mobile phase A was 0.1% trifluoroacetic acid, and mobile phase B was CH$_3$CN. A flow rate of 2.5 mL/min with a linear gradient of 20–55% B in 5 min and then 55–20% B in 5 min was employed. Other physical and analytical data were obtained by the physical and analytical chemistry group at Roche Bioscience. All parallel synthesis reactions were run in sealed tubes that were vented prior to rotated overnight. Amberlite IRA67 (Aldrich Chemical Co., Milwaukee, Wis., USA) was washed consecutively with CH$_2$Cl$_2$, MeOH, CH$_2$Cl$_2$, MeOH, CH$_2$Cl$_2$ and then dried under vacuum prior to use. All products derived from parallel synthesis reactions were characterized via HPLC-MS.

EXAMPLES

The following preparations and Examples are given to enable those skilled in the art to more clearly understand and to practice the present invention. They should not be considered as limiting the scope of the invention, but merely as being illustrative and representative thereof.

The following Preparations (1–6) are useful for preparing synthetic intermediates that can be used to prepare compounds of the invention, as described in the following Examples.

Preparation 1: Preparation of (±)-trans-2-[4-(4-chlorobenzyl)piperidin-1-yl]-cyclohexylamine

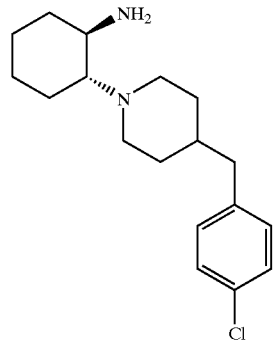

Step A: Preparation of (±)-trans-2-[4-(4-chlorobenzyl) piperidin-1-yl]-cyclohexanol

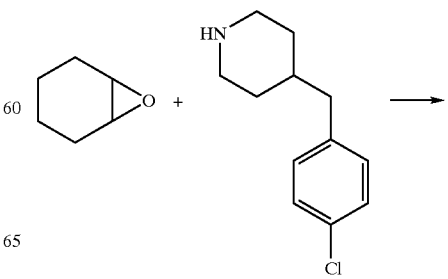

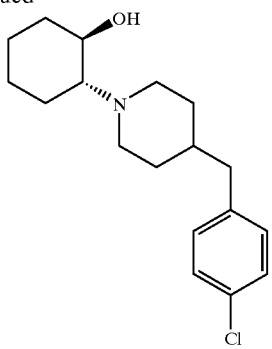

Following Procedure A, 4-(4-chlorobenzyl)-piperidine (see Preparation 7) (52 mg, 0.25 mmol) was alkylated with 7-oxa-bicyclo[4.1.0]heptane (0.25 mL, 2.5 mmol) in EtOH (0.5 mL) at 80° C. for 3 d. Chromatography of the crude product with 90:9.5:0.5–80:19:1 CH$_2$Cl$_2$:MeOH:NH$_4$OH gave the product (68 mg, 88%) as a tan oil which solidified upon standing as a cream solid: mp 100–101.3° C.; IR 3379, 2929 cm$^{-1}$; $^1$H NMR δ 1.05–1.76 (m, 12H), 2.02 (dt, J=2.4, 11.6 Hz, 1H), 2.06–2.20 (m, 2H), 2.49 (d, J=7.0 Hz, 2H), 2.51–2.64 (m, 2H), 2.79 (m, 1H), 3.34 (m, 1H), 4.05 (m, 1H), 7.06 (m, 2H), 7.24 (m, 2H); MS m/z 308 (M+H)$^+$. Anal. (C$_{18}$H$_{26}$ClNO) C, H, N.

Step B: Preparation of (±)-trans-2-[4-(4-chlorobenzyl)piperidin-1-yl]-cyclohexylamine

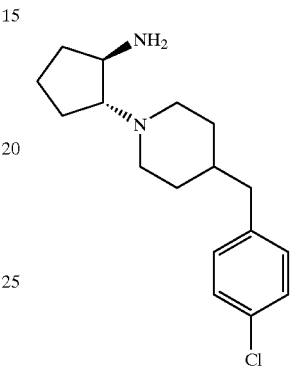

A solution of (±)-trans-2-[4-(4-chlorobenzyl)piperidin-1-yl]-cyclohexanol (390 mg, 1.27 mmol) in CH$_2$Cl$_2$ (6 mL) at 0° C. was treated successively with Et$_3$N (350 μL, 2.53 mmol) and MeSO$_2$Cl (194 μL, 2.53 mmol), stirred at 0° C. for 2 hours, and partitioned between CH$_2$Cl$_2$ and 10% NH$_4$OH. The aqueous phase was extracted with CH$_2$Cl$_2$ and the extracts were washed with brine, dried and concentrated. A solution of the residue in THF (3 mL) and 28–30 wt % NH$_4$OH (1.2 mL) was stirred at 70° C. for 24 hours, allowed to cool to room temperature, and partitioned between EtOAc and 1 N NaOH. The aqueous phase was extracted with EtOAc and the extracts were washed with brine, dried and concentrated. Chromatography of the residue on alumina with 1:3 EtOAc:MeOH to 100% MeOH and a subsequent chromatography on alumina with 20:1 hexanes:EtOAc to 100% EtOAc followed by 3:1 EtOAc:MeOH to 100% MeOH gave the product (260 mg, 67%) as a tan oil which solidified upon standing: mp 69.1–70.4° C.; $^1$H NMR δ 1.03–1.34 (m, 6H), 1.37–1.52 (m, 1H), 1.57–1.77 (m, 5H), 1.92–2.05 (m, 3H), 2.48 (d, J=7.0 Hz, 2H), 2.45–2.64 (m, 3H), 2.73 (m, 1H), 7.06 (m, 2H), 7.23 (m, 2H); MS m/z 307 (M+H)$^+$.

Preparation 2: Preparation of (±)-trans-2-[4-(4-chlorobenzyl)piperidin-1-yl]-cyclopentylamine

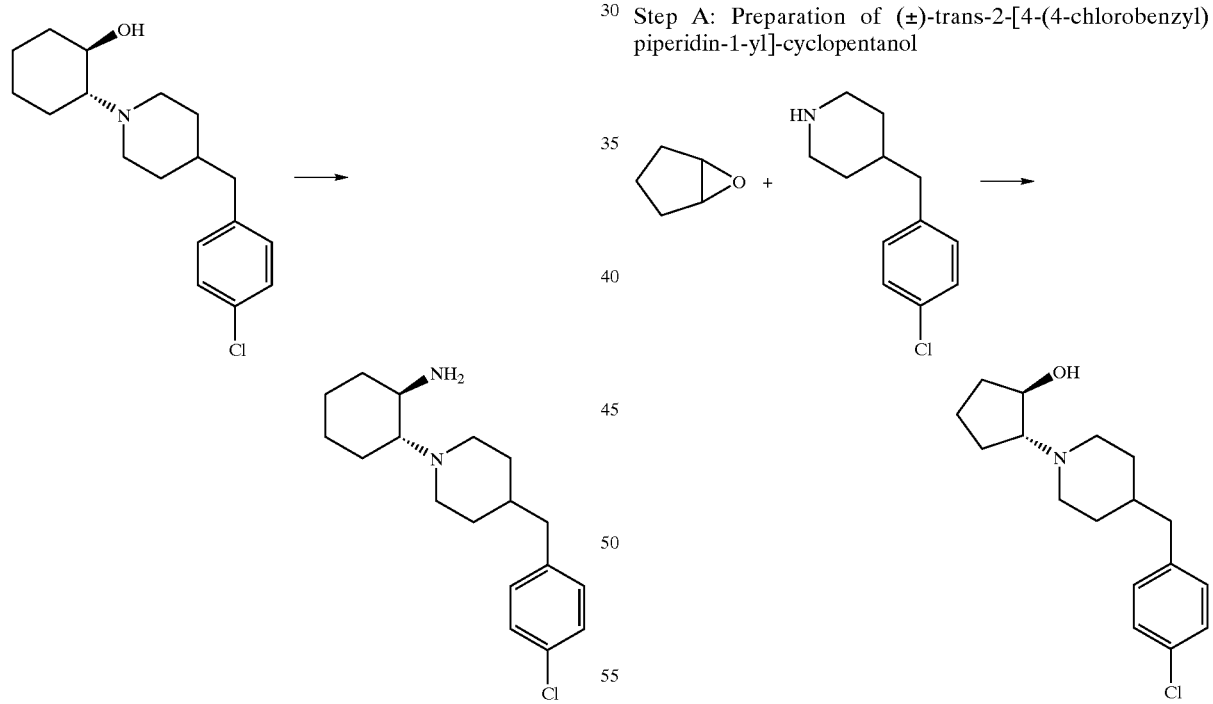

Step A: Preparation of (±)-trans-2-[4-(4-chlorobenzyl)piperidin-1-yl]-cyclopentanol Following General Procedure A, a solution of 4-(4-chlorobenzyl)-piperidine (17.86 g, 85.05 mmol) and 6-oxa-bicyclo[3.1.0]hexane (50 g, 0.6 mol) in EtOH (170 mL) was stirred at 95° C. for 40 hours, allowed to cool to room temperature, and concentrated. The residue was crystallized in hot CH$_2$Cl$_2$ (80 mL), the crystallization mixture was concentrated to half the volume, and kept at 0° C. overnight and filtered, and the precipitate was rinsed with cold hexanes to give the product (18.2 g, 73%) as a tan solid. The mother liquors were concentrated to half the volume, diluted with CH$_2$Cl$_2$ and kept at −10° C. for 1 hour, and the precipitate was rinsed with cold CH$_2$Cl$_2$ and hexanes to give additional product (1.8 g, 7%) as a tan solid: mp 104.1–105.5° C.; IR 3436, 2928 cm$^{-1}$; $^1$H NMR δ 1.19–1.75 (m, 8H), 1.81–1.99 (m, 4H), 2.06 (dt, J=2.5, 11.7 Hz, 1H), 2.47 (m, 1H), 2.50 (d, J=7.0 Hz, 2H), 2.90 (m, 1H), 3.07 (m, 1H), 4.10 (m, 1H), 7.06 (m, 2H), 7.23 (m, 2H); $^{13}$C NMR δ 21.63, 27.35, 32.01, 32.15, 34.31, 37.87, 42.47, 50.47, 52.97, 75.15, 75.22, 128.27, 130.43, 131.55, 139.04; MS m/z 294 (M+H)$^+$. Anal. (C$_{17}$H$_{24}$ClNO.0.1H$_2$O) C, H, N.

Step B: Preparation of (±)-trans-2-[4-(4-chlorobenzyl)piperidin-1-yl]-cyclopentylamine

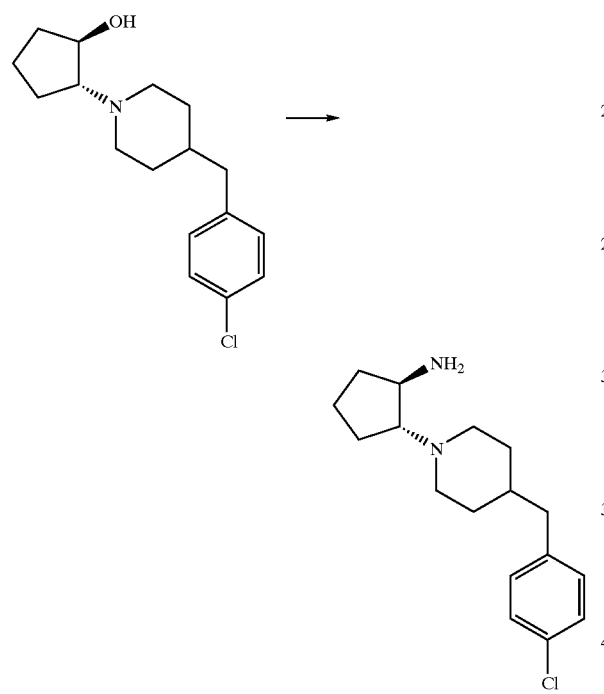

Following General Procedure B, a solution of (±)-trans-2-[4-(4-chlorobenzyl)piperidin-1-yl]-cyclopentanol (205 mg, 0.697 mmol) in CH$_2$Cl$_2$ (2.8 mL) at 0° C. was treated successively with Et$_3$N (190 μL, 1.4 mmol) and MeSO$_2$Cl (110 μL, 1.4 mmol), stirred at 0° C. for 1 hour, and partitioned between CH$_2$Cl$_2$ and 10% NH$_4$OH. The aqueous phase was extracted with CH$_2$Cl$_2$ and the extracts were dried and concentrated to give 220 mg of an oil. A solution of the residue (110 mg) in dioxane (2 mL) and 28–30 wt % NH$_4$OH (0.8 mL) was stirred at 70–80° C. overnight, allowed to cool to room temperature, and concentrated. The residue was partitioned between EtOAc and 1 N NaOH, the aqueous phase was extracted with EtOAc, and the extracts were washed with brine, dried and concentrated. Chromatography of the residue on alumina with 10:1 hexanes:EtOAc to 100% EtOAc followed by 95:4.75:0.25–60:38:2 CH$_2$Cl$_2$:MeOH:NH$_4$OH gave the product (87 mg, 85%) as an oil: $^1$H NMR δ 1.18–1.71 (m, 9H), 1.76–2.00 (m, 3H), 2.07 (dt, J=2.4, 11.5 Hz, 1H), 2.31 (m, 1H), 2.50 (d, J=6.9 Hz, 2H), 2.86–2.99 (m, 2H), 3.19 (m, 1H), 7.06 (m, 2H), 7.23 (m, 2H); MS m/z 293.2 (M+H)$^+$.

Preparation 3: Preparation of (±)-cis-2-[4-(4-chlorobenzyl)piperidin-1-yl]-cyclopentylamine

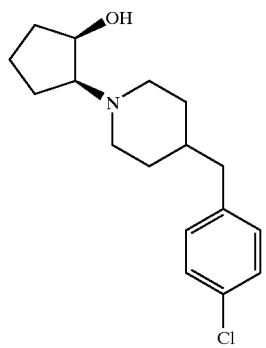

Step A: Preparation of (±)-trans-4-nitro-benzenesulfonic acid 2-azido-cyclopentyl ester

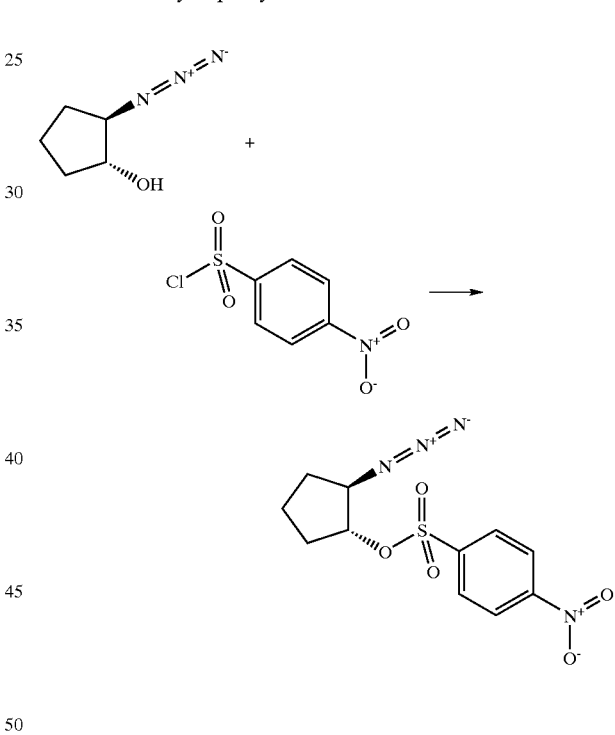

A solution of (±)-trans-2-azido-cyclopentanol (1.27 g, 10.0 mmol) (Zhang, Z. da; Scheffold, R. Helv. Chim. Acta 1993, 76, 2602) in CH$_2$Cl$_2$ (14 mL) at 0° C. was treated successively with pyridine (0.88 mL, 10.9 mmol) and 4-nitro-benzenesulfonyl chloride (2.22 g, 10.0 mmol) and allowed to warm to room temperature slowly. The reaction was stirred for 4 d, during which additional pyridine (0.9 mL, 11 mmol) and 4-nitro-benzenesulfonic acid (2.2 g, 10 mmol) was added, and partitioned between CH$_2$Cl$_2$ and 1 N HCl. The aqueous phase was extracted with CH$_2$Cl$_2$ and the extracts were washed with saturated NaHCO$_3$, dried and concentrated. Chromatography of the residue with 10:1–4:1 hexanes:EtOAc gave the product (2.63 g, 84%) as a yellow oil: $^1$H NMR δ 1.61–1.90 (m, 4H), 2.00–2.16 (m, 2H), 3.96 (m, 1H), 4.72 (m, 1H), 8.14 (m, 2H), 8.43 (m, 2H).

Step B: Preparation of (±)-cis-1-(2-azido-cyclopentyl)-4-(4-chlorobenzyl)-piperidine

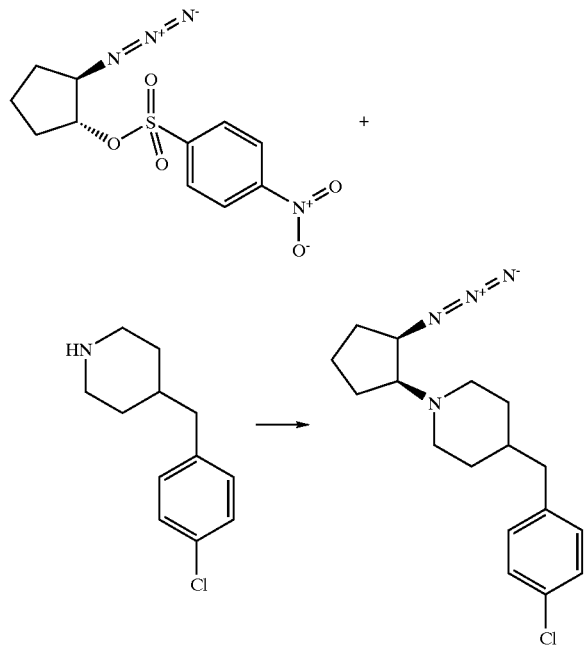

A murky solution of (±)-trans-4-nitro-benzenesulfonic acid 2-azido-cyclopentyl ester (630 mg, 2.0 mmol), 4-(4-chlorobenzyl)-piperidine (420 mg, 2.0 mmol), and $Et_3N$ (280 μL, 2.0 mmol) in $CH_3CN$ (4 mL) was stirred at room temperature for 10 d and 65° C. for 2 d, allowed to cool to room temperature, and concentrated. The residue was partitioned between $CH_2Cl_2$ and 1 N NaOH, the aqueous phase was extracted with $CH_2Cl_2$ and the extracts were dried and concentrated. Chromatography of the residue with 20:1–1:1 hexanes:EtOAc followed by chromatography with 100% $CH_2Cl_2$ to 95:4.75:0.25 $CH_2Cl_2$:MeOH:$NH_4OH$ gave the product (145 mg, 22%) as a tan oil: $^1H$ NMR δ 1.32–1.90 (m, 13H), 2.33 (m, 1H), 2.49 (d, J=6.4 Hz, 2H), 2.96 (m, 1H), 3.06 (m, 1H), 4.04 (t, J=4.0 Hz, 1H), 7.06 (m, 2H), 7.23 (m, 2H); MS m/z 319.2 (M–H)⁻.

Step C: Preparation of (±)-cis-2-[4-(4-chlorobenzyl)piperidin-1-yl]-cyclopentylamine

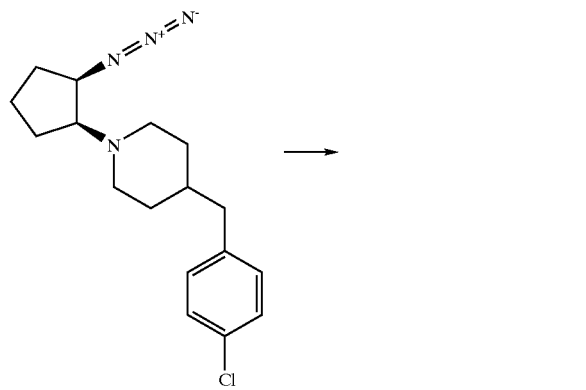

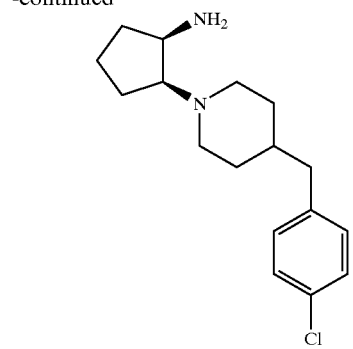

A solution of (±)-cis-1-(2-azido-cyclopentyl)-4-(4-chlorobenzyl)-piperidine (210 mg, 0.65 mmol) in THF (2.5 mL) was treated successively with $PPh_3$ (514 mg, 1.96 mmol) and $H_2O$ (141 μL, 7.83 mmol), refluxed for 3.5 hours, allowed to cool to room temperature, and concentrated. Chromatography of the residue with 90:9.5:0.5–75:23.75:1.25 $CH_2Cl_2$:MeOH:$NH_4OH$ gave the product (183 mg, 95%) as a colorless oil which solidified upon standing to a cream solid: mp 69.6–71.3° C.; $^1H$ NMR δ 1.20–1.35 (m, 2H), 1.43–1.93 (m, 11H), 2.17 (m, 1H), 2.49 (d, J=6.9 Hz, 2H), 2.89–3.02 (m, 2H), 3.34 (t, J=4.4 Hz, 1H), 7.06 (m, 2H), 7.23 (m, 2H); $^{13}C$ NMR δ 20.72, 27.08, 32.48, 32.61, 38.32, 42.95, 52.14, 53.09, 53.61, 71.49, 128.63, 130.80, 131.88, 139.58; MS m/z 293.2 (M+H)⁺.

Preparation 4: Preparation of (±)-cis-2-[4-(4-chlorobenzyl)piperidin-1-yl]-cyclohexylamine

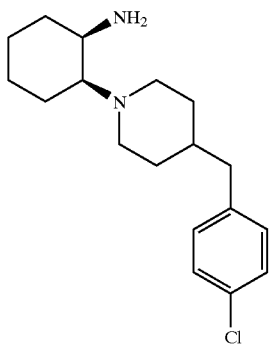

Step A: Preparation of (±)-trans-4-nitro-benzenesulfonic acid 2-azido-cyclohexyl ester

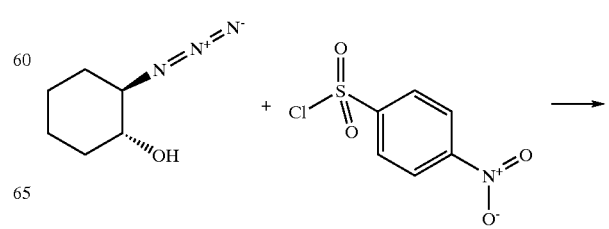

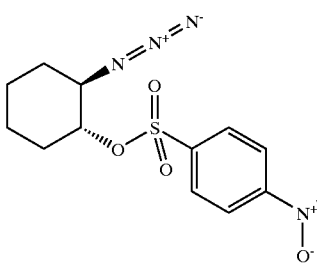

A solution of (±)-trans-2-azidocyclohexan-1-ol (11.3 g, 80.0 mmol) (Zhang, Z. da; Scheffold, R. *Helv. Chim. Acta* 1993, 76, 26021 in CH$_2$Cl$_2$ (110 mL) at 0° C. was treated successively with pyridine (14.2 mL, 176 mmol) and 4-nitro-benzenesulfonyl chloride (35.6 g, 160 mmol), allowed to warm to room temperature slowly, stirred for 4 d, and partitioned between CH$_2$Cl$_2$ and 1 N HCl. The aqueous phase was extracted with CH$_2$Cl$_2$ and the extracts were washed with saturated NaHCO$_3$, dried and concentrated. Chromatography of the residue with 10:1–1:1 hexanes:EtOAc gave the product (19 g, 72%) as a cream solid: $^1$H NMR δ 1.19–1.39 (m, 3H), 1.53–1.82 (m, 3H), 2.00–2.10 (m, 1H), 2.26 (m, 1H), 3.36 (m, 1H), 4.35 (ddd, J=4.7, 9.2, 10.8 Hz, 1H), 8.17 (m, 2H), 8.41 (m, 2H).

Step B: Preparation of (±)-cis-1-(2-azido-cyclohexyl)-4-(4-chlorobenzyl)-piperidine

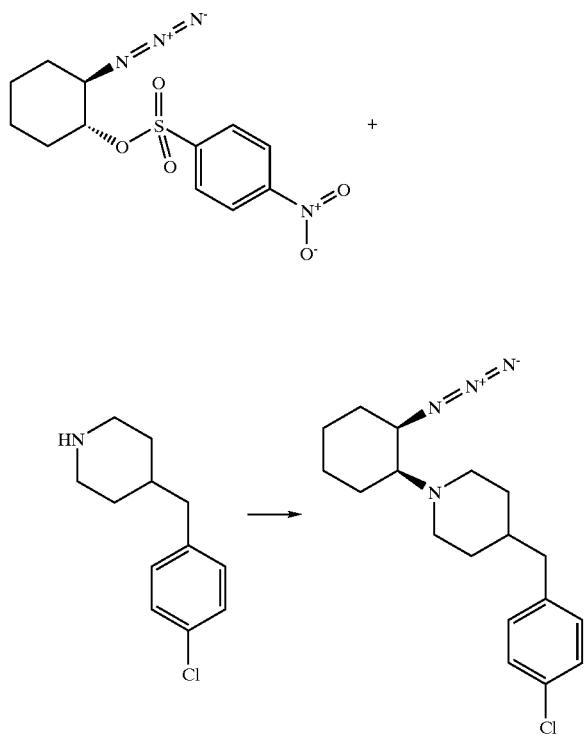

A murky solution of (±)-trans-4-nitro-benzenesulfonic acid 2-azido-cyclohexyl ester (1.77 g, 5.41 mmol), 4-(4-chlorobenzyl)-piperidine (1.14 g, 5.43 mmol), and Et$_3$N (0.75 mL, 5.4 mmol) in CH$_3$CN (11.2 mL) was stirred at room temperature for 17 hours, 65° C. for 31 hours, and 80° C. for 5 d, allowed to cool to room temperature, and concentrated. The residue was partitioned between CH$_2$Cl$_2$ and 1 N NaOH, the aqueous phase was extracted with CH$_2$Cl$_2$ and the extracts were dried and concentrated. Chromatography of the residue with 98:1.9:0.1–95:4.75:0.25 CH$_2$Cl$_2$:MeOH:NH$_4$OH to 100% MeOH and subsequent chromatography with 10:1 hexanes:EtOAc to 100% EtOAc followed by 95:5 EtOAc:MeOH gave, in order of elution, starting (±)-trans-4-nitro-benzenesulfonic acid 2-azidocyclohexyl ester (1.2 g, 68%), desired product (155 mg, 9%), and starting 4-(4-chlorobenzyl)-piperidine (810 mg, 71%). Product: $^1$H NMR δ 1.19–1.81 (m, 12H), 1.92–2.08 (m, 3H), 2.22 (m, 1H), 2.48 (d, J=7.0 Hz, 2H), 3.02 (m, 2H), 4.05 (m, 1H), 7.06 (m, 2H), 7.23 (m, 2H); MS m/z 333.2 (M+H)$^+$.

Step C: Preparation of (±)-cis-2-[4-(4-chlorobenzyl) piperidin-1-yl]-cyclohexylamine

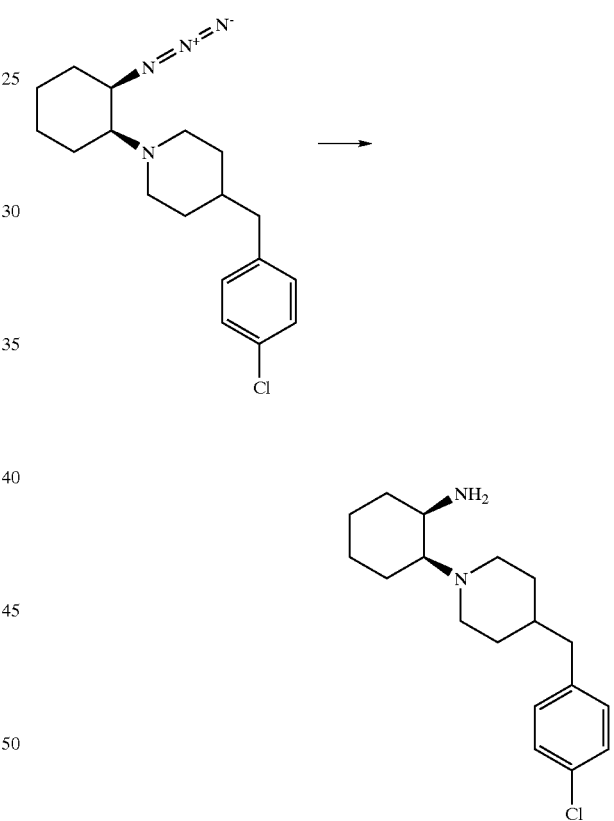

A solution of (±)-cis-1-(2-azido-cyclohexyl)-4-(4-chlorobenzyl)-piperidine (155 mg, 0.463 mmol) in THF (1.8 mL) was treated successively with PPh$_3$ (364 mg, 1.39 mmol) and H$_2$O (141 μL, 5.56 mmol), refluxed for 3 hours, allowed to cool to room temperature, and concentrated. Chromatography of the residue with 95:4.75:0.25–75:23.75:1.25 CH$_2$Cl$_2$:MeOH:NH$_4$OH gave the product (121 mg, 85%) as a cream solid: $^1$H NMR δ 1.14–1.93 (m, 15H), 1.96 (dt, J=11.8, 3.5 Hz, 1H), 2.48 (d, J=7.0 Hz, 2H), 3.03–3.13 (m, 2H), 3.30 (m, 1H), 7.06 (m, 2H), 7.23 (m, 2H); MS m/z 307.2 (M+H)$^+$.

Preparation 5: Preparation of (±)-trans-2-[4-(4-chlorobenzyl)piperidin-1-yl]-cyclobutylamine

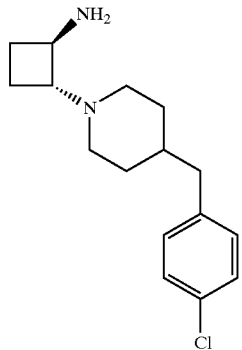

Step A: Preparation of (±)-2-[4-(4-chlorobenzyl)piperidin-1-yl]-cyclobutanone

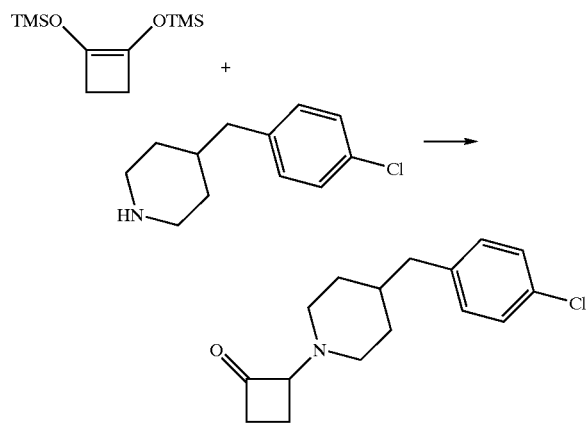

1,2-Bis(trimethylsilyloxy)cyclobutene (5.0 g, 22 mmol) at 0° C. under Ar was treated dropwise during 15 min with a solution of 4-(4-chlorobenzyl)-piperidine (4.56 g, 21.7 mmol) in MeOH (10.9 mL) and allowed to warm to room temperature. The reaction was stirred over a period of 5 hours, during which additional 1,2-bis(trimethylsilyloxy)cyclobutene (0.99 g, 4.3 mmol) was added, and concentrated. Chromatography of the residue with 95:4.75:0.25 CH$_2$Cl$_2$:MeOH:NH$_4$OH gave the product (4.8 g, 80%) as a yellow oil: $^1$H NMR δ 1.20–1.35 (m, 2H), 1.43–1.64 (m, 3H), 1.93–2.18 (m, 4H), 2.49 (d, J=6.9 Hz, 2H), 2.64–2.91 (m, 3H), 3.14 (m, 1H), 3.90 (m, 1H), 7.05 (m, 2H), 7.23 (m, 2H); MS m/z 278.1 (M+H)$^+$.

Step B: Preparation of (±)-2-[4-(4-chlorobenzyl)piperidin-1-yl]-cyclobutanone O-methyl-oxime

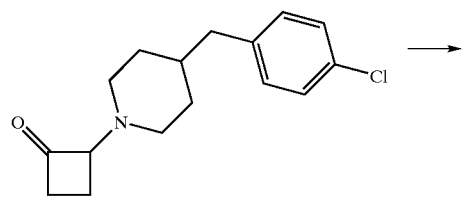

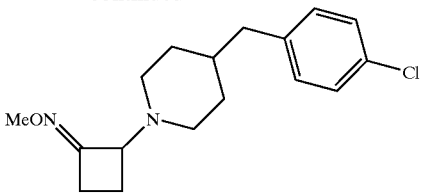

A solution of (±)-2-[4-(4-chlorobenzyl)piperidin-1-yl]-cyclobutanone
(1.74 g, 6.26 mmol) and MeONH$_2$.HCl (2.63 g, 31.3 mmol) in MeOH (20 mL) was stirred at 65° C. under Ar for 3 hours, allowed to cool to room temperature, and concentrated. The residue was partitioned between CH$_2$Cl$_2$ and saturated NaHCO$_3$, the aqueous phase was extracted with CH$_2$Cl$_2$, and the extracts were dried and concentrated. Chromatography of the residue with 95:4.75:0.25 CH$_2$Cl$_2$:MeOH:NH$_4$OH gave the product (1.5 g, 78%) as a brown oil and predominantly one stereoisomer: $^1$H NMR δ 1.05–1.65 (m, 4.5H), 1.92–2.11 (m, 4H), 2.45–2.65 (m, 3H), 2.73–2.96 (m, 2H), 3.22 (m, 1H), 3.73 (m, 1H), 3.82 (m, 3H), 4.57 (m, 0.5H), 7.06 (m, 2H), 7.23 (m, 2H); MS m/z 307.1 (M+H)$^+$.

Step C: Preparation of (±)-trans-2-[4-(4-chlorobenzyl)piperidin-1-yl]-cyclobutylamine

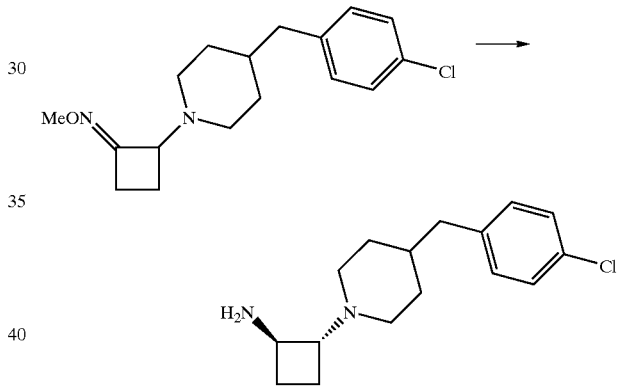

A mixture of NaBH$_4$ (604 mg, 16.0 mmol) in THF (13 mL) under Ar was treated dropwise with trifluoroacetic acid (1.23 mL, 16.0 mmol), stirred for 5 min, treated dropwise with a solution of (±)-2-[4-(4-chlorobenzyl)piperidin-1-yl]-cyclobutanone O-methyl-oxime (985 mg, 3.21 mmol) in THF (35 mL), and stirred at room temperature for 5 h. The mixture was treated carefully with 6 N HCl (1.5 mL) until the pH~2, stirred for 10 min, basified with 8 N NaOH until the pH~10, and partitioned between EtOAc and 1 N NaOH. The aqueous phase was extracted with EtOAc and the extracts were washed with brine, dried (Na$_2$SO$_4$) and concentrated. A solution of the residue in MeOH (30 mL) and 1 N HCl (3 mL) was stirred at 50° C. for 1 h and at 75° C. for 5 hours, allowed to cool to room temperature, and concentrated. The residue was partitioned between CH$_2$Cl$_2$ and 1 N NaOH, the aqueous phase was extracted with CH$_2$Cl$_2$ and the extracts were dried and concentrated. Chromatography of the residue on alumina with 10:1 hexanes:EtOAc to 100% EtOAc followed by 98:1.9:0.1–90:9.5:0.5 CH$_2$Cl$_2$:MeOH:NH$_4$OH gave 400 mg of the product (80% pure by $^1$H NMR) as a yellow oil which was used without further purification: $^1$H NMR δ 1.19–1.90 (m, 9H), 2.11 (m, 1H), 2.28 (m, 1H), 2.44–2.59 (m, 3H), 2.80 (m, 1H), 3.05 (m, 1H), 3.22 (m, 1H), 7.06 (m, 2H), 7.23 (m, 2H); MS m/z 279.2 (M+H)$^+$.

Preparation 6: Preparation of (±)-cis-2-[4-(4-chlorobenzyl)piperidin-1-yl]-cyclobutylamine

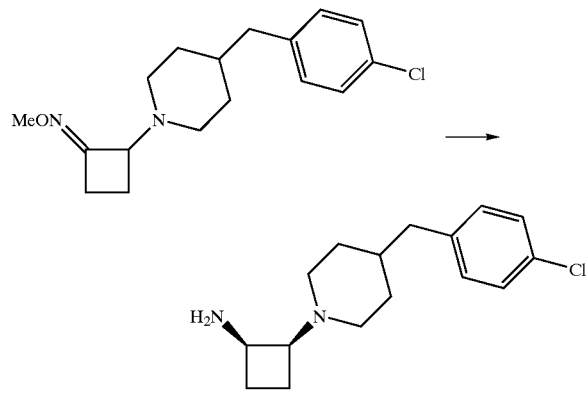

A solution of (±)-2-[4-(4-chlorobenzyl)piperidin-1-yl]-cyclobutanone O-methyl-oxime (438 mg, 1.43 mmol) in THF (13 mL) under Ar was treated dropwise with 1 M BH$_3$.THF complex in THF (8.6 mL, 8.6 mmol) and stirred at room temperature for 3 h and at 75° C. for 20 h. The reaction was cooled to 0° C. and treated carefully with 6 N HCl (1 mL) until the pH~2. The THF was evaporated and a solution of the residue in EtOH (9 mL) and 6 N HCl (1 mL) was stirred at 75° C. for 1 h. It was then allowed to cool to room temperature, basified with 8 N NaOH (4 mL) until the pH~10, diluted with H$_2$O (5 mL) to dissolve the resulting white precipitate, and concentrated. The residue was partitioned between CH$_2$Cl$_2$ and 1 N NaOH, the aqueous phase was extracted with CH$_2$Cl$_2$, and the extracts were dried and concentrated. Chromatography of the residue with 90:9.5:0.5–60:38:2 CH$_2$Cl$_2$:MeOH:NH$_4$OH gave, in order of elution, 70 mg of the desired product (80% pure by $^1$H NMR) as a colorless oil which was used without further purification, 48 mg (12%) of pure desired product as a colorless oil, and 125 mg of a mixture of desired product, stereoisomeric (±)-trans-2-[4-(4-chlorobenzyl)-piperidin-1-yl]-cyclobutylamine, and an unidentified impurity. Product: $^1$H NMR δ 1.19–1.70 (m, 8H), 1.89–2.05 (m, 3H), 2.50(d, J=6.9 Hz, 2H), 2.56 (m, 1H), 2.78 (m, 2H), 3.44 (m, 1H), 7.06 (m, 2H), 7.23 (m, 2H); $^{13}$C NMR δ 24.39, 25.56, 31.63, 31.76, 38.01, 42.61, 49.17, 49.63, 51.74, 62.51, 128.25, 130.42, 131.50, 139.16; MS m/z 279.2 (M+1)$^+$.

Preparation 7: Preparation of 4-(4-chlorobenzyl)-piperidine

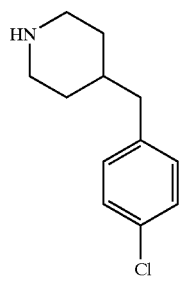

Step A: Preparation of 4-(4-Chloro-benzylidene)-piperidine-1-carboxylic acid tert-butyl ester

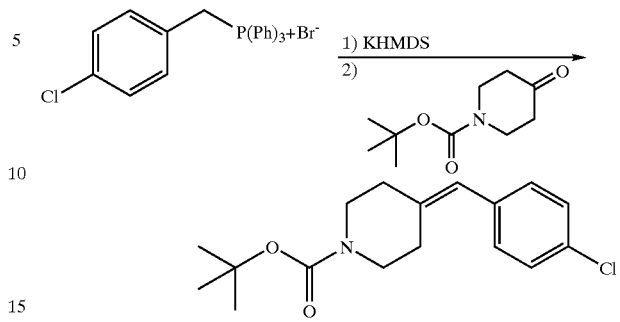

The phosphorium salt (10 g) was taken up in THF and placed in an ice bath. The KHMDS (42 mL) was added slowly, the ice bath was removed, and the reaction was stirred for 45 minutes at room temperature. The reaction solution was then cooled to −78° C. and the ketone (4.2 g) was added slowly. The reaction was stirred for 30 minutes, the cooling bath was removed, and the reaction was stirred overnight at room temperature. The reaction solution was poured into a saturated NH$_4$Cl (100 mL) solution, the layers were separated, the aqueous layer was washed twice with EtOAc, the organic layers were combined, dried (MgSO$_4$), and concentrated to ~40 mL. The solution was diluted with hexane and filtered to remove the majority of the Ph$_3$PO. Chromatography of the crude product with 20:1–10:1 hexane:EtOAc gave the product as a colorless oil (4.7 g).

Step B: Preparation of 4-(4-Chloro-benzyl)-piperidine-1-carboxylic acid tert-butyl ester

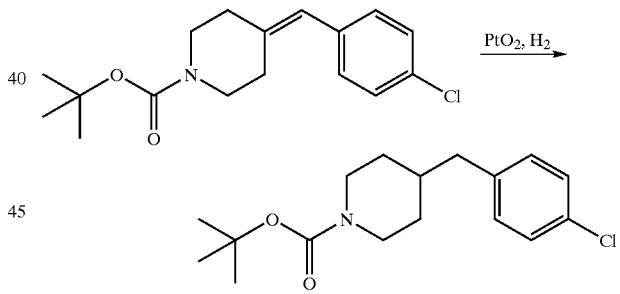

The protected piperidine (10 g) was dissolved in EtOAc (100 mL), the PtO$_2$ was added, and the mixture was stirred rapidly under H$_2$ for 3 hours. The mixture was filtered through celite and concentrated. The crude product was taken up in hot hexane, filtered and allowed to crystallize. The product was recrystallized with hot hexane to yield the clean product (8.0 g). Additional product was isolated form the mother liquor.

Step C: Preparation of 4-(4Chlorobenzyl)piperidine

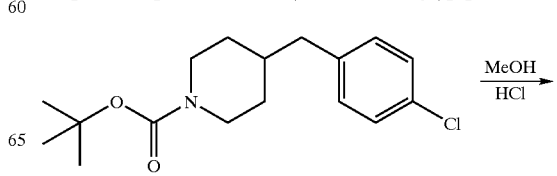

-continued

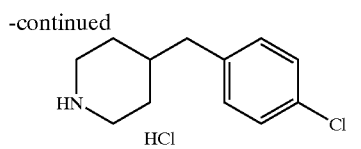

Methanol (400 mL) was placed in an ice bath and AcCl (60 mL) was added. After the addition was completed the solution was stirred at room temperature for one hour. The protected piperidine (62.8 g) was added and the solution was stirred at room temperature overnight. The reaction solution was concentrated to ~70 mL (when product first started to precipitate out), diluted with ether (500 mL), and the product was collected by filtration (44.9 g). An additional 3.1 g of the product was collected from the mother liquor.

Example 1

Preparation of (±)-trans-1-{2-[4-(4-chlorobenzyl)piperidin-1-yl]-cyclohexyl}-3-(3,4,5-trimethoxyphenyl)urea

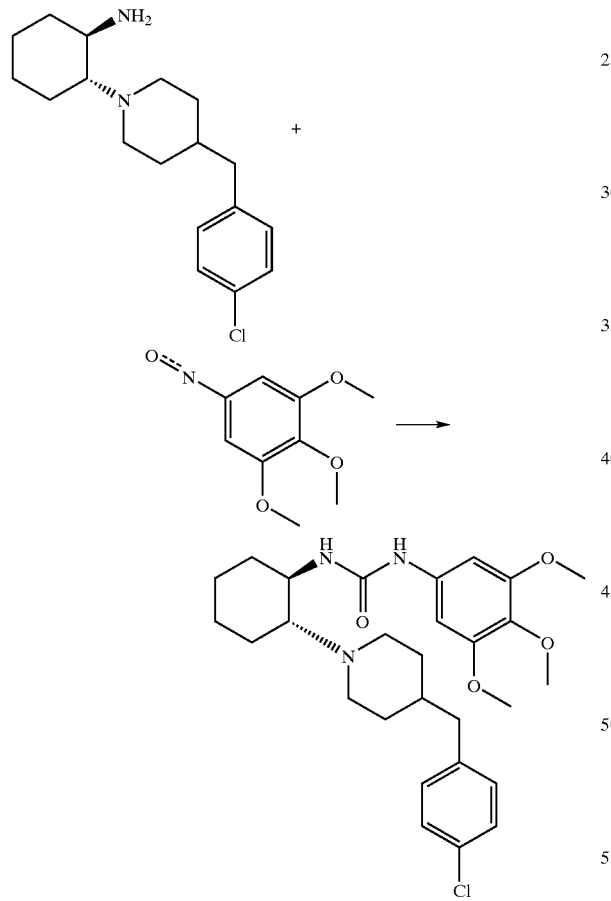

Following General Procedure C, (±)-trans-2-[4-(4-chlorobenzyl)piperidin-1-yl]-cyclohexylamine (56 mg, 0.18 mmol) and 5-isocyanato-1,2,3-trimethoxybenzene (76 mg, 0.36 mmol) were coupled in $CH_2Cl_2$ (1 mL) and DMF (1 mL) at room temperature for 1.5 h. After the combined extracts were washed with $H_2O$, dried and concentrated, preparative TLC with 95:4.75:0.25 $CH_2Cl_2$:MeOH:$NH_4OH$ followed by 90:9.5:0.5 $CH_2Cl_2$:MeOH:$NH_4OH$ and subsequent preparative TLC with 93:6.65:0.35 $CH_2Cl_2$:MeOH:$NH_4OH$ gave the product (52 mg, 55%) as a grey solid: mp 196.9–200.0° C.; IR 1670, 1606, 1545, 1505 cm$^{-1}$; $^1$H NMR [(CD$_3$)$_2$SO, 87° C.] δ 1.00–1.25 (m, 6H), 1.38–1.63 (m, 4H), 1.70 (m, 1H), 1.78 (m, 1H), 2.06 (m, 1H), 2.13–2.27 (m, 2H), 2.43 (d, J=6.8 Hz, 2H), 2.44 (m, 1H), 2.59 (m, 1H), 2.74 (m, 1H), 3.39 (m, 1H), 3.63 (s, 3H), 3.73 (s, 6H), 5.69 (d, J=5.3 Hz, 1H), 6.75 (s, 2H), 7.12 (m, 2H), 7.24 (m, 2H), 8.28 (s, 1H); MS m/z 516 (M+H)$^+$.

Example 2

Preparation of (±)-trans-N-{2-[4-(4-chlorobenzyl)piperidin-1-yl]-cyclohexyl}-4-methanesulfonylbenzamide

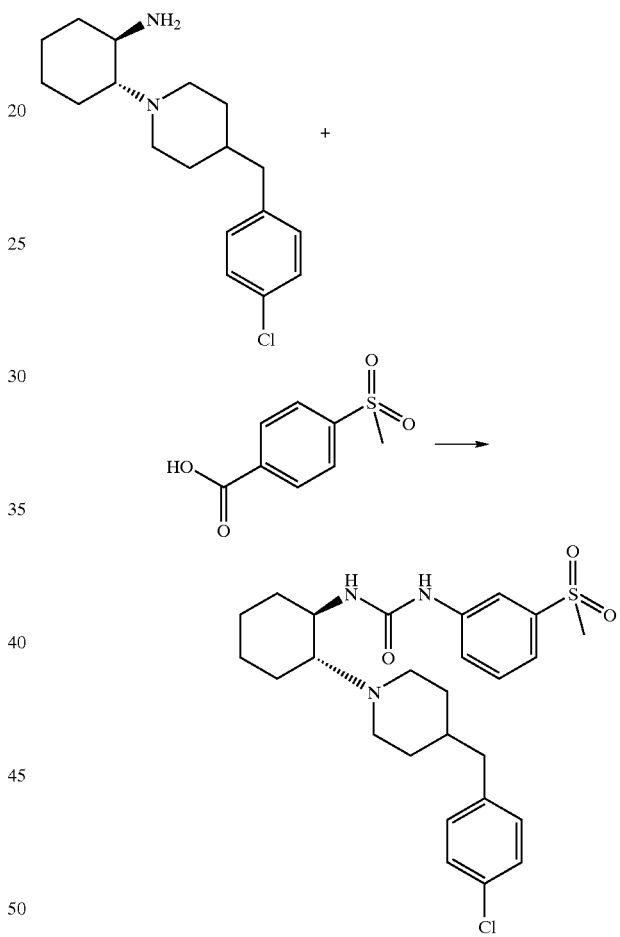

Following General Procedure E, (±)-trans-2-[4-(4-chlorobenzyl)piperidin-1-yl]-cyclohexylamine (92 mg, 0.30 mmol) and 4-methanesulfonyl-benzoic acid (72 mg, 0.36 mmol) were coupled in $CH_2Cl_2$ (2 mL) using HOBt (8 mg, 0.06 mmol) and DEC (86 mg, 0.45 mmol) at room temperature for 16 h. Purification of the crude product by preparative TLC with 93:6.65:0.35 $CH_2Cl_2$:MeOH:$NH_4OH$ gave the product (105 mg, 72%) as a tan solid: mp 184.5–186.7° C.; IR 1637 cm$^{-1}$; $^1$H NMR δ 0.94 (ddd, J=3.9, 11.7, 23.9 Hz, 1H), 1.09–1.93 (m, 12H), 2.05 (dt, J=2.4, 11.5 Hz, 1H), 2.35–2.74 (m, 6H), 3.10(m, 3H), 3.55–3.66 (m, 1H), 7.04 (m, 2H), 7.16 (m, 1H), 7.23 (m, 2H), 7.95 (m, 2H), 8.04 (m, 2H); MS m/z 489 (M+H)$^+$. Anal. ($C_{26}H_{33}ClN_2O_3S$) H, N; C: calcd, 63.85; found, 60.83. HPLC purity: 99.4%.

Example 3

Preparation of (±)-trans-1-{2-[4-(4-chlorobenzyl) piperidin-1-yl]-cyclohexyl}-3-(3-methanesulfonyl-phenyl)urea hydrochloride

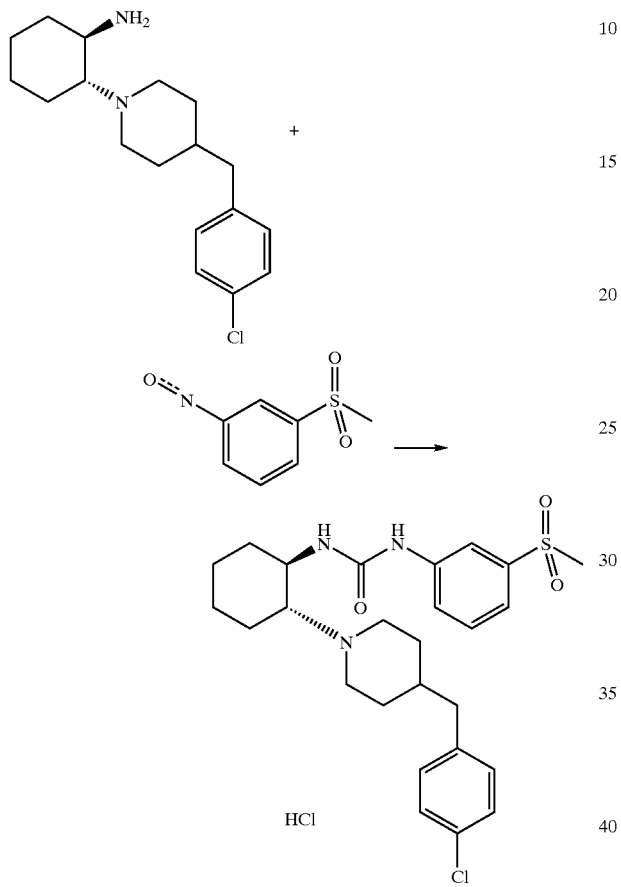

Example 4

Preparation of (±)-trans-1-{2-[4-(4-chlorobenzyl) piperidin-1-yl]-cyclopentyl}-3-(3,4,5-trimethoxyphenyl)urea hydrochloride

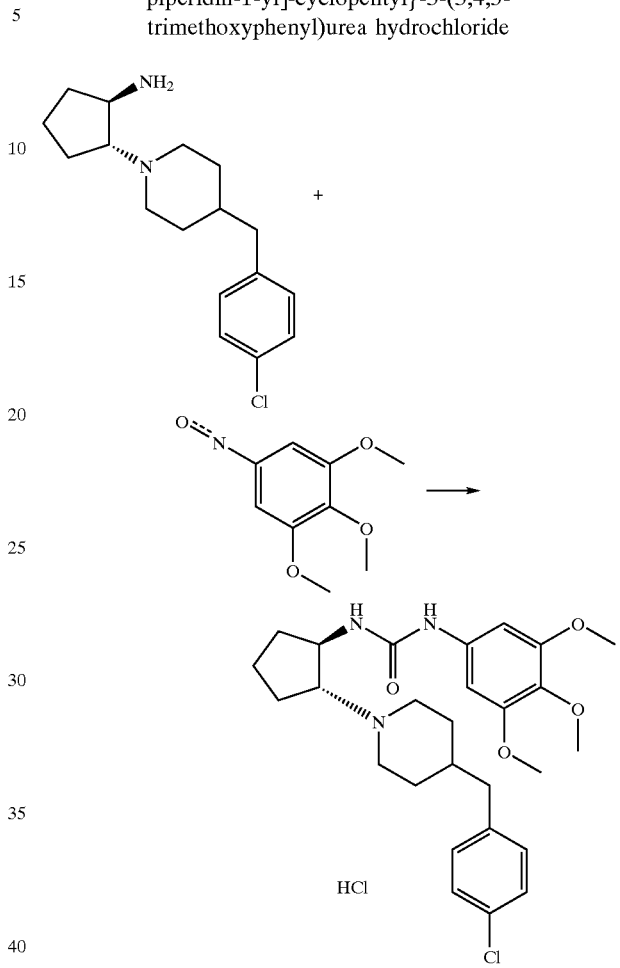

A solution of triphosgene (60 mg, 0.2 mmol) in CH$_2$Cl$_2$ (3 mL) was treated with a solution of 3-methanesulfonyl-phenylamine (120 mg, 0.7 mmol) and Et$_3$N (125 µL, 0.90 mmol) in CH$_2$Cl$_2$ (3 mL), stirred at 40° C. for 1.5 hours, allowed to cool to room temperature, and added in 2 portions during 30 min to a solution of (±)-trans-2-[4-(4-chlorobenzyl)piperidin-1-yl]-cyclohexylamine (88 mg, 0.29 mmol) in CH$_2$Cl$_2$ (1 mL). The reaction was stirred for 1 h and partitioned between CH$_2$Cl$_2$ and saturated NaHCO$_3$. The aqueous phase was extracted with CH$_2$Cl$_2$ and the extracts were dried and concentrated. Purification of the residue by preparative TLC with 95:4.75:0.25 CH$_2$Cl$_2$:MeOH:NH$_4$OH gave the free base (140 mg, 0.28 mmol) as a cream solid. A solution of the free base in CH$_2$Cl$_2$ was treated with 1 N HCl in Et$_2$O (0.5 mL, 0.5 mmol) and EtOAc, allowed to stand at room temperature for 3 d, at 0° C. overnight and at −20° C. overnight, and filtered to give the product (80 mg, 50%) as a white solid: mp 150.2–151.6° C.; MS m/z 504 (M+H)$^+$.

Following General Procedure D, (±)-trans-2-[4-(4-chlorobenzyl)piperidin-1-yl]-cyclopentylamine (250 mg, 0.85 mmol) and 5-isocyanato-1,2,3-trimethoxybenzene (355 mg, 1.70 mmol) were coupled in CH$_2$Cl$_2$ (5 mL) at room temperature for 1 h. After the combined extracts were dried (MgSO$_4$) and concentrated, chromatography of the residue with 95:4.75:0.25 CH$_2$Cl$_2$:MeOH:Et$_3$N and subsequent chromatography with 98:1.9:0.1 CH$_2$Cl$_2$:MeOH:Et$_3$N gave the free base (248 mg, 0.494 mmol) as a white foam. A solution of the free base (100 mg, 0.2 mmol) in CH$_2$Cl$_2$ was treated with 1 N HCl in Et$_2$O (0.5 mL, 0.5 mmol) and concentrated to give the product (104 mg, 56%) as a tan powder: mp 136.1–138.0° C.; IR 1690, 1607, 1555, 1507 cm$^{-1}$; $^1$H NMR [(CD$_3$)$_2$SO] δ 1.40–2.15 (m, 11H), 2.53 (m, 1.6H), 2.70 (m, 0.4H), 2.80–2.95 (m, 2H), 3.33–3.60 (m, 3H), 3.59 (s, 3H), 3.71 (s, 6H), 4.24–4.38 (m, 1H), 6.74 (s, 1.6H), 6.77 (s, 0.4H), 6.85 (d, J=8.2 Hz, 0.8H), 6.91 (m, 0.2H), 7.21 (m, 2H), 7.33 (m, 2H), 8.77 (s, 0.8H), 8.86 (s, 0.2H), 10.10–10.23 (m, 0.8H), 10.45 (m, 0.2H); $^{13}$C NMR [(CD$_3$)$_2$SO] δ 21.82, 26.88, 29.06, 32.57, 34.82, 40.68, 50.73, 51.01, 51.82, 56.02, 60.52, 71.47, 96.26, 128.51, 131.07, 131.27, 132.61, 136.25, 138.62, 153.10, 155.10; MS m/z 502 (M+H)$^+$.

Example 5

Preparation of (±)-trans-1-{4-[4-(4-chlorobenzyl)piperidin-1-yl]-tetrahydrofuran-3-yl}-3-(3,4,5-trimethoxyphenyl)urea hydrochloride

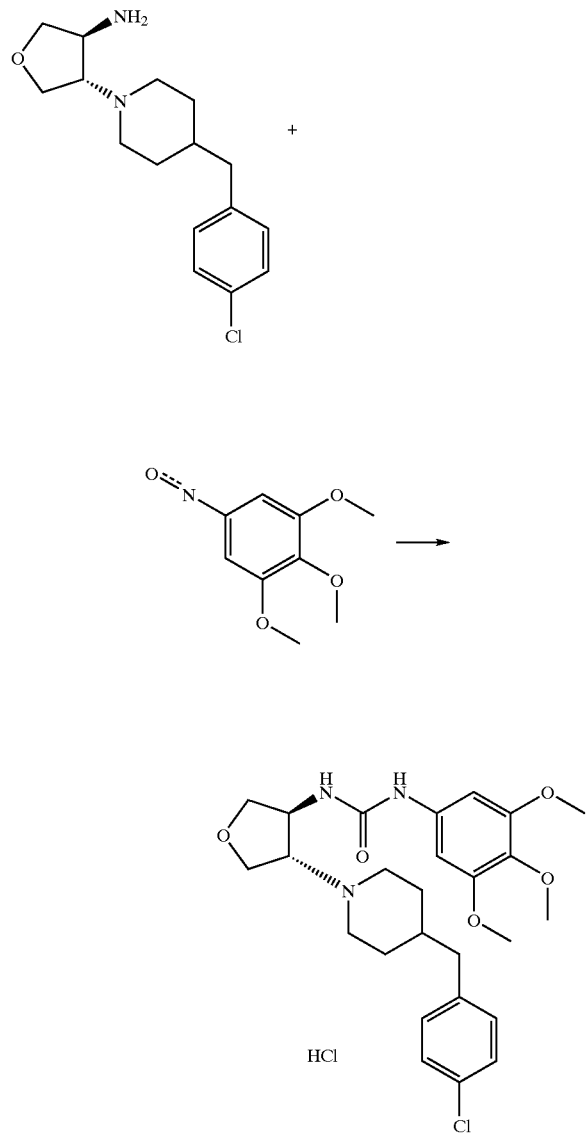

Following General Procedure D, (±)-trans-4-[4-(4-chlorobenzyl)piperidin-1-yl]-tetrahydrofuran-3-ylamine (3.03 g, 10.3 mmol) and 5-isocyanato-1,2,3-trimethoxybenzene (2.37 g, 11.3 mol) were coupled in CH₂Cl₂ (60 mL) at 0° C. for 1 h. Chromatography of the crude product with 1:1 hexanes:EtOAc to 100% EtOAc followed by 50:0.95:0.05–10:0.95:0.05 CH₂Cl₂:MeOH:NH₄OH gave the free base (4.62 g, 9.2 mmol) as a white foam. A solution of the free base (3.62 g, 7.2 mmol) in CH₂Cl₂ was treated with 1 N HCl in Et₂O (10 mL, 10 mmol) and concentrated to give the product (3.61 g, 83%) as a white solid: mp 229.2–230.9° C.; IR 3273 (br), 2937, 1690, 1606, 1554, 1507 cm⁻¹; ¹H NMR [(CD₃)₂SO] δ 1.54–1.74 (m, 7H), 2.52 (m, 2H), 2.97 (m, 2H), 3.49–3.71 (m, 11H), 4.06 (m, 3H), 4.59 (m, 1H), 6.74 (s, 2H), 7.00 (d, J=7.6 Hz, 1H), 7.22 (m, 2H), 7.35 (m, 2H), 8.85 (s, 1H), 10.8 (br s, 1H); MS m/z 504 (M+H)⁺.

Step A: Preparation of (±)-trans-4-[4-(4-chlorobenzyl)piperidin-1-yl]-tetrahydrofuran-3-ol

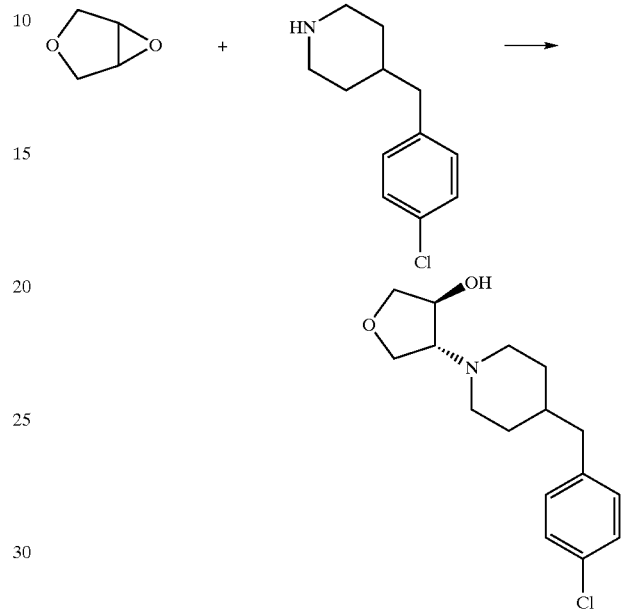

Following General Procedure A, 4-(4-chlorobenzyl)-piperidine (10.1 g, 48 mmol) was alkylated with 3,6-dioxabicyclo[3.1.0]hexane (24.7 g, 288 mol) (Barili, P. L.; Berti, G.; Mastrorilli, E.; *Tetrahedron* 1993, 49, 6263) in EtOH (75 mL) at 90–95° C. for 45 h. Chromatography of the crude product with CH₂Cl₂ followed by 99:0.95:0.05–95:4.75:0.25 CH₂Cl₂:MeOH:NH₄OH gave the product (10.7 g, 76%) as a white solid: ¹H NMR δ 1.21 (m, 2H), 1.51 (m, 1H), 1.62 (m, 2H), 2.03 (tt, J=2.5, 11.6 Hz, 2H), 2.19 (br, 1H), 2.50 (d, J=6.9 Hz, 2H), 2.73 (m, 2H), 3.08 (m, 1H), 3.61 (dd, J=6.9, 9.3 Hz, 1H), 3.70 (dd, J=3.1, 10.0 Hz, 1H), 3.93 (dd, J=5.7, 10.0 Hz, 1H), 4.05 (dd, J=7.0, 9.3 Hz, 1H), 4.33 (dt, J=3.0, 5.7 Hz, 1H), 7.05 (m, 2H), 7.24 (m, 2H); MS m/z 296.2 (M+H)⁺.

Step B: Preparation of (±)-trans-4-[4-(4-chlorobenzyl)piperidin-1-yl]-tetrahydrofuran-3-ylamine

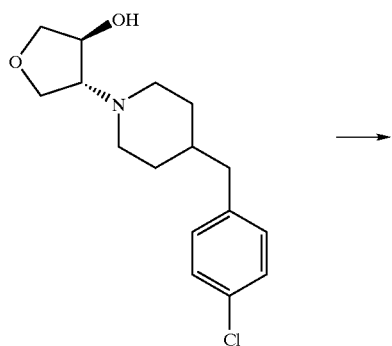

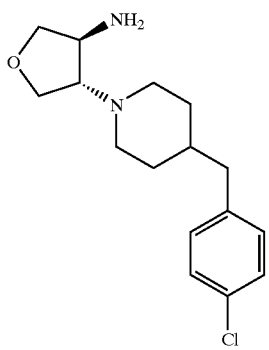

Following General Procedure B, (±)-trans-4-[4-(4-chlorobenzyl)piperidin-1-yl]-tetrahydrofuran-3-ol (10.65 g, 36 mmol) in CH$_2$Cl$_2$ (150 mL) was treated with Et$_3$N (10.2 mL, 72 mmol) and MeSO$_2$Cl (5.53 mL, 72 mol) for 1.25 h and the resultant product was heated in dioxane (205 mL) and NH$_4$OH (83 mL) for 4 h. Chromatography of the crude product with 100:1.9:0.1–100:19:1 CH$_2$Cl$_2$:MeOH:NH$_4$OH gave the product (9.58 g, 90%) as a yellow oil: $^1$H NMR δ 1.21–1.68 (m, 7H), 2.01 (m, 2H), 2.50 (d, J=6.9 Hz, 2H), 2.58 (dt, J=3.4, 6.8 Hz, 2H), 2.72 (m, 1H), 3.06 (m, 1H), 3.50 (m, 2H), 3.64 (dd, J=6.5, 9.3 Hz, 1H), 3.99 (m, 2H), 7.05 (m, 2H), 7.25 (m, 2H); MS m/z 295.2 (M+H)$^+$.

Example 6

Preparation of (±)-1-{(1R,2R,4S)-2-[4-(4-chlorobenzyl)piperidin-1-yl]-4-hydroxy-cyclopentyl}-3-(3,4,5-trimethoxyphenyl)urea

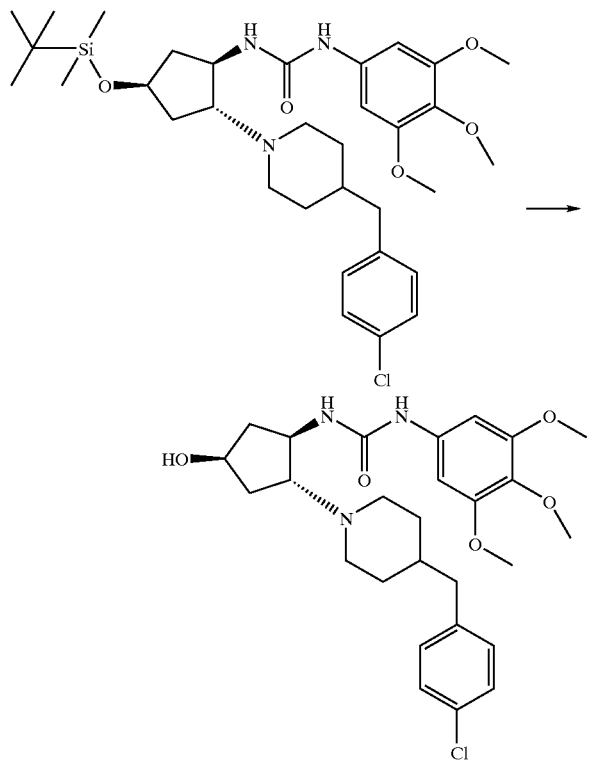

A solution of (1)-1-{(1R,2R,4S)-4-(tert-butyl-dimethylsilanyloxy)-2-[4-(4-chlorobenzyl)piperidin-1-yl]-cyclopentyl}-3-(3,4,5-trimethoxyphenyl)urea (605 mg, 0.96 mmol) in 1% HCl/EtOH (80 mL) was stirred at room temperature overnight. The EtOH was evaporated and the residue was partitioned between CH$_2$Cl$_2$ and saturated NaHCO$_3$. The aqueous phase was extracted with CH$_2$Cl$_2$ and the extracts were washed with brine, dried (MgSO$_4$) and concentrated. Chromatography of the residue with 95:4.75:0.25–90:9.5:0.5 CH$_2$Cl$_2$:MeOH:NH$_4$OH gave the product (440 mg, 89%) as a yellow solid: mp 98.7–102.0° C.; MS m/z 518 (M+H)$^+$.

Step A: Preparation of (±)-(1R,2R,4R)-4-(tert-butyl-dimethylsilanyloxy)-2-[4-(4-chlorobenzyl)piperidin-1-yl]-cyclopentanol Following General Procedure A, 4-(4-chlorobenzyl)-piperidine (741 mg, 3.53 mmol) was alkylated with cis-tert-butyl-dimethyl-(6-oxa-bicyclo[3.1.0]hex-3-yloxy)-silane (1.51 g, 7.06 mmol) (Asami, M. *Bull. Chem. Soc. Jpn.* 1990, 63, 1402) in EtOH (5 mL) at 90–95° C. for 82 h. Chromatography of the crude product with CH$_2$Cl$_2$ followed by 99:0.95:0.05–95:4.75:0.25 CH$_2$Cl$_2$:MeOH:NH$_4$OH gave the product (1.16 g, 78%) as a yellow foam: $^1$H NMR δ 0.00 (s, 6H), 0.81 (s, 9H), 1.19–1.99 (m, 12H), 2.44 (m, 2H), 2.80 (m, 2H), 3.13 (m, 1H), 4.07 (m, 1H), 4.28 (m, 1H), 6.99 (m, 2H), 7.17 (m, 2H); $^{13}$C NMR δ −4.55, −4.50, 18.3, 26.1, 32.1, 32.2, 38.1, 39.8, 42.3, 44.0, 52.1, 53.0, 74.0, 75.7, 75.8, 128.7, 130.8, 131.9, 139.2; MS m/z 424.2 (M+H)$^+$. HPLC purity 98.5%.

Step B: Preparation of (±)-(1R,2R,4S)-4-(tert-butyl-dimethylsilanyloxy)-2-[4-(4-chlorobenzyl)piperidin-1-yl]-cyclopentylamine

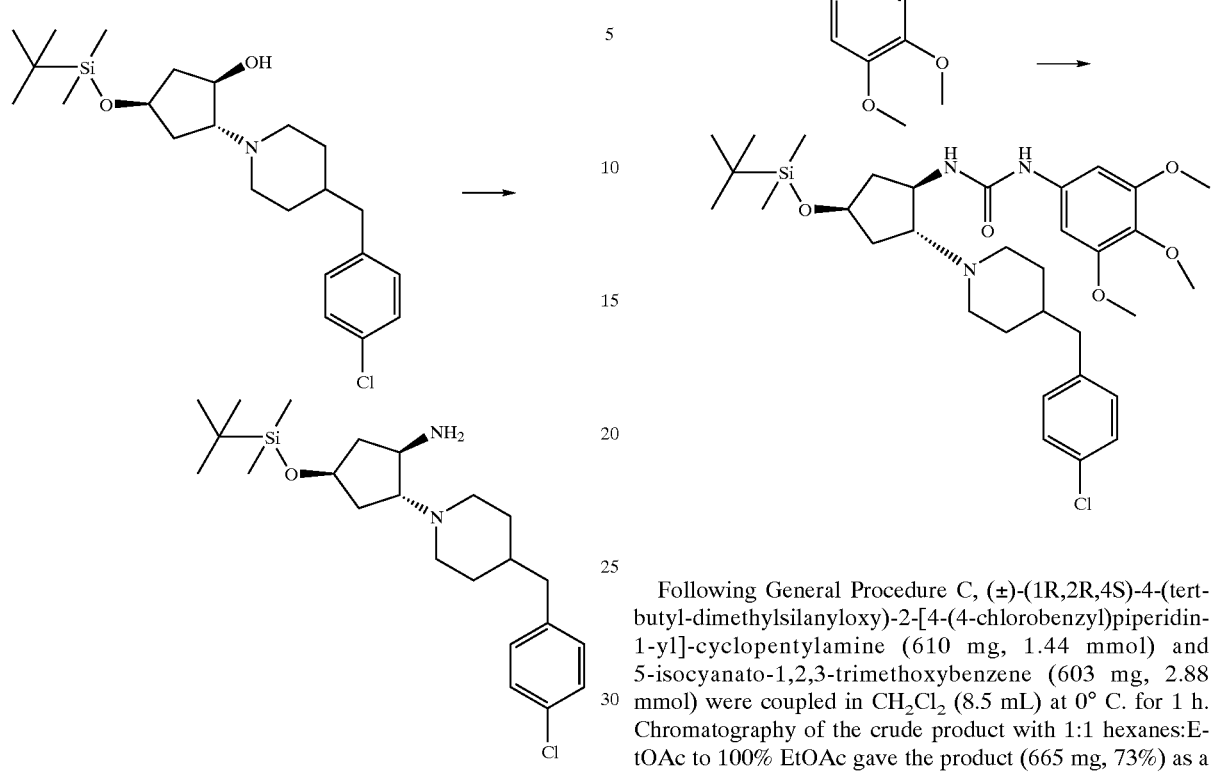

Following General Procedure B, (±)-(1R,2R,4R)-4-(tert-butyl-dimethylsilanyloxy)-2-[4-(4-chlorobenzyl)piperidin-1-yl]-cyclopentylamine (1.14 g, 2.68 mmol) in CH$_2$Cl$_2$ (10 mL) was treated with Et$_3$N (740 μL, 5.36 mmol) and MeSO$_2$Cl (410 μL, 5.36 mmol) for 2 h and the resultant product was heated in dioxane (15.6 mL) and NH$_4$OH (6.2 mL) for 6 h. Chromatography of the crude product with 98:1.9:0.1–80:19:1 CH$_2$Cl$_2$:MeOH:NH$_4$OH gave the product (620 mg, 55%) as a colorless oil: $^1$H NMR δ 0.00 (s, 6H), 0.83 (s, 9H), 1.15–1.32 (m, 2H), 1.40–2.11 (m, 11H), 2.45 (m, 2H), 2.60 (m, 1H), 2.80 (m, 1H), 3.02 (m, 1H), 3.14 (m, 1H), 4.20 (m, 1H), 7.02 (m, 2H), 7.19 (m, 2H); $^{13}$C NMR δ −4.85, −4.87, 17.9, 25.8, 32.0, 32.1, 37.8, 39.2, 42.4, 44.8, 51.0, 52.8, 54.8, 72.8, 75.8, 128.2, 130.4, 131.5, 139.0; MS m/z 423.2 (M+H)$^+$. HPLC purity 99.2%.

Step C: Preparation of (±)-1-{(1R,2R,4S)-4-(tert-butyl-dimethylsilanyloxy)-2-[4-(4-chlorobenzyl)piperidin-1-yl]-cyclopentyl}-3-(3,4,5-trimethoxyphenyl)urea Following General Procedure C, (±)-(1R,2R,4S)-4-(tert-butyl-dimethylsilanyloxy)-2-[4-(4-chlorobenzyl)piperidin-1-yl]-cyclopentylamine (610 mg, 1.44 mmol) and 5-isocyanato-1,2,3-trimethoxybenzene (603 mg, 2.88 mmol) were coupled in CH$_2$Cl$_2$ (8.5 mL) at 0° C. for 1 h. Chromatography of the crude product with 1:1 hexanes:EtOAc to 100% EtOAc gave the product (665 mg, 73%) as a yellow solid: mp 81.0–84.0° C.; IR 3379 (br), 2929, 1653, 1608, 1555, 1507 cm$^{-1}$; $^1$H NMR [(CD$_3$)$_2$SO] δ 0.03 (d, 6H), 0.86 (s, 9H), 1.12–1.69 (m, 8H), 1.95 (m, 2H), 2.18 (m, 1H), 2.46 (m, 2H), 2.79 (m, 3H), 3.58 (s, 3H), 3.71 (s, 6H), 3.93 (m, 1H), 4.16 (m, 1H), 5.94 (d, J=7.9 Hz, 1H), 6.70 (s, 2H), 7.16 (m, 2H), 7.30 (m, 2H), 8.43 (s, 1H); MS m/z 632 (M+H)$^+$.

Example 7

Preparation of (±)-1-{(1R,2R,4S)-2-[4-(4-chlorobenzyl)piperidin-1-yl]-4-hydroxycyclopentyl}-3-(3,4,5-trimethoxyphenyl)urea hydrochloride

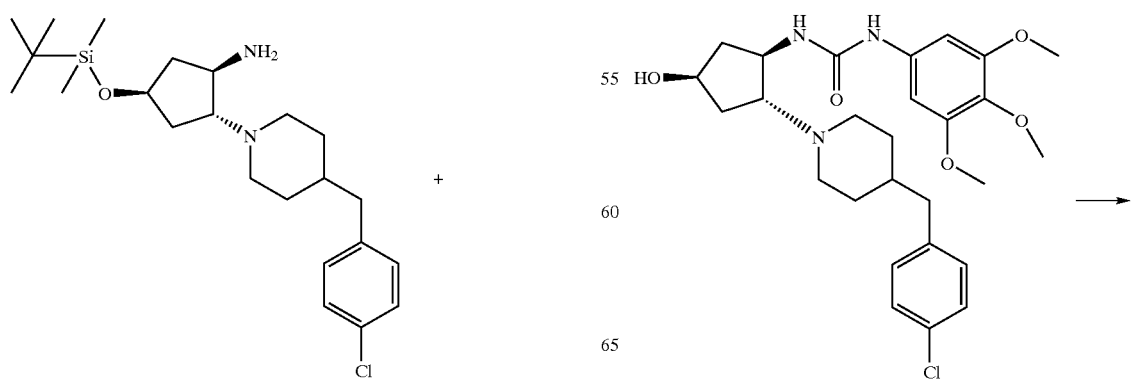

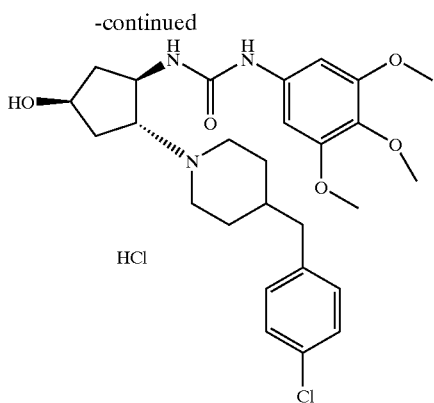

A solution of (±)-1-{(1R,2R,4S)-2-[4-(4-chlorobenzyl)piperidin-1-yl]-4-hydroxy-cyclopentyl}-3-(3,4,5-trimethoxyphenyl)urea (102 mg, 0.20 mmol) in CH$_2$Cl$_2$ was treated with 1 N HCl in Et$_2$O (0.5 mL, 0.5 mmol) and concentrated to give the product (110 mg, 100%) as a yellow solid: mp 137.0–143.0° C.; IR 3405 (br), 2935, 1685, 1606, 1554, 1507 cm$^{-1}$; $^1$H NMR [(CD$_3$)$_2$SO] δ 1.48–2.12 (m, 11H), 2.54 (m, 2H), 2.90 (m, 2H), 3.45 (m, 1H), 3.58 (s, 3H), 3.71 (s, 6H), 4.22 (m, 1H), 4.48 (m, 1H), 5.16 (br s, 1H), 6.42 (d, J=9.4 Hz, 1H), 6.70 (s, 2H), 7.21 (m, 2H), 7.34 (m, 2H), 10.19 (br s, 1H); MS m/z 518 (M+H)$^+$.

Example 8

Preparation of (±)-1-{(1R,2R,4S)-2-[4-(4-chlorobenzyl)piperidin-1-yl]-4-hydroxymethyl-cyclopentyl}-3-(3,4,5-trimethoxyphenyl)urea hydrochloride

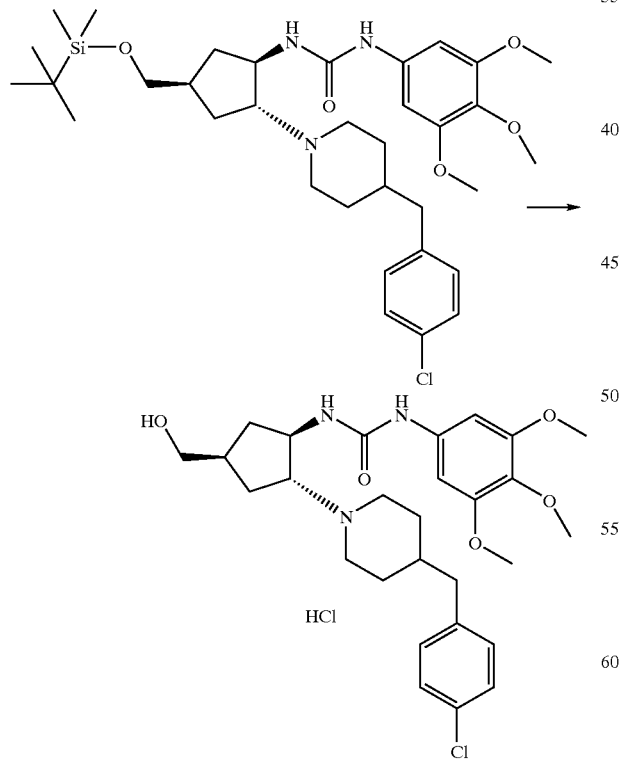

A solution of (±)-1-{(1R,2R,4S)-4-(tert-butyl-dimethylsilanyloxymethyl)-2-[4-(4-chlorobenzyl)piperidin-1-yl]-cyclopentyl}-3-(3,4,5-trimethoxyphenyl)urea (1.13 g, 1.75 mmol) in 1% HCl/EtOH (120 mL) was stirred at room temperature for 1 h. The EtOH was evaporated and the residue was partitioned between CH$_2$Cl$_2$ and saturated NaHCO$_3$. The aqueous phase was extracted with CH$_2$Cl$_2$ and the extracts were washed with brine, dried (MgSO$_4$) and concentrated. Chromatography of the residue with 95:4.75:0.25–90:9.5:0.5 CH$_2$Cl$_2$:MeOH:NH$_4$OH gave the free base (±)-1-{(1R,2R,4S)-2-[4-(4-chlorobenzyl)piperidin-1-yl]-4-hydroxymethyl-cyclopentyl}-3-(3,4,5-trimethoxyphenyl)urea (690 mg, 1.30 mmol) as a yellow solid. A solution of the free base (105 mg, 0.20 mmol) in CH$_2$Cl$_2$ was treated with 1 N HCl in Et$_2$O (0.5 mL, 0.5 mmol) and concentrated to give the product (112 mg, 74%) as a yellow solid: mp 138.0–143.0° C.; IR 3417 (br), 2936, 1687, 1606, 1554, 1507 cm$^{-1}$; $^1$H NMR [(CD$_3$)$_2$SO] δ 1.28–2.12 (m, 10H), 2.54 (m, 2H), 2.91 (m, 2H), 3.26–3.59 (m, 8H), 3.71 (s, 6H), 4.34 (m, 1H), 4.70 (br s, 1H), 6.66 (d, J=8.3 Hz, 1H), 6.73 (s, 2H), 7.21 (m, 2H), 7.32 (m, 2H), 8.78 (s, 1H), 10.13 (br s, 1H); MS m/z 532 (M+H)$^+$.

Step A: Preparation of (±)-(1R,2R,4R)-4-(tert-butyl-dimethylsilanyloxymethyl)-2-[4-(4-chlorobenzyl)piperidin-1-yl]-cyclopentol

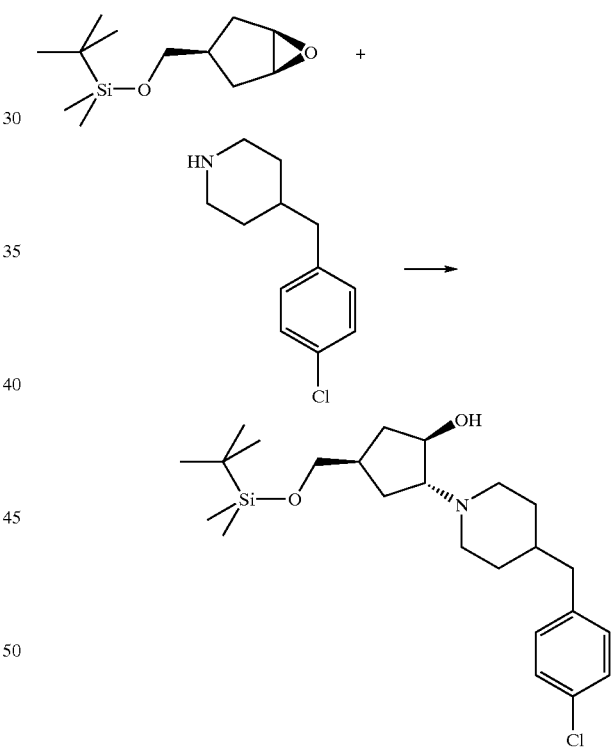

Following General Procedure A, 4-(4-chlorobenzyl)-piperidine (946 mg, 4.50 mmol) was alkylated with cis-tert-butyl-dimethyl-(6-oxa-bicyclo[3.1.0]hex-3-ylmethoxy)silane (1.13 g, 4.96 mmol) (Asami, M. Takahashi, J.; Inoue, S. *Tetrahedron Asymmetry* 1994, 5, 1649) in EtOH (4 mL) at 95° C. for 4.5 d. Chromatography of the crude product with CH$_2$Cl$_2$ followed by 99:0.95:0.05–95:4.75:0.25 CH$_2$Cl$_2$:MeOH:NH$_4$OH gave the product (1.38 g, 74%) as a brown oil: $^1$H NMR δ 0.00 (s, 6H), 0.84 (s, 9H), 1.34–1.86 (m, 8H), 2.08–2.31 (m, 5H), 2.48 (m, 2H), 2.80 (m, 1H), 3.13 (m, 1H), 3.28 (m, 1H), 3.48 (m, 2H), 4.28 (m, 1H), 7.00 (m, 2H), 7.19 (m, 2H); MS m/z 438.2 (M+H)$^+$.

53

Step B: Preparation of (±)-(1R,2R,4S)-4-(tert-butyl-dimethylsilanyloxymethyl)-2-[4-(4-chlorobenzyl)piperidin-1-yl]-cyclopentylamine

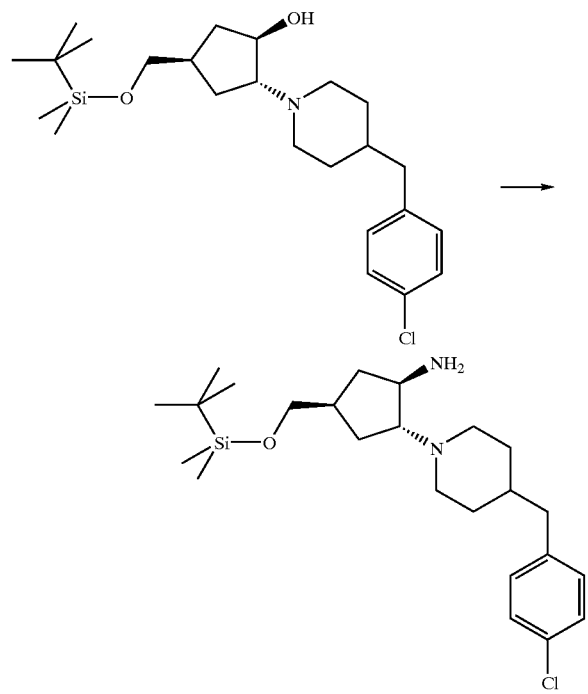

Following General Procedure B, a solution of (±)-(1R,2R,4R)-4-(tert-butyl-dimethylsilanyloxymethyl)-2-[4-(4-chlorobenzyl)piperidin-1-yl]-cyclopentanol (1.36 g, 3.0 mmol) in CH$_2$Cl$_2$ (15 mL) was treated with Et$_3$N (0.83 mL, 6.0 mmol) and MeSO$_2$Cl (0.46 mL, 6.0 mmol) for 1 h and the resultant product was heated in dioxane (17.2 mL) and NH$_4$OH (6.9 mL) for 2.5 h. Chromatography of the crude product with 98:1.9:0.1–90:9.5:0.5 CH$_2$Cl$_2$:MeOH:NH$_4$OH gave the product (780 mg, 57%) as a yellow oil: $^1$H NMR δ 0.00 (s, 6H), 0.85 (s, 9H), 0.92–1.70 (m, 11H), 1.96–2.21 (m, 3H), 2.44 (m, 3H), 2.83 (m, 2H), 3.12 (m, 1H), 3.43 (d, J=5.8 Hz, 2H), 7.02 (m, 2H), 7.19 (m, 2H); MS m/z 438.2 (M+H)$^+$. HPLC purity: 96.4%

Step C: Preparation of (±)-1-{(1R,2R,4S)-4-(tert-butyl-dimethylsilanyloxymethyl)-2-[4-(4-chlorobenzyl)piperidin-1-yl]-cyclopentyl}-3-(3,4,5-trimethoxyphenyl)urea

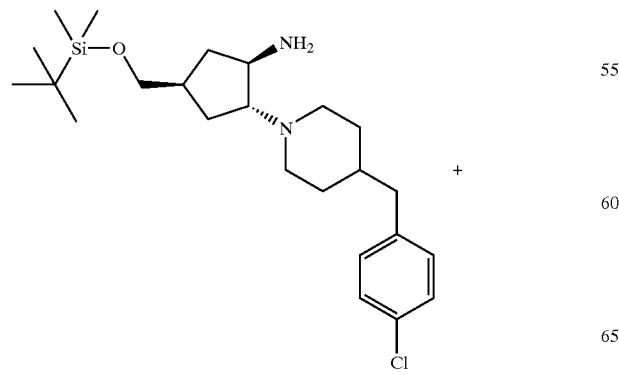

54

-continued

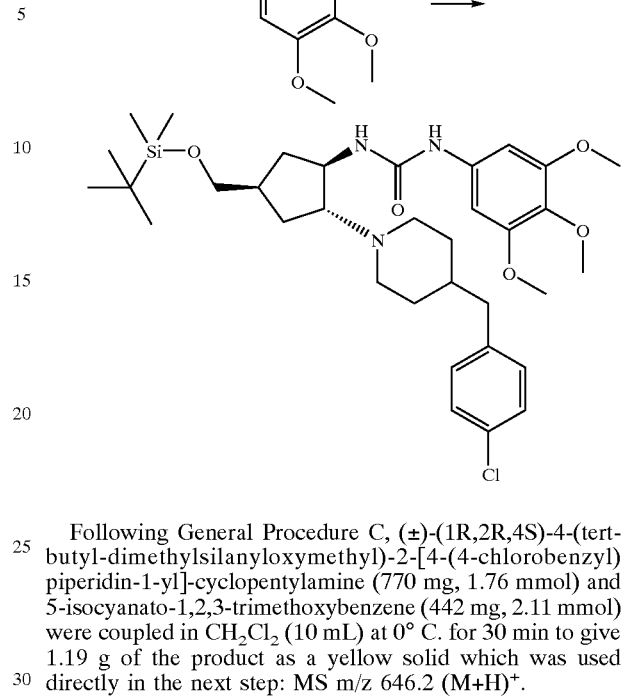

Following General Procedure C, (±)-(1R,2R,4S)-4-(tert-butyl-dimethylsilanyloxymethyl)-2-[4-(4-chlorobenzyl)piperidin-1-yl]-cyclopentylamine (770 mg, 1.76 mmol) and 5-isocyanato-1,2,3-trimethoxybenzene (442 mg, 2.11 mmol) were coupled in CH$_2$Cl$_2$ (10 mL) at 0° C. for 30 min to give 1.19 g of the product as a yellow solid which was used directly in the next step: MS m/z 646.2 (M+H)$^+$.

Example 9

Preparation of (±)-trans-1-{4-[4-(4-chlorobenzyl)piperidin-1-yl]-pyrrolidin-3-yl}-3-(3,4,5-trimethoxyphenyl)urea dihydrochloride

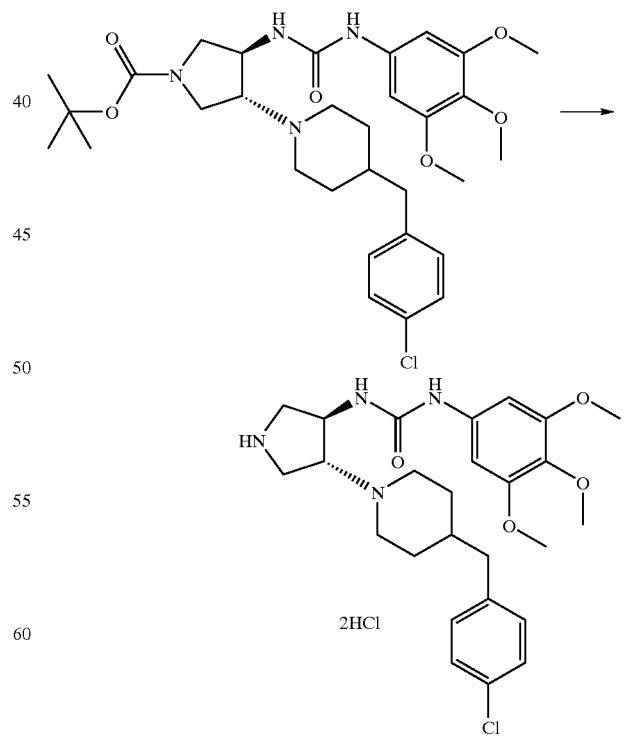

A solution of (±)-trans-3-[4-(4-chlorobenzyl)piperidin-1-yl]-4-[3-(3,4,5-trimethoxyphenyl)-ureido]-pyrrolidine-1- carboxylic acid tert-butyl ester (410 mg, 0.68 mmol) in 2% HCl/MeOH (70 mL) was stirred at room temperature overnight. The MeOH was evaporated and the residue was partitioned between CH$_2$Cl$_2$ and saturated NaHCO$_3$. The aqueous phase was extracted with CH$_2$Cl$_2$ and the extracts were washed with brine, dried (MgSO$_4$) and concentrated. Chromatography of the residue on alumina with CH$_2$Cl$_2$ followed by 50:0.95:0.05–5:0.95:0.05 CH$_2$Cl$_2$:MeOH:NH$_4$OH gave the free base (±)-trans-1-{4-[4-(4-chlorobenzyl)piperidin-1-yl]-pyrrolidin-3-yl}-3-(3,4,5-trimethoxyphenyl)urea (225 mg, 0.45 mmol) as a white solid. A solution of the free base (25 mg, 0.05 mmol) in CH$_2$Cl$_2$ was treated with 1 N HCl in Et$_2$O (0.15 mL, 0.15 mmol) and concentrated to give the product (27 mg, 68%) as a yellow solid: mp 157.0–170.0° C.; IR 3416 (br), 2935, 1686, 1606, 1554, 1507 cm$^{-1}$; $^1$H NMR [(CD$_3$)$_2$SO] δ 1.50–1.81 (m, 5H), 2.60 (d, J=6.6 Hz, 2H), 3.00–3.99 (m, 20H), 4.68 (m, 1H), 6.76 (s, 2H), 7.21 (m, 2H), 7.32 (m, 2H); MS m/z 504 (M+H)$^+$.

Step A: Preparation of (±)-trans-3-[4-(4-chlorobenzyl)piperidin-1-yl]-4-hydroxy-pyrrolidine-1-carboxylic acid tert-butyl ester

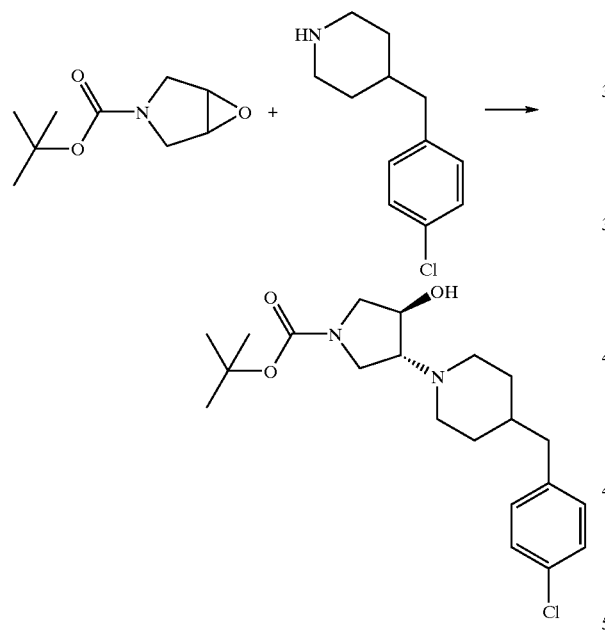

Following General Procedure A, 4-(4-chlorobenzyl)piperidine (1.72 g, 8.19 mmol) was alkylated with 6-oxa-3-aza-bicyclo[3.1.0]hexane-3-carboxylic acid tert-butyl ester (1.82 g, 9.82 mmol) [Okada, T.; Sato, H.; Tsuji, T.; Tsushima, T.; Nakai, H.; Yoshida, T.; Matsuura, S. *Chem. Pharm. Bull. Jpn.* 1993, 41, 132] in EtOH (5.5 mL) at 95° C. for 60 h. Chromatography of the crude product with CH$_2$Cl$_2$ followed by 100:0.95:0.05–30:0.95:0.05 CH$_2$Cl$_2$:MeOH:NH$_4$OH gave the product (1.85 g, 54%) as a yellow solid: mp 61.9–64.5° C.; IR 3421 (br) cm$^{-1}$; $^1$H NMR δ 1.26–1.69 (m, 14H), 1.94 (br s, 1H), 2.19 (m, 2H), 2.53 (d, J=6.9 Hz, 2H), 2.89 (m, 2H), 3.05–3.33 (m, 3H), 3.60–3.79 (m, 2H), 4.33 (m, 1H), 7.08 (m, 2H), 7.28 (m, 2H); MS m/z 395.2 (M+H)$^+$.

Step B: Preparation of (±)-trans-3-amino-4-[4-(4-chlorobenzyl)piperidin-1-yl]-pyrrolidine-1-carboxylic acid tert-butyl ester

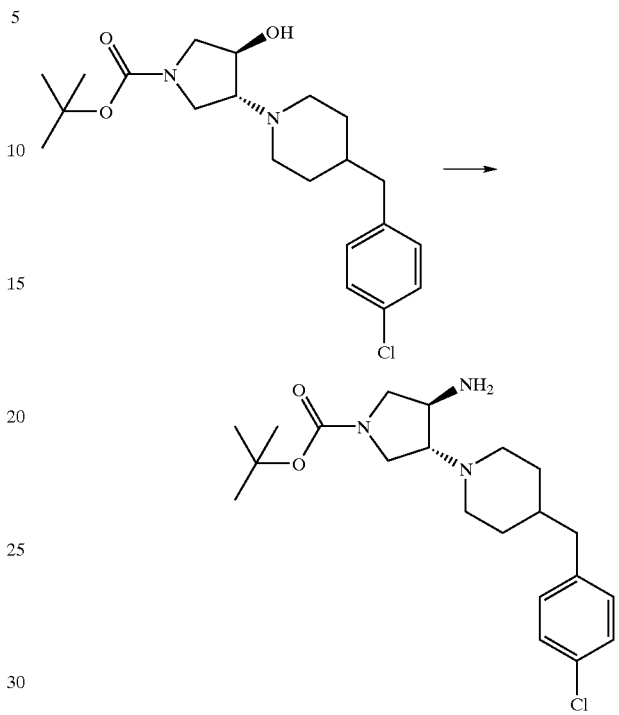

Following General Procedure B, a solution of (±)-trans-3-[4-(4-chlorobenzyl)piperidin-1-yl]-4-hydroxy-pyrrolidine-1-carboxylic acid tert-butyl ester (1.80 g, 4.56 mmol) in CH$_2$Cl$_2$ (20 mL) was treated with Et$_3$N (1.26 mL, 9.12 mmol) and MeSO$_2$Cl (0.70 mL, 9.12 mmol) for 1 h and the resultant product was heated in dioxane (26.0 mL) and NH$_4$OH (10.5 mL) for 6 h to give 1.91 g of the product (91% pure by HPLC) as a yellow oil which was used directly for the next step: $^1$H NMR δ 1.21–1.65 (m, 17H), 2.17 (m, 2H), 2.49 (d, J=7.0 Hz, 2H), 2.73–3.43 (m, 7H), 7.05 (m, 2H), 7.25 (m, 2H); MS m/z 394.2 (M+H)$^+$.

Step C: Preparation of (±)-trans-3-[4-(4-chlorobenzyl)piperidin-1-yl]-4-[3-(3,4,5-trimethoxyphenyl)ureido]-pyrrolidine-1-carboxylic acid tert-butyl ester

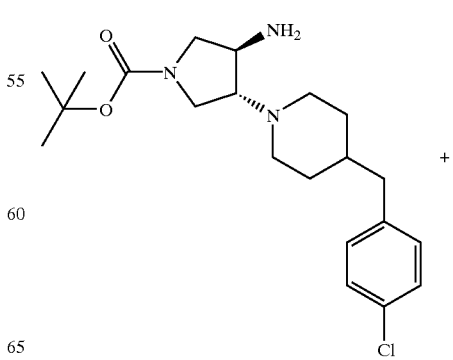

-continued

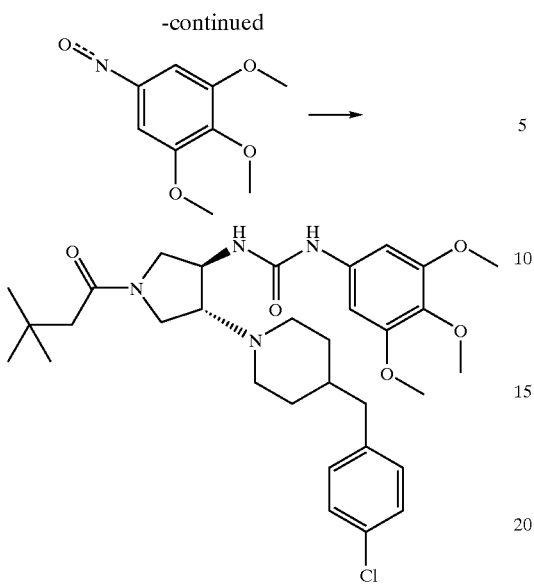

Following General Procedure C, (±)-trans-3-amino-4-[4-(4-chlorobenzyl)piperidin-1-yl]-pyrrolidine-1-carboxylic acid tert-butyl ester (394 mg, ~0.9 mmol) and 5-isocyanato-1,2,3-trimethoxybenzene (250 mg, 1.2 mmol) were coupled in CH$_2$Cl$_2$ (6.0 mL) at 0° C. for 1 h. Chromatography of the crude product with 1:1 hexanes:EtOAc to 100% EtOAc gave the product (445 mg, 77% from (±)-trans-3-[4-(4-chlorobenzyl)piperidin-1-yl]-4-hydroxy-pyrrolidine-1-carboxylic acid tert-butyl ester) as a white solid: mp 99.0–102.5° C.; IR 3371 (br), 2932, 1655, 1607, 1552, 1507 cm$^{-1}$; $^1$H NMR δ 1.17–1.80 (m, 14H), 2.18 (m, 2H), 2.48 (d, J=7.0 Hz, 2H), 2.95–3.51 (m, 8H), 3.81 (m, 9H), 4.32 (br, 1H), 5.30 (br, 1H), 6.61 (s, 2H), 7.02 (m, 2H), 7.20 (m, 2H); MS m/z 603.2 (M+H)$^+$.

Example 10

Preparation of (±)-cis-1-{2-[4-(4-chlorobenzyl)piperidin-1-yl]-cyclopentyl}-3-(3,4,5-trimethoxyphenyl)urea hydrochloride

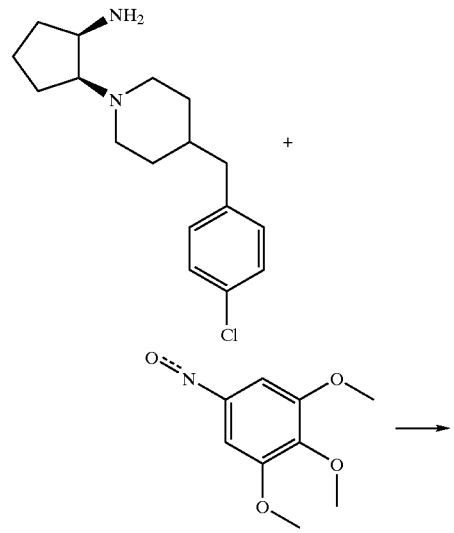

-continued

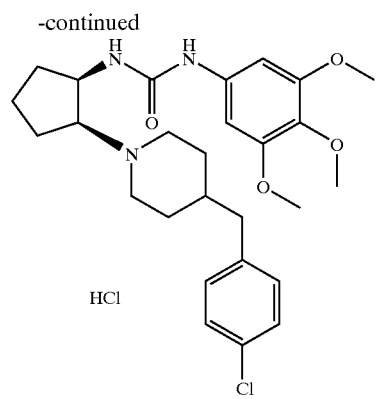

Following General Procedure D, a solution of (±)-cis-2-[4-(4-chlorobenzyl)piperidin-1-yl]-cyclopentylamine (110 mg, 0.38 mmol) in CH$_2$Cl$_2$ (2 mL) at 0° C. was treated with 5-isocyanato-1,2,3-trimethoxybenzene (98 mg, 0.47 mmol), stirred for 1 hour, and partitioned between CH$_2$Cl$_2$ and saturated NaHCO$_3$. The aqueous phase was extracted with CH$_2$Cl$_2$ and the extracts were dried and concentrated. Chromatography of the residue with EtOAc followed by 90:9.5:0.5 CH$_2$Cl$_2$:MeOH:NH$_4$OH and a subsequent chromatography with 1:3 hexanes:EtOAc to 100% EtOAc followed by 95:4.75:0.25 CH$_2$Cl$_2$:MeOH:NH$_4$OH gave the free base (190 mg, 0.38 mmol) as a colorless oil. A solution of the free base in CH$_2$Cl$_2$ (2 mL) was treated with 1 N HCl in Et$_2$O (1 mL, 1 mmol) and concentrated to give the product (193 mg, 96%) as a white solid: mp 117.5–122.5° C.; IR 1692, 1606, 1557, 1507 cm$^{-1}$; $^1$H NMR [(CD$_3$)$_2$SO] δ 1.33–2.15 (m, 11H), 2.51 (m, 2H), 2.64 (br d, J=7.8 Hz, 0.5H), 2.80–2.95 (m, 1.5H), 3.15–3.90 (m, 12H), 4.41 (m, 1H), 6.74 (s, 2H), 7.08–7.24 (m, 3H), 7.34 (m, 2H), 9.01 (br s, 0.7H), 9.06 (br s, 0.3H), 9.25–9.47 (m, 1H); HRMS (FAB) calcd for C$_{27}$H$_{37}$ClN$_3$O$_4$ 502.2473 (M+H)$^+$, found 502.2471.

Example 11

Preparation of (±)-cis-N-{2-[4-(4-chlorobenzyl)piperidin-1-yl]-cyclopentyl}-4-methanesulfonyl-benzamide hydrochloride

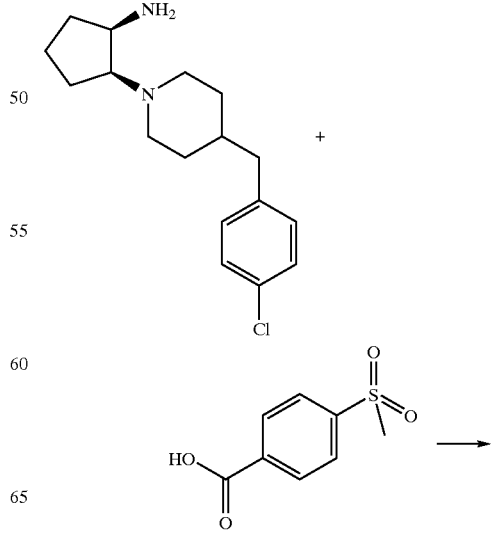

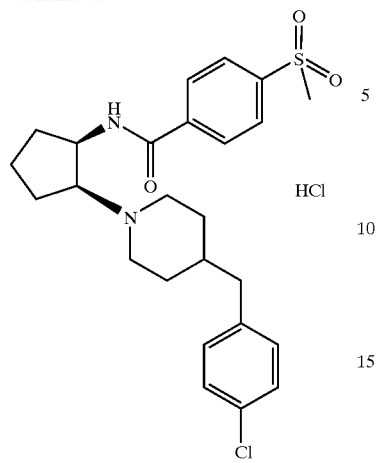

Following General Procedure F, (±)-cis-2-[4-(4-chlorobenzyl)piperidin-1-yl]-cyclopentylamine (105 mg, 0.358 mmol) and 4-methanesulfonyl-benzoic acid (86 mg, 0.43 mmol) were coupled in $CH_2Cl_2$ (2 mL) using HOBt (10 mg, 0.07 mmol) and DEC (138 mg, 0.719 mmol) at 0° C. for 2.5 h. Chromatography of the crude product with $CH_2Cl_2$ followed by 98:1.9:0.1 $CH_2Cl_2$:MeOH:$NH_4$OH gave the free base (176 mg, 0.36 mmol) as a colorless oil. A solution of the free base in $CH_2Cl_2$ was treated with 1 N HCl in $Et_2O$ (0.8 mL, 0.8 mmol) and concentrated to give the product (183 mg, 100%) as a cream foam: mp 125.3–131.9° C.; IR 1660 $cm^{-1}$; $^1$H NMR δ 1.63–2.23 (m, 11H), 2.56 (d, J=6.4 Hz, 2H), 2.56–2.85 (m, 2H), 3.05 (s, 0.3H), 3.06 (s, 2.7H), 3.20–3.34 (m, 1H), 3.60 (br d, J=11.7 Hz, 1H), 3.78 (br d, J=10.8 Hz, 1H), 4.93 (m, 1H), 7.00–7.11 (m, 2H), 7.25 (m, 2H), 8.03 (m, 2H), 8.50 (m, 2H), 8.95 (m, 0.1H), 9.06 (br d, J=8.3 Hz, 1H), 11.65–11.90 (m, 1H); $^{13}$C NMR δ 21.06, 26.85, 29.18, 29.38, 33.31, 36.77, 41.57, 44.76, 50.69, 53.67, 54.39, 68.88, 127.87, 129.08, 129.85, 130.64, 132.72, 137.61, 138.20, 143.57, 166.50; HRMS (FAB) calcd for $C_{25}H_{31}ClN_2O_3S$ 475.1822 (M+H)$^+$, found 475.1823.

Example 12

Preparation of (±)-trans-1-{1-acetyl-4-[4-(4-chlorobenzyl)piperidin-1-yl]-pyrrolidin-3-yl}-3-(3,4,5-trimethoxyphenyl)urea hydrochloride

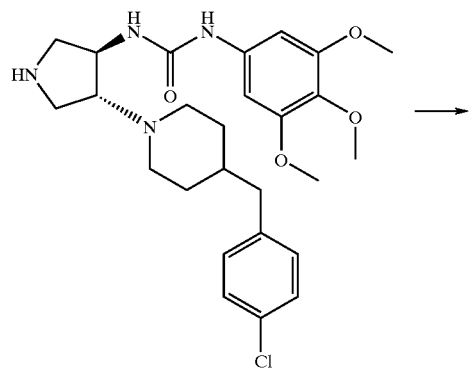

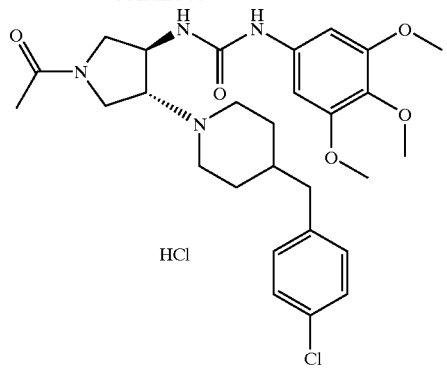

A solution of (±)-trans-1-{4-[4-(4-chlorobenzyl)piperidin-1-yl]-pyrrolidin-3-yl}-3-(3,4,5-trimethoxyphenyl)urea (80 mg, 0.16 mmol) and $Et_3N$ (26 μL, 0.19 mmol) in $CH_2Cl_2$ (1 mL) at 0° C. was treated dropwise with acetic anhydride (15 μL, 0.16 mmol), stirred at 0° C. for 10 min, and partitioned between $CH_2Cl_2$ and saturated $NaHCO_3$. The aqueous phase was extracted with $CH_2Cl_2$ and the extracts were dried and concentrated. Purification of the residue by preparative TLC with 10:0.95:0.05 $CH_2Cl_2$:MeOH:$NH_4$OH gave the free base as a white solid. A solution of the free base in $CH_2Cl_2$ was treated with 1 N HCl in $Et_2O$ (0.2 mL, 0.2 mmol) and concentrated to give the product (84 mg, 91%) as a tan solid: mp 155.0–161.0° C.; IR 3415 (br), 2936, 1691, 1608, 1554, 1508 $cm^{-1}$; $^1$H NMR [$(CD_3)_2$SO] δ 1.56–1.97 (m, 8H), 2.50–3.94 (m, 20H), 4.70 (m, 1H), 6.76 (s, 2H), 6.98 (m, 1H), 7.21 (m, 2H), 7.32 (m, 2H), 8.81 (s, 1H), 10.72 (s, 1H); MS m/z 545 (M+H)$^+$.

Example 13

Preparation of (±)-cis-1-{2-[4-(4-chlorobenzyl)piperidin-1-yl]-cyclohexyl}-3-(3,4,5-trimethoxyphenyl)urea hydrochloride

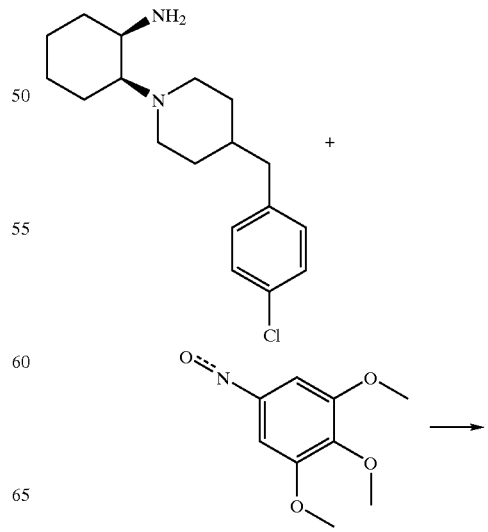

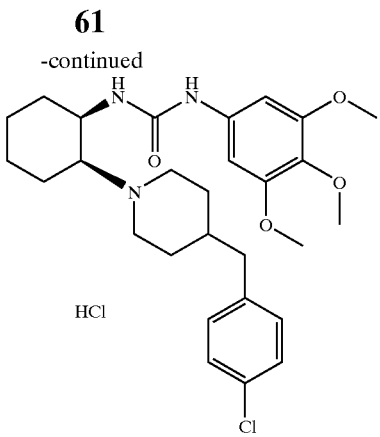

Following General Procedure D, (±)-cis-2-[4-(4-chlorobenzyl)piperidin-1-yl]-cyclohexylamine (53 mg, 0.17 mmol) and 5-isocyanato-1,2,3-trimethoxybenzene (40 mg, 0.19 mmol) were coupled in $CH_2Cl_2$ (1 mL) at 0° C. for 1 h. Purification of the crude product by preparative TLC with 93:6.65:0.35 $CH_2Cl_2$:MeOH:$NH_4OH$ gave the free base (75 mg, 0.15 mmol) as a tan foam. A solution of the free base (100 mg, 0.2 mmol) in $CH_2Cl_2$ was treated with 1 N HCl in $Et_2O$ (0.3 mL, 0.3 mmol) and concentrated to give the product (83 mg, 85%) as a tan foam: mp 120.1–137.3° C.; IR 1691, 1607, 1558, 1507 $cm^{-1}$; $^1H$ NMR ($CD_3OD$) δ 1.35–2.15 (m, 13H), 2.58 (d, J=6.4 Hz, 1.8H), 2.72 (m, 0.2H), 2.87–2.98 (m, 2H), 3.22 (m, 1H), 3.59 (m, 1H), 3.70 (s, 0.3H), 3.73 (s, 2.7H), 3.78 (s, 0.6H), 3.82 (s, 5.4H), 3.92 (m, 1H), 4.55 (m, 1H), 6.76 (s, 1.8H), 6.77 (s, 0.2H), 7.17 (m, 2H), 7.27 (m, 2H); MS m/z 516 (M+H)$^+$. Anal. ($C_{28}H_{39}Cl_2N_3O_4$·1.15$H_2O$) C, H, N.

Example 14

Preparation of (±)-cis-N-{2-[4-(4-chlorobenzyl)piperidin-1-yl]-cyclohexyl}-4-methanesulfonyl-benzamide hydrochloride

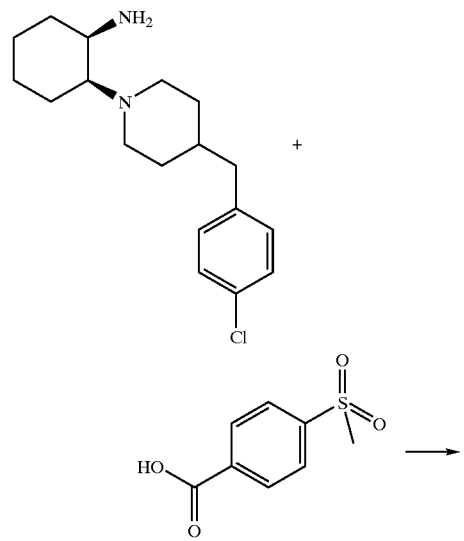

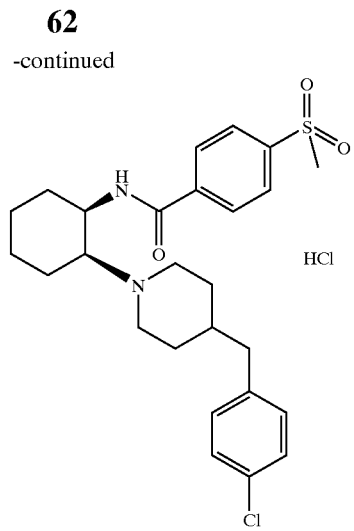

Following General Procedure F, (±)-cis-2-[4-(4-chlorobenzyl)piperidin-1-yl]-cyclohexylamine (30 mg, 0.10 mmol) and 4-methanesulfonyl-benzoic acid (24 mg, 0.12 mmol) were coupled in $CH_2Cl_2$ (1 mL) using HOBt (3 mg, 0.02 mmol) and DEC (30 mg, 0.16 mmol) at 0° C. for 2 h and at room temperature for 2 h. Purification of the crude product by preparative TLC with 90:9.5:0.5 $CH_2Cl_2$:MeOH:$NH_4OH$ gave the free base (46 mg, 0.09 mmol) as a white solid. A solution of the free base in $CH_2Cl_2$ was treated with 1 N HCl in $Et_2O$ (0.2 mL, 0.2 mmol) and concentrated to give the product (47 mg, 88%) as a cream solid: mp 123.7–149.4° C.; IR 1659 $cm^{-1}$; $^1H$ NMR ($CD_3OD$) δ 1.28–2.20 (m, 13H), 2.59 (d, J=6.2 Hz, 2H), 2.90–3.03 (m, 1H), 3.17 (s, 3H), 3.35 (m, 1H), 3.61 (m, 1H), 3.89 (m, 1H), 4.47–4.91 (m, 2H), 7.17 (d, J=8.3 Hz, 2H), 7.28 (m, 2H), 8.10 (m, 4H); MS m/z 489 (M+H)$^+$. Anal. ($C_{26}H_{34}Cl_2N_2O_3S$); calcd: C, 59.42; H, 6.52; N, 5.33; found: C, 55.39; H, 5.94; N, 4.88. HPLC purity: 98.6%.

Example 15

Preparation of (±)-trans-1-{4-[4-(4-chlorobenzyl)piperidin-1-yl]-1-methanesulfonyl-pyrrolidin-3-yl}-3-(3,4,5-trimethoxyphenyl)urea hydrochloride

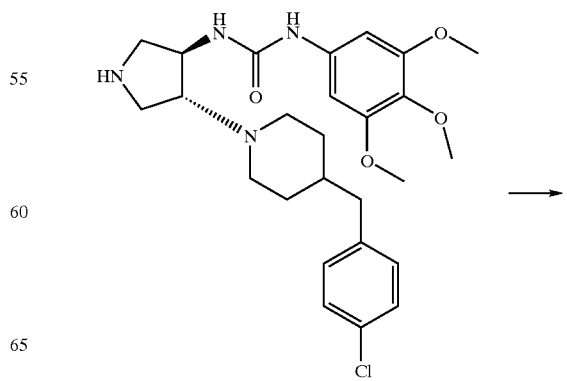

63

-continued

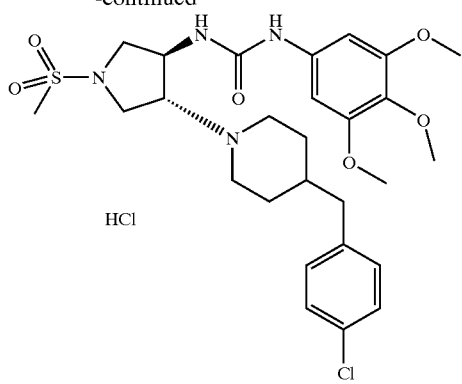

HCl

A solution of (±)-trans-1-{4-[4-(4-chlorobenzyl)piperidin-1-yl]-pyrrolidin-3-yl}-3-(3,4,5-trimethoxyphenyl)urea (78 mg, 0.15 mmol) and pyridine (13 µL, 0.15 mmol) in $CH_2Cl_2$ (2.5 mL) at 0° C. was treated dropwise with $MeSO_2Cl$ (12 µL, 0.15 mmol) and allowed to warm to room temperature slowly. The reaction was stirred for 1 hour, during which additional pyridine (3 µL, 0.04 mmol) and $MeSO_2Cl$ (3 µL, 0.04 mmol) was added, and partitioned between $CH_2Cl_2$ and 10% aqueous NaOH. The aqueous phase was extracted with $CH_2Cl_2$ and the extracts were washed with brine, dried and concentrated. Purification of the residue by preparative TLC with 10:0.95:0.05 $CH_2Cl_2$:MeOH:$NH_4OH$ gave the free base as a yellow semi-solid. A solution of the free base in $CH_2Cl_2$ was treated with 1 N HCl in $Et_2O$ (0.3 mL, 0.3 mmol) and concentrated to give the product (87 mg, 91%) as a tan solid: mp 148.0–158.0° C.; IR 3405 (br), 2933, 1691, 1608, 1554, 1507 cm$^{-1}$; $^1$H NMR [$(CD_3)_2SO$] δ 1.51–1.78 (m, 5H), 2.50 (m, 2H), 3.05–3.71 (m, 21H), 4.66 (m, 1H), 6.74 (s, 2H), 6.91 (br d, 1H), 7.21 (m, 2H), 7.34 (m, 2H), 8.84 (s, 1H), 10.75 (s, 1H); MS m/z 581 (M+H)$^+$. Anal. ($C_{27}H_{38}Cl_2N_4O_6S$·1.35$H_2O$) C, H, N.

64

-continued

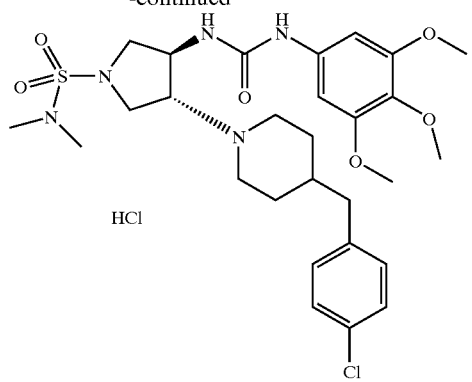

HCl

A solution of (±)-trans-1-{4-[4-(4-chlorobenzyl)piperidin-1-yl]-pyrrolidin-3-yl}-3-(3,4,5-trimethoxyphenyl)urea (80 mg, 0.16 mmol) and $Et_3N$ (33 µL, 0.24 mmol) in $CH_2Cl_2$ (2 mL) was treated with dimethylsulfamoyl chloride (21 µL, 0.20 mmol), stirred at room temperature for 20 hours, and partitioned between $CH_2Cl_2$ and saturated $NaHCO_3$. The aqueous phase was extracted with $CH_2Cl_2$ and the extracts were dried and concentrated. Purification of the residue by preparative TLC with 10:0.95:0.05 $CH_2Cl_2$:MeOH:$NH_4OH$ gave the free base as a white solid. A solution of the free base in $CH_2Cl_2$ was treated with 1 N HCl in $Et_2O$ (0.35 mL, 0.35 mmol) and concentrated to give the product (93 mg, 93%) as a white solid: mp 141.0–143.0° C.; IR 3378 (br), 2937, 1691, 1607, 1555, 1508 cm$^{-1}$; $^1$H NMR ([$(CD_3)_2SO$], $D_2O$ added, 87° C.) δ 1.53 (m, 2H), 1.86 (m, 3H), 2.58 (d, J=6.7 Hz, 2H), 2.84 (s, 6H), 3.07–3.86 (m, 18H), 4.60 (m, 1H), 6.74 (s, 2H), 7.22 (m, 2H), 7.34 (m, 2H); MS m/z 610 (M+H)$^+$. Anal. ($C_{28}H_{41}Cl_2N_5O_6S$·1$H_2O$) C, H, N.

Example 16

Preparation of (±)-trans-3-[4-(4-chlorobenzyl)piperidin-1-yl]-4-[3-(3,4,5-trimethoxyphenyl)-ureido]-pyrrolidine-1-sulfonic acid dimethylamide hydrochloride

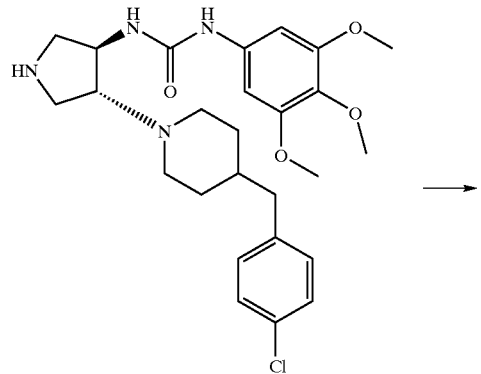

Example 17

Preparation of (±)-trans-3-[4-(4-chlorobenzyl)piperidin-1-yl]-4-[3-(3,4,5-trimethoxyphenyl)-ureido]-pyrrolidine-1-carboxylic acid dimethylamide hydrochloride

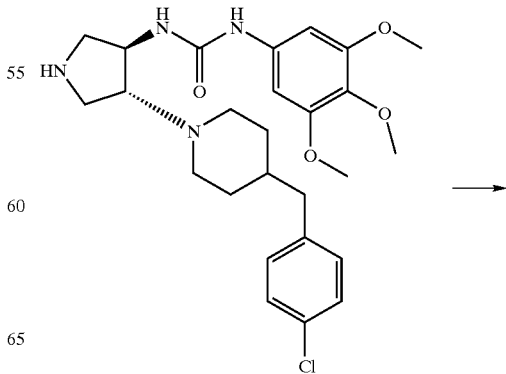

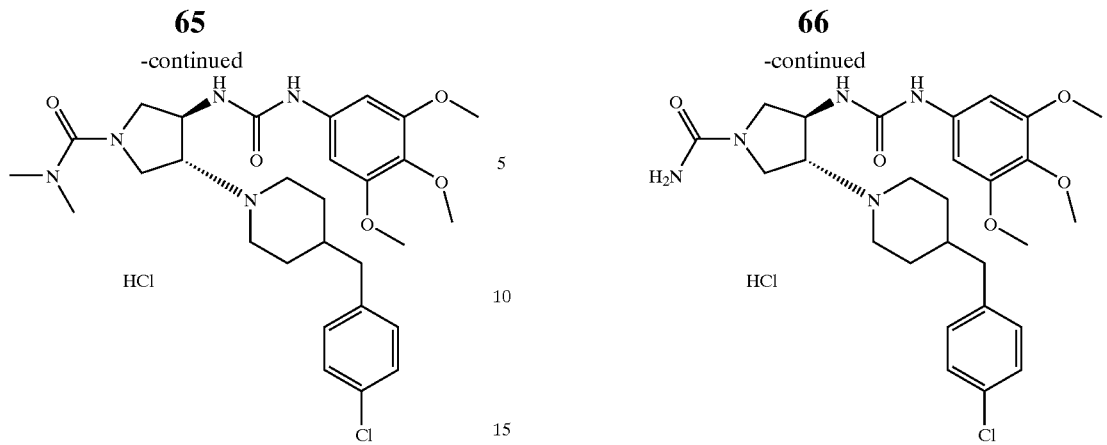

A solution of (±)-trans-1-{4-[4-(4-chlorobenzyl)piperidin-1-yl]-pyrrolidin-3-yl}-3-(3,4,5-trimethoxyphenyl)urea (90 mg, 0.18 mmol) and Et₃N (37 μL, 0.27 mmol) in CH₂Cl₂ (2 mL) at 0° C. was treated with dimethylcarbamyl chloride (20 μL, 0.22 mmol), allowed to warm to room temperature slowly, stirred for 75 min, and partitioned between CH₂Cl₂ and saturated NaHCO₃. The aqueous phase was extracted with CH₂Cl₂ and the extracts were dried and concentrated. Purification of the residue by preparative TLC with 6:0.95:0.05 CH₂Cl₂:MeOH:NH₄OH gave the free amine as a white solid. A solution of the free base in CH₂Cl₂ was treated with 1 N HCl in Et₂O (0.2 mL, 0.2 mmol) and concentrated to give the product (70 mg, 69%) as a yellow solid: mp 142.0–144.5° C.; IR 3272 (br), 2936, 1685, 1608, 1555, 1507 cm⁻¹; ¹H NMR ([(CD₃)₂SO], D₂O added, 87° C.) δ 1.54 (m, 2H), 1.84 (m, 3H), 2.54 (m, 2H), 2.82 (s, 6H), 3.05–3.76 (m, 18H), 4.55 (m, 1H), 6.76 (s, 2H), 7.22 (m, 2H), 7.34 (m, 2H); MS m/z 574 (M+H)⁺. Anal. (C₂₉H₄₁Cl₂N₅O₅·1.1H₂O) C, H, N.

A solution of (±)-trans-1-{4-[4-(4-chlorobenzyl)piperidin-1-yl]-pyrrolidin-3-yl}-3-(3,4,5-trimethoxyphenyl)urea (120 mg, 0.24 mmol) and NaOCN (36 mg, 0.55 mmol) in CH₃CN (2 mL) was treated with trifluoroacetic acid (36 μL, 0.48 mmol). The reaction mixture was stirred at room temperature for 20 h and concentrated. The residue was partitioned between CH₂Cl₂ and saturated NaHCO₃, the aqueous phase was extracted with CH₂Cl₂, and the extracts were dried and concentrated. Purification of the residue by preparative TLC with 5:0.95:0.05 CH₂Cl₂:MeOH:NH₄OH gave the free base as a white solid. A solution of the free base in CH₂Cl₂ was treated with 1 N HCl in Et₂O (0.2 mL, 0.2 mmol) and concentrated to give the product (70 mg, 54%) as a yellow solid: mp 158.0–162.0° C.; IR 3390 (br), 2935, 1654, 1605, 1554, 1508 cm⁻¹; ¹H NMR ([(CD₃)₂SO], D₂O added, 87° C.) δ 1.53–1.86 (m, 5H), 2.59 (d, J=6.8 Hz, 2H), 3.07–3.86 (m, 18H), 4.60 (m, 1H), 6.74 (s, 2H), 7.22 (m, 2H), 7.34 (m, 2H); MS m/z 546 (M+H)⁺. Anal. (C₂₇H₃₇Cl₂N₅O₅·1.1H₂O) C, H, N.

Example 18

Preparation of (±)-trans-3-[4-(4-chlorobenzyl)piperidin-1-yl]-4-[3-(3,4,5-trimethoxyphenyl)-ureido]-pyrrolidine-1-carboxylic acid amide hydrochloride

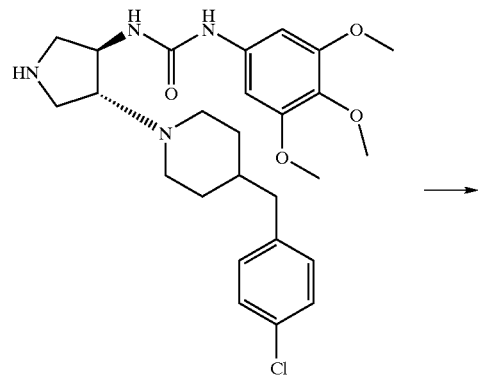

Example 19

Preparation of (±)-1-{(1R,2R,4S)-2-[4-(4-chlorobenzyl)piperidin-1-yl]-4-methoxymethyl-cyclopentyl}-3-(3,4,5-trimethoxyphenyl)urea hydrochloride

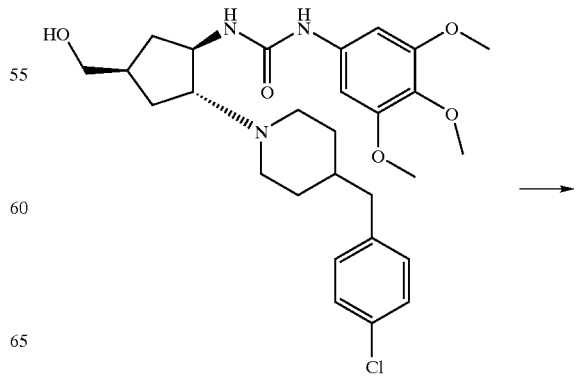

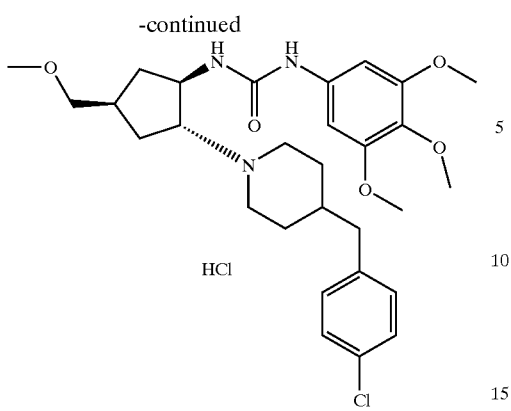

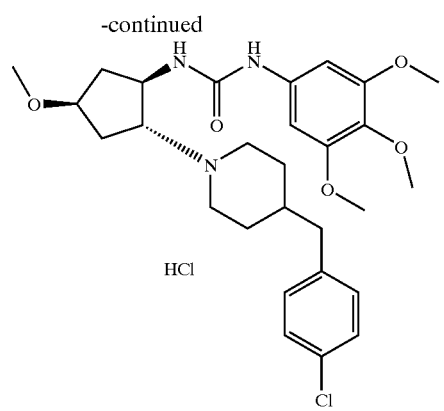

A mixture of (±)-1-{(1R,2R,4S)-2-[4-(4-chlorobenzyl)piperidin-1-yl]-4-hydroxymethyl-cyclopentyl}-3-(3,4,5-trimethoxyphenyl)urea (160 mg, 0.30 mmol) and silica gel (1.5 g) in CH$_2$Cl$_2$ (3 mL) at 0° C. was treated slowly with a fresh 0.5 N solution of diazomethane in Et$_2$O (60 mL, 30 mmol), allowed to warm to room temperature, stirred for 4 hours, and filtered. The silica gel was washed with methanol and the filtrate was concentrated. Purification of the residue by preparative TLC with 100:19:1 CH$_2$Cl$_2$:MeOH:NH$_4$OH followed by another preparative TLC with 100:9.5:0.5 CH$_2$Cl$_2$:MeOH:NH$_4$OH gave the free base (50 mg, 0.09 mmol) as a white foam. A solution of the free base in CH$_2$Cl$_2$ was treated with 1 N HCl in Et$_2$O (0.3 µL, 0.3 mmol) and concentrated to give the product (48 mg, 30%) as a white solid: mp 109.0–112.0° C.; IR 3420 (br), 2934, 1686, 1606, 1554, 1507 cm$^{-1}$; $^1$H NMR [(CD$_3$)$_2$SO] δ 1.32–2.28 (m, 10H), 2.54 (m, 2H), 2.91 (m, 2H), 3.26–3.50 (m, 8H), 3.59 (s, 3H), 3.71 (s, 6H), 4.33 (m, 1H), 6.62 (d, J=8.3 Hz, 1H), 6.77 (s, 2H), 7.20 (m, 2H), 7.34 (m, 2H), 8.75 (s, 1H), 10.14 (br s, 1H); MS m/z 546 (M+H)$^+$. Anal. (C$_{29}$H$_{41}$Cl$_2$N$_3$O$_5$·0.9H$_2$O) C, H, N.

A mixture of (±)-1-{(1R,2R,4S)-2-[4-(4-chlorobenzyl)piperidin-1-yl]-4-hydroxy-cyclopentyl}-3-(3,4,5-trimethoxyphenyl)urea (105 mg, 0.20 mmol) and silica gel (1.0 g) in CH$_2$Cl$_2$ (2 mL) at 0° C. was treated slowly with a fresh 0.5 N solution of diazomethane in Et$_2$O (45 mL, 22.5 mmol), allowed to warm to room temperature slowly, stirred for 4 hours, and filtered. The silica gel was washed with methanol and the filtrate was concentrated. Purification of the residue by preparative TLC with 100:19:1 CH$_2$Cl$_2$:MeOH:NH$_4$OH gave the free base (43 mg, 0.08 mmol) as a yellow solid. A solution of the free base in CH$_2$Cl$_2$ was treated with 1 N HCl in Et$_2$O (0.3 mL, 0.3 mmol) and concentrated to give the product (46 mg, 40%) as a tan solid: mp 112.5–119.5° C.; IR 3390 (br), 2935, 1686, 1607, 1555, 1506 cm$^{-1}$; $^1$H NMR [(CD$_3$)$_2$SO] δ 1.46–1.98 (m, 7H), 2.22 (m, 2H), 2.54 (m, 2H), 2.90 (m, 2H), 3.24 (s, 3H), 3.42 (m, 2H), 3.58–3.85 (m, 11H), 4.50 (m, 1H), 6.36 (d, J=9.1 Hz, 1H), 6.70 (s, 2H), 7.21 (m, 2H), 7.35 (m, 2H), 10.10 (s, 1H); MS m/z 532 (M+H)$^+$. Anal. (C$_{28}$H$_{39}$Cl$_2$N$_3$O$_5$·0.7H$_2$O) C, H, N.

Example 20

Preparation of (±)-1-{(1R,2R,4S)-2-[4-(4-chlorobenzyl)piperidin-1-yl]-4-methoxy-cyclopentyl}-3-(3,4,5-trimethoxyphenyl)urea hydrochloride

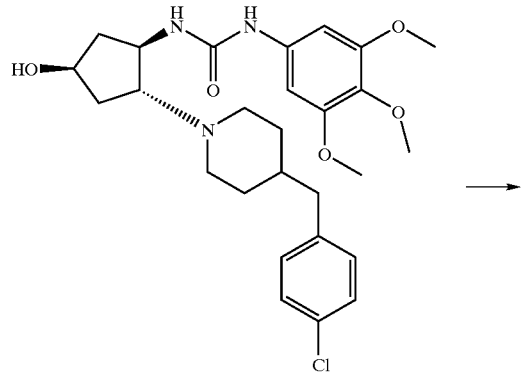

Example 21

Preparation of (±)-trans-2-{3-[4-(4-chlorobenzyl)piperidin-1-yl]-4-[3-(3,4,5-trimethoxyphenyl)-ureido]-pyrrolidin-1-yl}-acetamide dihydrochloride

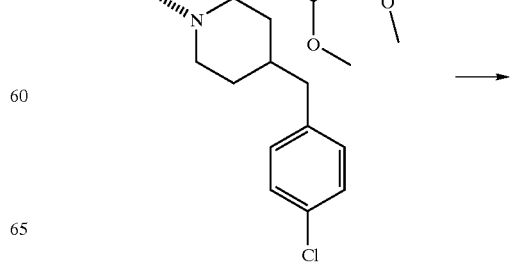

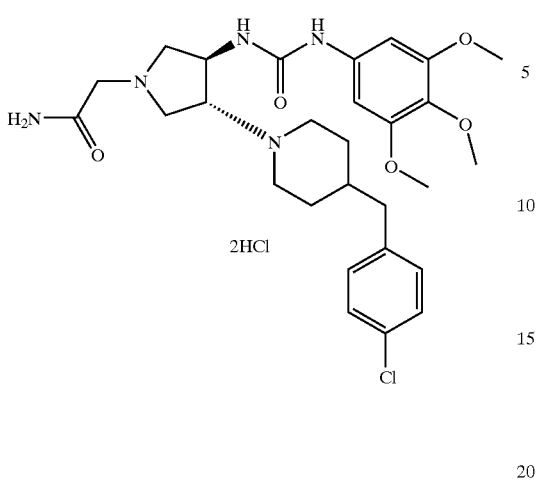

2HCl

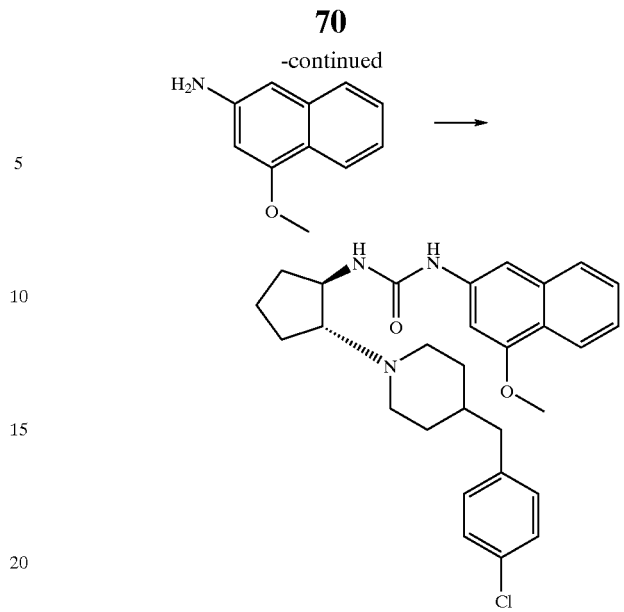

A solution of (±)-trans-1-{4-[4-(4-chlorobenzyl)piperidin-1-yl]-pyrrolidin-3-yl}-3-(3,4,5-trimethoxyphenyl)urea (90 mg, 0.18 mmol) in anhydrous DMF (2.5 mL) was treated successively with i-Pr₂NEt (47 µL, 0.27 mmol) and 2-iodoactamide (40 mg, 0.22 mmol), stirred at room temperature for 24 hours, and partitioned between CH₂Cl₂ and saturated NaHCO₃. The aqueous phase was extracted with CH₂Cl₂, and the extracts were washed with H₂O and brine, dried and concentrated. Purification of the residue by preparative TLC with 10:0.95:0.05 CH₂Cl₂:MeOH:NH₄OH gave the free amine as a yellow solid. A solution of the free base in CH₂Cl₂ was treated with 1 N HCl in Et₂O (0.3 mL, 0.3 mmol) and concentrated to give the product (54 mg, 50%) as a tan solid: mp 160.0–165.0° C.; IR 3414 (br), 2933, 1691, 1607, 1557, 1507 cm⁻¹; ¹H NMR [(CD₃)₂SO] δ 1.55–1.77 (m, 5H), 2.49 (m, 2H), 3.00–3.71 (m, 20H), 4.72 (br s, 1H), 6.76 (s, 2H), 7.01 (br d, 1H), 7.21 (m, 2H), 7.34 (m, 2H), 7.58 (br s, 1H), 7.83 (br s, 1H), 9.12 (br s, 1H); MS m/z 560 (M+H)⁺. Anal. (C₂₈H₄₀Cl₃N₅O₅.1.3H₂O) C, H, N.

Example 22

Preparation of (±)-trans-1-{2-[4-(4-chlorobenzyl)piperidin-1-yl]-cyclopentyl}-3-(4-methoxy-naphthalen-2-yl)urea

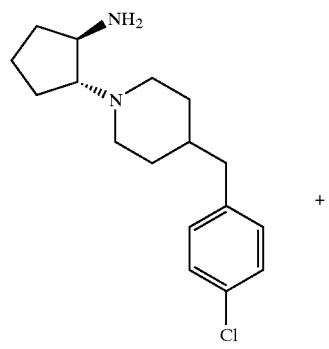

+

A solution of triphosgene (47 mg, 0.16 mmol) in CH₂Cl₂ (2 mL) was treated dropwise with a solution of (±)-trans-2-[4-(4-chlorobenzyl)piperidin-1-yl]-cyclopentylamine (140 mg, 0.48 mmol) and N,N-diisopropylethylamine (180 µL, 1.0 mmol) in CH₂Cl₂ (1 mL) and added to a solution of 4-methoxy-naphthalen-2-ylamine (83 mg, 0.48 mmol) and N,N-diisopropylethylamine (180 µL, 1.0 mmol) in CH₂Cl₂ (1 mL). The reaction was stirred for 4 hours, washed with 1 N KHSO₄, saturated NaHCO₃, and brine, dried, and concentrated. Purification of the residue by preparative TLC with 100:9.5:0.5 CH₂Cl₂:MeOH:NH₄OH gave the product (100 mg, 43%) as a yellow solid: mp 175–190° C.; MS m/z 492 (M+H)⁺.

Example 23

Preparation of (±)-trans-1-{4-[4-(4-chlorobenzyl)piperidin-1-yl]-1-(2-methanesulfonyl-ethyl)-pyrrolidin-3-yl}-3-(3,4,5-trimethoxyphenyl)urea dihydrochloride

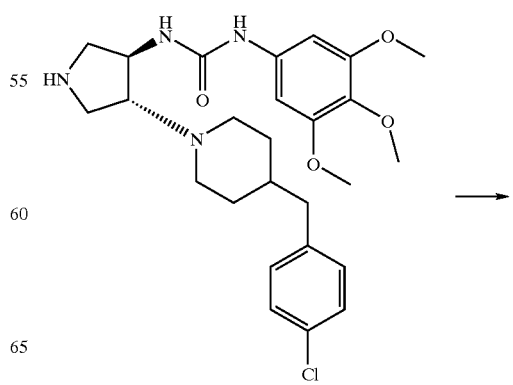

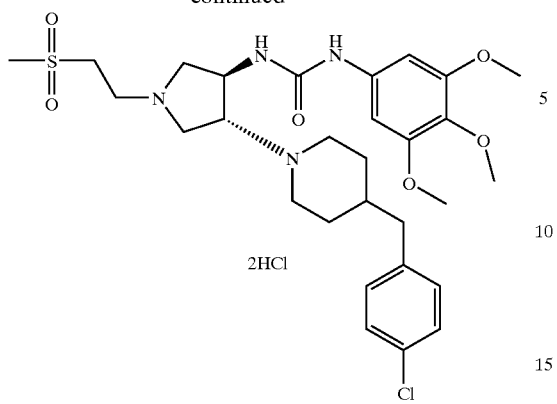

2HCl

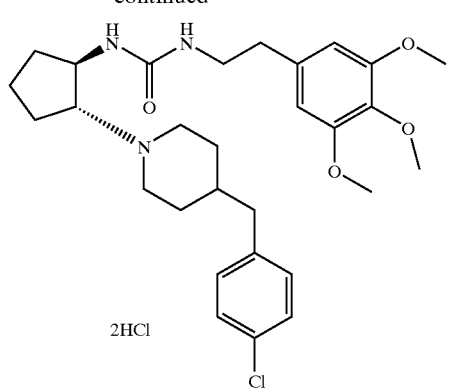

2HCl

A solution of (±)-trans-1-{4-[4-(4-chlorobenzyl) piperidin-1-yl]-pyrrolidin-3-yl}-3-(3,4,5-trimethoxyphenyl) urea (100 mg, 0.20 mmol) in MeOH (1 mL) was treated with methyl vinyl sulfone (18 μL, 0.21 mmol). The mixture was stirred at room temperature overnight and concentrated. Purification of the residue by preparative TLC with 7:0.95:0.05 CH$_2$Cl$_2$:MeOH:NH$_4$OH gave the free amine as a white solid. A solution of the free base in CH$_2$Cl$_2$ was treated with 1 N HCl in Et$_2$O (0.5 mL, 0.5 mmol) and concentrated to give the product (110 mg, 83%) as a white solid: mp 210.2–211.8° C.; IR 3422 (br), 2930, 1686, 1607, 1556, 1507 cm$^{-1}$; $^1$H NMR [(CD$_3$)$_2$SO] δ 1.54–1.77 (m, 5H), 2.51 (m, 2H), 3.05–3.71 (m, 25H), 4.71 (br s, 1H), 6.75 (s, 2H), 6.92 (br d, 1H), 7.21 (m, 2H), 7.34 (m, 2H), 9.01 (s, 1H); MS m/z 609 (M+H)$^+$. Anal. (C$_{29}$H$_{43}$Cl$_3$N$_4$O$_6$S.1.15H$_2$O) C, H, N.

Example 24

Preparation of (±)-trans-1-{2-[4-(4-chlorobenzyl) piperidin-1-yl]-cyclopentyl}-3-[2-(3,4,5-trimethoxyphenyl)-ethyl]urea hydrochloride

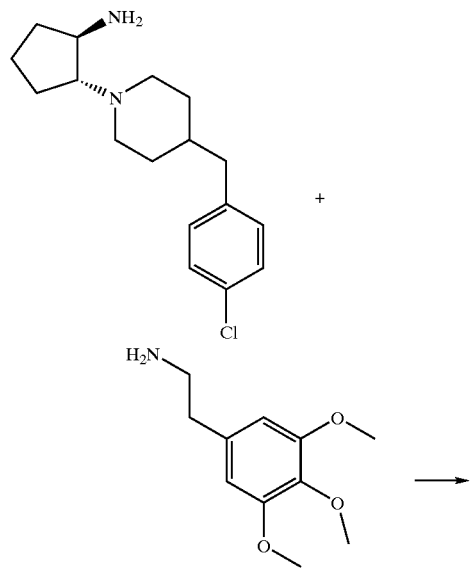

A solution of triphosgene (47 mg, 0.16 mmol) in CH$_2$Cl$_2$ (2 mL) was treated dropwise with a solution of (±)-trans-2-[4-(4-chlorobenzyl)piperidin-1-yl]-cyclopentylamine (140 mg, 0.48 mmol) and N,N-diisopropylethylamine (180 μL, 1.0 mmol) in CH$_2$Cl$_2$ (1 mL) and added to a solution of 2-(3,4,5-trimethoxyphenyl)-ethylamine (101 mg, 0.48 mmol) and N,N-diisopropylethylamine (180 μL, 1.0 mmol) in CH$_2$Cl$_2$ (1 mL). The reaction was stirred overnight and washed with saturated NaHCO$_3$. The aqueous phase was extracted with CH$_2$Cl$_2$ and the extracts were washed with brine, dried, and concentrated. Purification of the residue by preparative TLC with 10:1 CH$_2$Cl$_2$:MeOH gave the free base (83 mg, 0.16 mmol) as a yellow oil. A solution of the free base in CH$_2$Cl$_2$ was treated with 1 N HCl in Et$_2$O (0.3 mL, 0.3 mmol) and concentrated to give the product (86 mg, 32%) as a yellow solid: mp 90.3–95° C.; MS m/z 530 (M+H)$^+$.

Example 25

Preparation of (±)-trans-3-[4-(4-chlorobenzyl) piperidin-1-yl]-4-[3-(3,4,5-trimethoxyphenyl)-ureido]-pyrrolidine-1-sulfonic acid amide hydrochloride

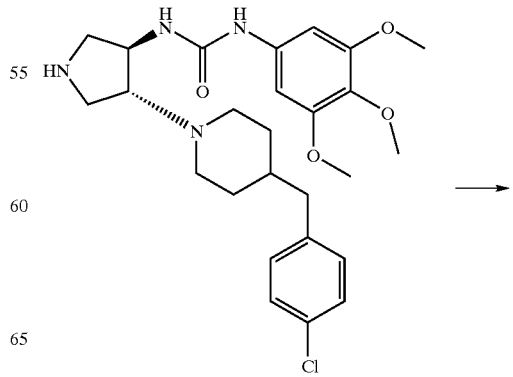

-continued

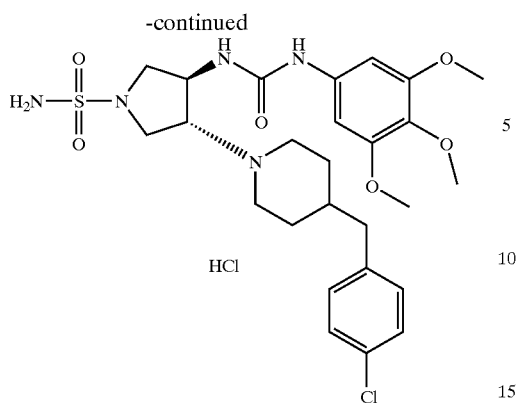

HCl

A solution of chlorosulfonyl isocyanate (23 μL, 0.26 mmol) in CH$_2$Cl$_2$ (1 mL) was treated with t-BuOH (21 μL, 0.22 mmol), stirred at room temperature for 1 hour, and treated with a solution of (±)-trans-1-{4-[4-(4-chlorobenzyl) piperidin-1-yl]-pyrrolidin-3-yl}-3-(3,4,5-trimethoxyphenyl) urea (110 mg, 0.22 mmol) and pyridine (19 μL, 0.24 mmol) in CH$_2$Cl$_2$ (1 mL). The reaction was stirred at room temperature for 2 d during which additional chlorosulfonyl isocyanate (46 μL, 0.52 mmol) and t-BuOH (42 μL, 0.44 mmol) was added, and partitioned between CH$_2$Cl$_2$ and saturated NaHCO$_3$. The aqueous phase was extracted with CH$_2$Cl$_2$ and the extracts were dried and concentrated. Purification of the residue by preparative TLC with 10:0.95:0.05 CH$_2$Cl$_2$:MeOH:NH$_4$OH gave 55 mg of a yellow solid.

A solution of the solid in 10% HCl/MeOH (20 mL) was stirred at room temperature overnight. The MeOH was evaporated and the residue was partitioned between CH$_2$Cl$_2$ and saturated NaHCO$_3$. The aqueous phase was extracted with CH$_2$Cl$_2$ and the extracts were dried (MgSO$_4$) and concentrated. Purification of the residue by preparative TLC with 5:0.95:0.05 CH$_2$Cl$_2$:MeOH:NH$_4$OH gave the free base as a yellow solid. A solution of the free base in CH$_2$Cl$_2$ was treated with 1 N HCl in Et$_2$O (0.1 mL, 0.1 mmol) and concentrated to give the product (20 mg, 48%) as a tan solid: mp 155.7–160.0° C.; IR 3404 (br), 1686, 1607, 1554, 1507 cm$^{-1}$; $^1$H NMR [(CD$_3$)$_2$SO] δ 1.48–1.77 (m, 5H), 2.54 (m, 2H), 3.00–3.83 (m, 18H), 4.60 (m, 1H), 6.73 (s, 2H), 6.85 (m, 1H), 7.11 (br s, 2H), 7.21 (m, 2H), 7.35 (m, 2H), 8.76 (s, 1H), 10.41 (s, 1H); MS m/z 582 (M+H)$^+$. Anal. (C$_{26}$H$_{37}$Cl$_2$N$_5$O$_6$S.1.1H$_2$O) C, H, N.

Example 26

Preparation of (±)-trans-N-{2-[4-(4-chlorobenzyl) piperidin-1-yl]-cyclobutyl}-4-methanesulfonyl-benzamide hydrochloride

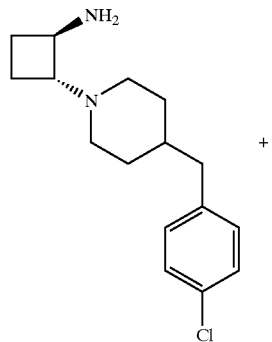

+

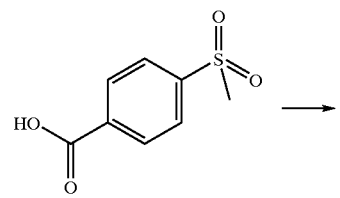

→

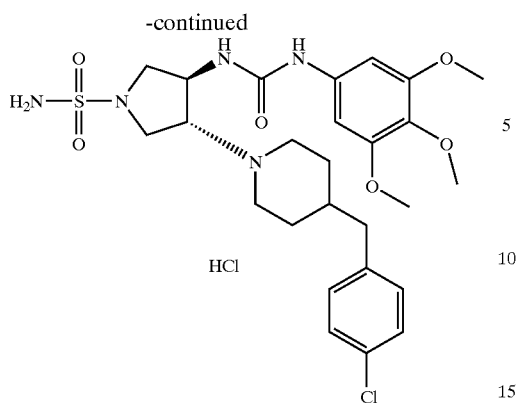

HCl

Following General Procedure F, a solution of (±)-trans-2-[4-(4-chlorobenzyl)piperidin-1-yl]-cyclobutylamine (130 mg, 80% pure, ~0.38 mmol) and 4-methanesulfonyl-benzoic acid (115 mg, 0.575 mmol) in CH$_2$Cl$_2$ (1 mL) at 0° C. was treated successively with 1-hydroxybenzotriazole hydrate (HOBt) (13 mg, 0.10 mmol) and 1-[3-(dimethylamino) propyl]-3-ethylcarbodiimide hydrochloride (DEC) (138 mg, 0.719 mmol), allowed to warm to room temperature slowly, stirred for 3 d, and partitioned between CH$_2$Cl$_2$ and saturated NaHCO$_3$. The aqueous phase was extracted with CH$_2$Cl$_2$ and the extracts were dried and concentrated. Purification of the residue by preparative TLC with 90:9.5:0.5 CH$_2$Cl$_2$:MeOH:NH$_4$OH gave the free base (118 mg, 0.26 mmol) as a white solid. A solution of the free base (93 mg, 0.20 mmol) in CH$_2$Cl$_2$ was treated with 1 N HCl in Et$_2$O (0.5 mL, 0.5 mmol) and concentrated to give the product (90 mg, 21% from (±)-2-[4-(4-chlorobenzyl)-piperidin-1-yl]-cyclobutanone O-methyl-oxime) as a tan powder: mp 173.2–184.1° C.; IR 1657 cm$^{-1}$; $^1$H NMR [(CD$_3$)$_2$SO] δ 1.45–2.20 (m, 9H), 2.52 (m, 2H), 2.65–2.80 (m, 2H), 3.20–3.45 (m, 5H), 3.68–3.79 (m, 1H), 4.79–4.92 (m, 1H), 7.21 (m, 2H), 7.34 (m, 2H), 8.00–8.19 (m, 4H), 9.38 (d, J=8.3 Hz, 1H), 11.04–11.30 (m, 1H); $^{13}$C NMR [(CD$_3$)$_2$SO] δ 17.86, 21.23, 28.00, 34.70, 40.50, 43.21, 46.54, 48.69, 49.15, 64.74, 126.90, 128.07, 128.34, 130.60, 130.78, 138.20, 138.35, 143.08, 164.24; MS m/z 461 (M+H)$^+$. Anal. (C$_{24}$H$_{30}$Cl$_2$N$_2$O$_3$S.0.4CH$_2$Cl$_2$) C, H, N.

Example 27

Preparation of (±)-trans-1-{4-[4-(4-chlorobenzyl)piperidin-1-yl]-1.1-dioxo-tetrahydro-1λ$^6$-thiophen-3-yl}-3-(3,4,5-trimethoxyphenyl)urea hydrochloride

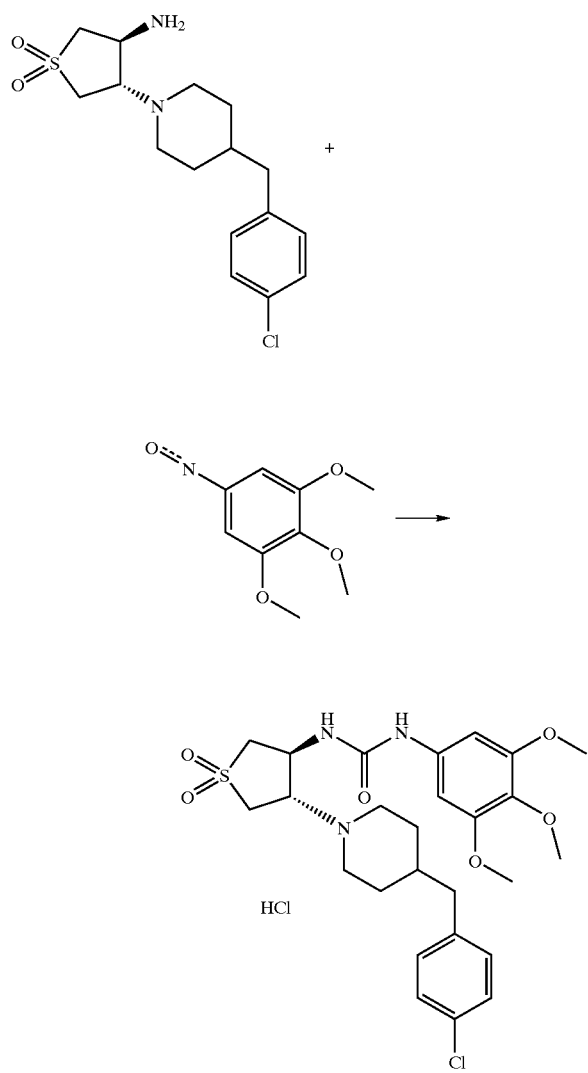

Following General Procedure C, (±)-trans-4-[4-(4-chlorobenzyl)piperidin-1-yl]-1.1-dioxo-tetrahydro-1λ$^6$-thiophen-3-ylamine (60 mg, 0.18 mmol) and 5-isocyanato-1,2,3-trimethoxybenzene (44 mg, 0.21 mmol) were coupled in CH$_2$Cl$_2$ (1.5 mL) at 0° C. for 1 h. Purification of the crude product by preparative TLC with 90:9.5:0.5 CH$_2$Cl$_2$:MeOH:NH$_4$OH and a subsequent preparative TLC with EtOAc gave the free base (55 mg, 0.10 mmol) as yellow solid. A solution of the free base in CH$_2$Cl$_2$ was treated with 1 N HCl in Et$_2$O (0.3 mL, 0.3 mmol) and concentrated to give the product (59 mg, 57%) as a yellow solid: mp 162.0–166.0° C.; IR 3377 (br), 2935, 1690, 1606, 1556, 1506 cm$^{-1}$; $^1$H NMR [(CD$_3$)$_2$SO] δ 1.48 (m, 2H), 1.78 (m, 3H), 2.56 (d, J=6.5 Hz, 2H), 2.89 (m, 2H), 3.21–3.60 (m, 6H), 3.64 (s, 3H), 3.74 (s, 6H), 3.99 (m, 1H), 4.78 (m, 1H), 6.74 (s, 2H), 7.19 (m, 2H), 7.31 (m, 2H); MS m/z 552 (M+H)$^+$. Anal. (C$_{27}$H$_{37}$Cl$_2$N$_3$O.0.4H$_2$O) C, H, N.

Step A: Preparation of (±)-trans-{4-[4-(4-chlorobenzyl)piperidin-1-yl]-1.1-dioxo-tetrahydro-1λ$^6$-thiophen-3-yl}-carbamic acid ethyl ester

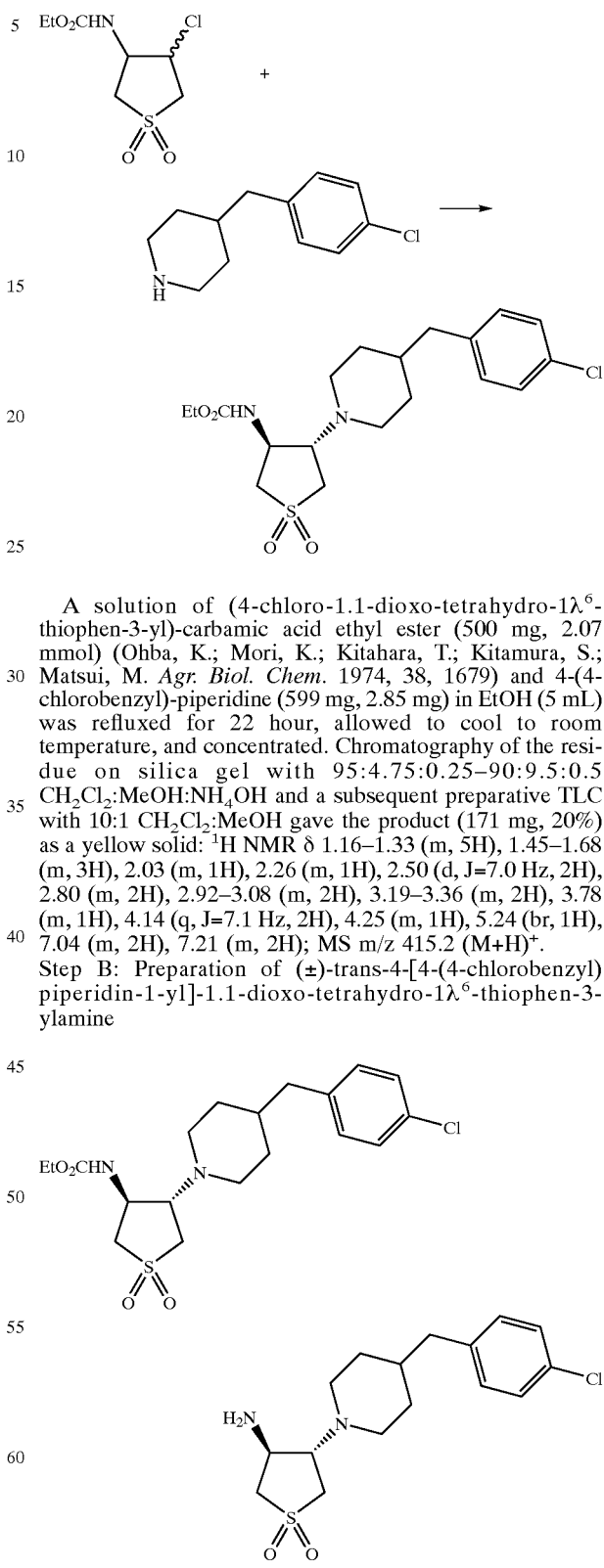

A solution of (4-chloro-1.1-dioxo-tetrahydro-1λ$^6$-thiophen-3-yl)-carbamic acid ethyl ester (500 mg, 2.07 mmol) (Ohba, K.; Mori, K.; Kitahara, T.; Kitamura, S.; Matsui, M. *Agr. Biol. Chem.* 1974, 38, 1679) and 4-(4-chlorobenzyl)-piperidine (599 mg, 2.85 mg) in EtOH (5 mL) was refluxed for 22 hour, allowed to cool to room temperature, and concentrated. Chromatography of the residue on silica gel with 95:4.75:0.25–90:9.5:0.5 CH$_2$Cl$_2$:MeOH:NH$_4$OH and a subsequent preparative TLC with 10:1 CH$_2$Cl$_2$:MeOH gave the product (171 mg, 20%) as a yellow solid: $^1$H NMR δ 1.16–1.33 (m, 5H), 1.45–1.68 (m, 3H), 2.03 (m, 1H), 2.26 (m, 1H), 2.50 (d, J=7.0 Hz, 2H), 2.80 (m, 2H), 2.92–3.08 (m, 2H), 3.19–3.36 (m, 2H), 3.78 (m, 1H), 4.14 (q, J=7.1 Hz, 2H), 4.25 (m, 1H), 5.24 (br, 1H), 7.04 (m, 2H), 7.21 (m, 2H); MS m/z 415.2 (M+H)$^+$.

Step B: Preparation of (±)-trans-4-[4-(4-chlorobenzyl)piperidin-1-yl]-1.1-dioxo-tetrahydro-1λ$^6$-thiophen-3-ylamine A solution of (±)-trans-{4-[4-(4-chlorobenzyl)piperidin-1-yl]-1.1-dioxo-tetrahydro-1λ$^6$-thiophen-3-yl}-carbamic acid ethyl ester (170 mg, 0.41 mmol) in 48% aqueous HBr (3 mL) was refluxed for 16 hour, allowed to cool to room temperature, and poured onto a mixture of ice and granular $Na_2CO_3$. The reaction mixture was completely neutralized and extracted with $CH_2Cl_2$ and the extracts were washed with brine, dried and concentrated. Purification of the residue by preparative TLC with 100:9.5:0.5 $CH_2Cl_2$:MeOH:$NH_4OH$ gave the product (60 mg, 43%) as a yellow solid: $^1H$ NMR δ 1.26 (m, 2H), 1.49 (m, 1H), 1.66 (m, 4H), 2.00 (m, 1H), 2.29 (m, 1H), 2.50 (d, J=7.0 Hz, 2H), 2.77–2.91 (m, 3H), 3.00–3.22 (m, 3H), 3.44 (m, 1H), 3.65 (m, 1H), 7.05 (m, 2H), 7.26 (m, 2H); MS m/z 343.1 $(M+H)^+$.

Example 28

Preparation of (±)-trans-3-{3-[4-(4-chlorobenzyl)piperidin-1-yl]-4-[3-(3,4,5-trimethoxyphenyl)-ureido]-pyrrolidin-1-yl}-3-oxo-proponic acid

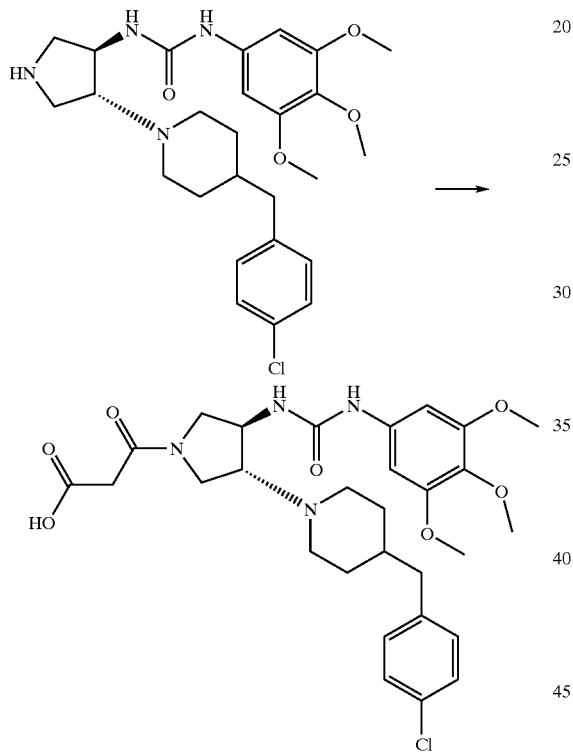

A solution of (±)-trans-1-{4-[4-(4-chlorobenzyl)piperidin-1-yl]-pyrrolidin-3-yl}-3-(3,4,5-trimethoxyphenyl)urea (82 mg, 0.16 mmol) in $CH_2Cl_2$ (3 mL) at 0° C. was treated successively with $Et_3N$ (27 μL, 0.20 mmol) and methyl malonyl chloride (19 μL, 0.18 mmol) and allowed to warm to room temperature slowly. The reaction was stirred for 19 hour, during which additional $Et_3N$ (27 μL, 0.20 mmol) and methyl malonyl chloride (19 μL, 0.18 mmol) was added, and partitioned between $CH_2Cl_2$ and saturated $NaHCO_3$. The aqueous phase was extracted with $CH_2Cl_2$ and the extracts were dried and concentrated to give 87 mg of ester as a yellow solid which was used directly in the next step: $^1H$ NMR δ 1.08–1.61 (m, 5H), 2.03–2.48 (m, 4H), 2.74–3.93 (m, 21H), 4.50 (m, 1H), 5.82 (m, 1H), 6.70 (s, 2H), 7.02 (m, 2H), 7.25 (m, 2H), 7.49 (br s, 1H); MS m/z 603.2 $(M+H)^+$.

A solution of the ester in 5% KOH/MeOH (6 mL) was stirred at room temperature overnight. The MeOH was evaporated, the residue was treated carefully with 1 N HCl until the pH~7 and extracted with $CH_2Cl_2$, and extracts were dried and concentrated. Purification of the residue by preparative TLC with 95:5 MeOH:$NH_4OH$ and a subsequent preparative TLC with 4:0.95:0.05 $CH_2Cl_2$:MeOH:$NH_4OH$ gave the product (40 mg, 42%) as a yellow solid: mp 184.0–184.9° C.; IR 3377, 2924, 1607, 1554, 1506 $cm^{-1}$; $^1H$ NMR [$(CD_3)_2SO$] δ 1.15–1.49 (m, 5H), 2.15 (m, 2H), 2.50 (m, 2H), 3.00–3.71 (m, 18H), 4.62 (m, 1H), 6.80 (s, 2H), 7.13 (m, 3H), 7.25 (m, 2H), 8.87 (m, 1H); MS m/z 589 $(M+H)^+$.

Example 29

Preparation of (±)-trans-1-{2-[4-(4-chlorobenzyl)piperidin-1-yl]-cyclobutyl}-3-(3,4,5-trimethoxyphenyl)urea hydrochloride

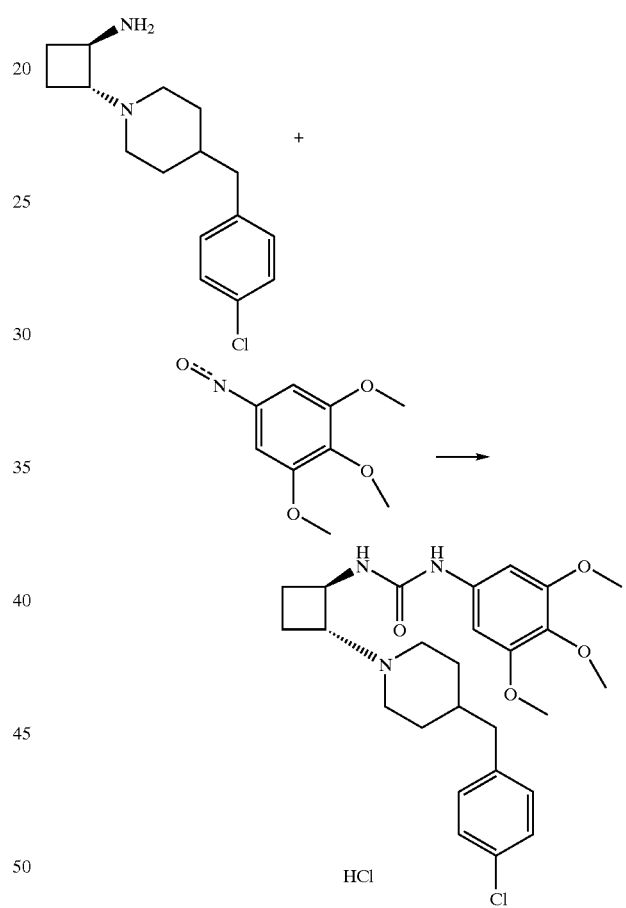

A solution of (±)-trans-2-[4-(4-chlorobenzyl)piperidin-1-yl]-cyclobutylamine (130 mg, 80% pure, ~0.38 mmol) in $CH_2Cl_2$ (1 mL) at 0° C. was treated with 5-isocyanato-1,2,3-trimethoxybenzene (110 mg, 0.53 mmol). The reaction was stirred at 0° C. for 2 hour, during which additional 5-isocyanato-1,2,3-trimethoxybenzene (25 mg, 0.12 mmol) was added, and partitioned between $CH_2Cl_2$ and saturated $NaHCO_3$. The aqueous phase was extracted with $CH_2Cl_2$ and the extracts were dried and concentrated. Chromatography of the residue with 1:1 hexanes:EtOAc to 100% EtOAc followed by 95:4.75:0.25–50:47.5:2.5 $CH_2Cl_2$:MeOH:$NH_4OH$ gave the free base (138 mg, 0.28 mmol) as a glassy solid. A solution of the free base (74 mg, 0.15 mmol) in $CH_2Cl_2$ was treated with 1 N HCl in $Et_2O$ (0.5 mL, 0.5 mmol) and concentrated to give the product (76 mg, 25% from (±)-2-[4-(4-chlorobenzyl)-piperidin-1-yl]-cyclobutanone O-methyl-oxime) as a yellow powder: mp 127.4–128.2° C.; IR 1691, 1607, 1555, 1507 cm$^{-1}$; $^1$H NMR [(CD$_3$)$_2$SO, 77° C.] δ 1.45–1.85 (m, 6H), 1.93–2.20 (m, 3H), 2.54 (d, J=6.7 Hz, 2H), 2.65–2.80 (m, 2H), 3.07 (br s, 0.5H), 3.28 (m, 1H), 3.47–3.62 (m, 1.5H), 3.62 (s, 3H), 3.72 (s, 6H), 4.45–4.58 (m, 1H), 6.75 (m, 2H), 6.90–7.03 (m, 1H), 7.19 (m, 2H), 7.31 (m, 2H), 8.67 (br s, 0.8H), 8.76 (br s, 0.2H), 10.70–11.00 (m, 1H); MS m/z 488 (M+H)$^+$. Anal. (C$_{26}$H$_{34}$Cl$_2$N$_3$O$_4$.0.65H$_2$O) C, H, N.

Example 30

Preparation of (±)-cis-N-{2-[4-(4-chlorobenzyl) piperidin-1-yl]-cyclobutyl}-4-methanesulfonyl-benzamide hydrochloride

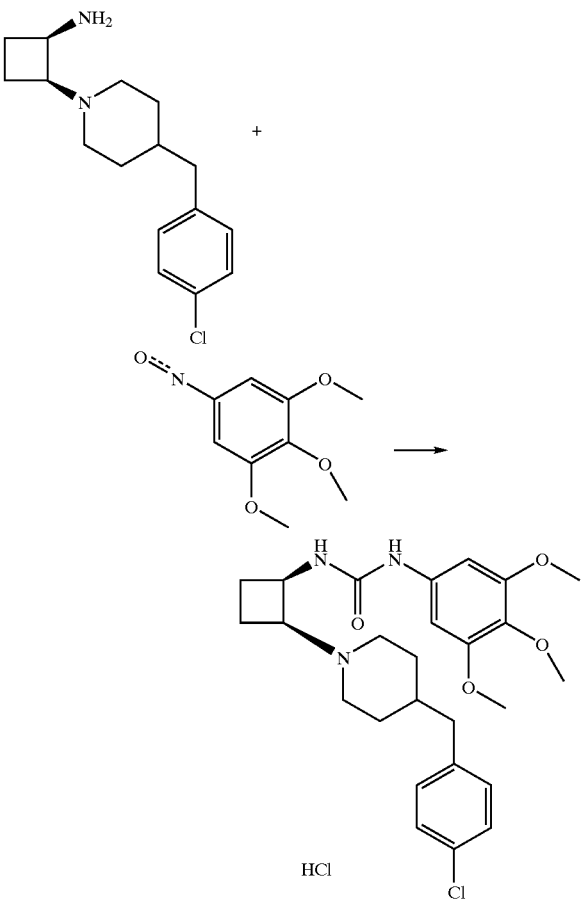

Following General Procedure F, (±)-cis-2-[4-(4-chlorobenzyl)piperidin-1-yl]-cyclobutylamine (100 mg, 90% pure, 0.33 mmol) and 4-methanesulfonyl-benzoic acid (88 mg, 0.44 mmol) were coupled in CH$_2$Cl$_2$ (3 mL) using HOBt (25 mg, 0.18 mmol) and DEC (106 mg, 0.55 mmol) at 0° C. for 3.5 h. Purification of the crude product by preparative TLC with 10:0.95:0.05 CH$_2$Cl$_2$:MeOH:NH$_4$OH gave the free base (102 mg, 0.22 mmol) as a colorless oil. A solution of the free base (82 mg, 0.18 mmol) in CH$_2$Cl$_2$ was treated with 1 N HCl in Et$_2$O (0.5 mL, 0.5 mmol) and concentrated to give the product (83 mg, 64%) as a white solid: mp 130.0–132.5° C.; IR 3438, 2924, 1662, 1541 cm$^{-1}$; MS m/z 461 (M+H)$^+$. Anal. (C$_{24}$H$_{30}$Cl$_2$N$_2$O$_3$S.0.35H$_2$O) C, H, N.

Example 31

Preparation of (±)-cis-1-{2-[4-(4-chlorobenzyl) piperidin-1-yl]-cyclobutyl}-3-(3,4,5-trimethoxyphenyl)urea hydrochloride

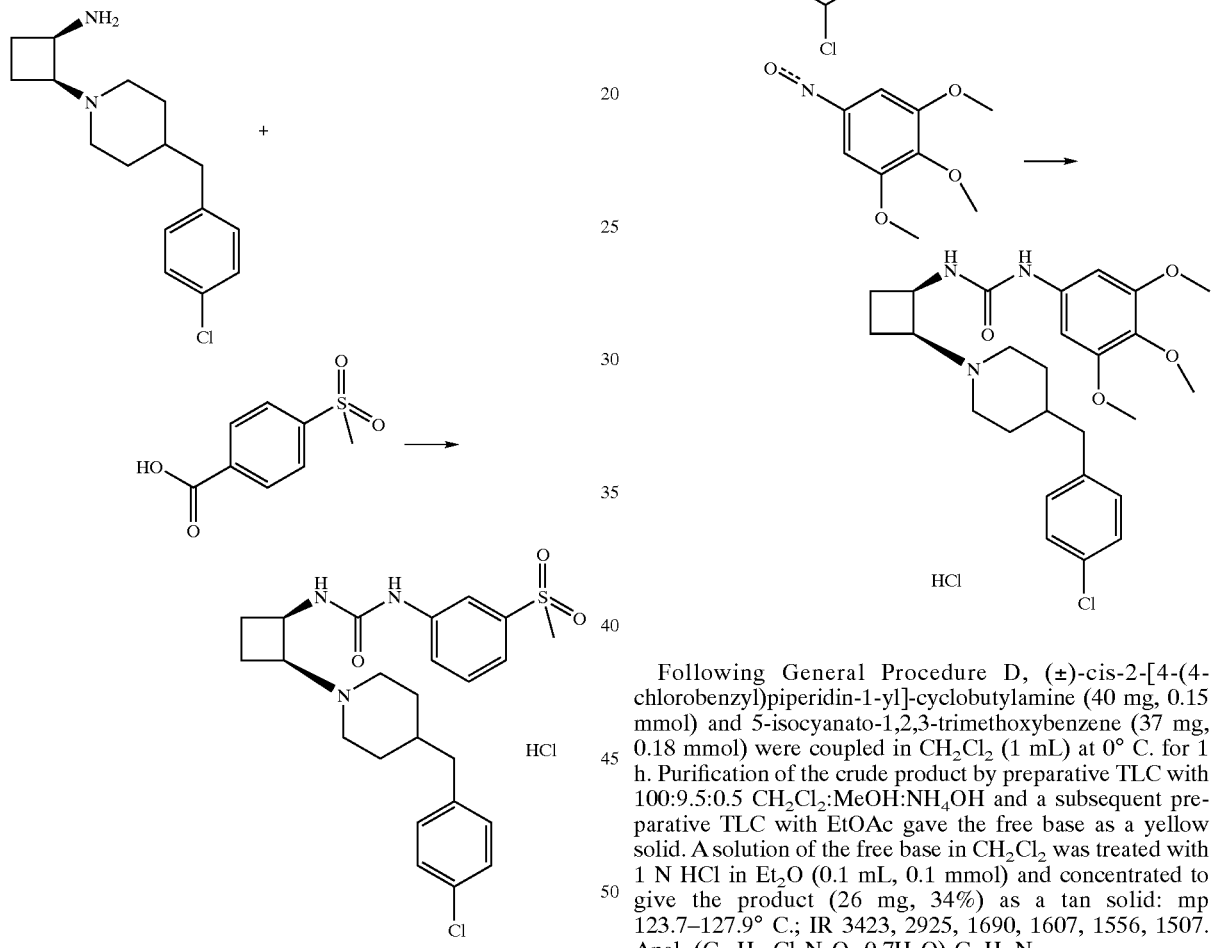

Following General Procedure D, (±)-cis-2-[4-(4-chlorobenzyl)piperidin-1-yl]-cyclobutylamine (40 mg, 0.15 mmol) and 5-isocyanato-1,2,3-trimethoxybenzene (37 mg, 0.18 mmol) were coupled in CH$_2$Cl$_2$ (1 mL) at 0° C. for 1 h. Purification of the crude product by preparative TLC with 100:9.5:0.5 CH$_2$Cl$_2$:MeOH:NH$_4$OH and a subsequent preparative TLC with EtOAc gave the free base as a yellow solid. A solution of the free base in CH$_2$Cl$_2$ was treated with 1 N HCl in Et$_2$O (0.1 mL, 0.1 mmol) and concentrated to give the product (26 mg, 34%) as a tan solid: mp 123.7–127.9° C.; IR 3423, 2925, 1690, 1607, 1556, 1507. Anal. (C$_{26}$H$_{35}$Cl$_2$N$_3$O$_4$.0.7H$_2$O) C, H, N.

Example 32

The Following Compound was Prepared Using General Procedure C, with the Appropriate Amine and Isocyanate (±)-trans-1-{2-[4-(4-Chlorobenzyl)piperidin-1-yl]-cyclopentyl}-3-(3,4,5-trimethoxy-phenyl)urea.

Example 33

The Following Compounds were Prepared Using General Procedure E, with the Appropriate Amine and Carboxylic Acid (±)-trans-N-{2-[4-(4-Chlorobenzyl)piperidin-1-yl] cyclohexyl}-2-[5-(3,4-dimethoxy-phenyl)-pyrimidin-2-ylsulfanyl]acetamide; and (±)-trans-N-{2-[4-(4-Chlorobenzyl)piperidin-1-yl]cyclopentyl}-2-[5-(3,4-dimethoxy-phenyl)-pyrimidin-2-ylsulfanyl]acetamide.

Example 34

The Following Compounds were Prepared Following General Procedure F, Using the Appropriate Amine and Carboxylic Acid (±)-cis-N-{2-[4-(4-Chlorobenzyl)piperidin-1-yl]cyclopentyl}-2-[5-(3,4-dimethoxy-phenyl)-pyrimidin-2-ylsulfanyl]acetamide hydrochloride;

(±)-cis-N-{2-[4-(4-Chlorobenzyl)piperidin-1-yl]cyclohexyl}-2-[5-(3,4-dimethoxy-phenyl)-pyrimidin-2-ylsulfanyl]acetamide hydrochloride; and (±)-trans-N-{2-[4-(4-Chlorobenzyl)piperidin-1-yl]cyclobutyl}-2-[5-(3,4-dimethoxy-phenyl)-pyrimidin-2-ylsulfanyl]acetamide hydrochloride.

Example 35

The Following Compounds were Prepared Following General Procedure G, Using the Appropriate Amine and Sulfonyl Chloride (±)-trans-4-Chloro-N-{2-[4-(4-chlorobenzyl)piperidin-1-yl]-cyclopentyl}-benzenesulfonamide;

(±)-trans-N-{2-[4-(4-Chlorobenzyl)piperidin-1-yl]-cyclopentyl}-3-fluoro-benzenesulfonamide;

(±)-trans-N-{2-[4-(4-Chlorobenzyl)piperidin-1-yl]-cyclopentyl}-4-ethyl-benzenesulfonamide;

(±)-trans-N-{2-[4-(4-Chlorobenzyl)piperidin-1-yl]-cyclopentyl}-3-methoxy-benzenesulfonamide;

(±)-trans-N-{2-[4-(4-Chlorobenzyl)piperidin-1-yl]-cyclopentyl}-2,4-difluoro-benzenesulfonamide;

(±)-trans-N-{2-[4-(4-Chlorobenzyl)piperidin-1-yl]-cyclopentyl}-3-trifluoromethyl-benzenesulfonamide;

(±)-trans-N-{2-[4-(4-Chlorobenzyl)piperidin-1-yl]-cyclopentyl}-4-methyl-benzenesulfonamide;

(±)-trans-N-{2-[4-(4-Chlorobenzyl)piperidin-1-yl]-cyclopentyl}-4-fluoro-benzenesulfonamide;

(±)-trans-N-{2-[4-(4-Chlorobenzyl)piperidin-1-yl]-cyclopentyl}-2-fluoro-benzenesulfonamide;

(±)-trans-2-Chloro-N-{2-[4-(4-chlorobenzyl)piperidin-1-yl]-cyclopentyl}-benzenesulfonamide;

(±)-trans-4-Acetyl-N-{2-[4-(4-chlorobenzyl)piperidin-1-yl]-cyclopentyl}-benzenesulfonamide;

(±)-trans-N-{2-[4-(4-Chlorobenzyl)piperidin-1-yl]-cyclopentyl}-4-nitro-benzenesulfonamide;

(±)-trans-N-{2-[4-(4-Chlorobenzyl)piperidin-1-yl]-cyclopentyl}-3-nitro-benzenesulfonamide;

(±)-trans-3-Chloro-N-{2-[4-(4-chlorobenzyl)piperidin-1-yl]-cyclopentyl}-2-methyl-benzenesulfonamide;

(±)-trans-Naphthalene-1-sulfonic acid {2-[4-(4-chlorobenzyl)piperidin-1-yl]-cyclopentyl}-amide;

(±)-trans-2-Chloro-N-{2-[4-(4-chlorobenzyl)piperidin-1-yl]-cyclopentyl}-4-fluoro-benzenesulfonamide;

(±)-trans-N-{2-[4-(4-Chlorobenzyl)piperidin-1-yl]-cyclopentyl}-3,4-dimethoxy-benzenesulfonamide;

(±)-trans-N-{2-[4-(4-Chlorobenzyl)piperidin-1-yl]-cyclopentyl}-2,5-dimethoxy-benzenesulfonamide;

(±)-trans-2,3-Dichloro-N-{2-[4-(4-chlorobenzyl)piperidin-1-yl]-cyclopentyl}-benzenesulfonamide;

(±)-trans-2,4-Dichloro-N-{2-[4-(4-chlorobenzyl)piperidin-1-yl]-cyclopentyl}-benzenesulfonamide;

(±)-trans-3,4-Dichloro-N-{2-[4-(4-chlorobenzyl)piperidin-1-yl]-cyclopentyl}-benzenesulfonamide;

(±)-trans-N-{2-[4-(4-Chlorobenzyl)piperidin-1-yl]-cyclopentyl}-4-methanesulfonyl-benzenesulfonamide;

(±)-trans-4-Bromo-N-{2-[4-(4-chlorobenzyl)piperidin-1-yl]-cyclopentyl}-benzenesulfonamide;

(±)-trans-4-Chloro-N-{2-[4-(4-chlorobenzyl)piperidin-1-yl]-cyclopentyl}-3-nitro-benzenesulfonamide;

(±)-trans-N-{2-[4-(4-Chlorobenzyl)piperidin-1-yl]-cyclopentyl}-2-nitro-benzenesulfonamide; and (±)-trans-N-{2-[4-(4-Chlorobenzyl)piperidin-1-yl]-cyclopentyl}-2-nitro-4-trifluoromethyl-benzenesulfonamide.

Example 36

The Following Compounds were Prepared Following General Procedure H, Using the Appropriate Amine and Acid Chloride (±)-trans-4-Chloro-N-{2-[4-(4-chlorobenzyl)piperidin-1-yl]-cyclopentyl}-benzamide;

(±)-trans-N-{2-[4-(4-Chlorobenzyl)piperidin-1-yl]-cyclopentyl}-benzamide;

(±)-trans-N-{2-[4-(4-Chlorobenzyl)piperidin-1-yl]-cyclopentyl}-2-fluoro-benzamide;

(±)-trans-2-Chloro-N-{2-[4-(4-chlorobenzyl)piperidin-1-yl]-cyclopentyl}-benzamide;

(±)-trans-3-Chloro-N-{2-[4-(4-chlorobenzyl)piperidin-1-yl]-cyclopentyl}-benzamide;

(±)-trans-N-{2-[4-(4-Chlorobenzyl)piperidin-1-yl]-cyclopentyl}-2-methyl-benzamide;

(±)-trans-N-{2-[4-(4-Chlorobenzyl)piperidin-1-yl]-cyclopentyl}-3-methyl-benzamide;

(±)-trans-N-{2-[4-(4-Chlorobenzyl)piperidin-1-yl]-cyclopentyl}-4-methyl-benzamide;

(±)-trans-N-{2-[4-(4-Chlorobenzyl)piperidin-1-yl]-cyclopentyl}-3-methoxy-benzamide;

(±)-trans-N-{2-[4-(4-Chlorobenzyl)piperidin-1-yl]-cyclopentyl}-2-trifluoromethyl-benzamide;

(±)-trans-N-{2-[4-(4-Chlorobenzyl)piperidin-1-yl]-cyclopentyl}-2-methoxy-benzamide;

(±)-trans-N-{2-[4-(4-Chlorobenzyl)piperidin-1-yl]-cyclopentyl}-4-fluoro-benzamide;

(±)-trans-3-Bromo-N-{2-[4-(4-chlorobenzyl)piperidin-1-yl]-cyclopentyl}-benzamide;

(±)-trans-2,4-Dichloro-N-{2-[4-(4-chlorobenzyl)piperidin-1-yl]-cyclopentyl}-benzamide;

(±)-trans-N-{2-[4-(4-Chlorobenzyl)piperidin-1-yl]-cyclopentyl}-4-trifluoromethyl-benzamide;

(±)-trans-N-{2-[4-(4-Chlorobenzyl)piperidin-1-yl]-cyclopentyl}-3-trifluoromethyl-benzamide;

(±)-trans-N-{2-[4-(4-Chlorobenzyl)piperidin-1-yl]-cyclopentyl}-3,5-bis-trifluoromethyl-benzamide;

(±)-trans-4-tert-Butyl-N-{2-[4-(4-chlorobenzyl)piperidin-1-yl]-cyclopentyl}-benzamide;

(±)-trans-N-{2-[4-(4-Chlorobenzyl)piperidin-1-yl]-cyclopentyl}-4-ethoxy-benzamide;

(±)-trans-N-{2-[4-(4-Chlorobenzyl)piperidin-1-yl]-cyclopentyl}-3-cyano-benzamide;

(±)-trans-N-{2-[4-(4-Chlorobenzyl)piperidin-1-yl]-cyclopentyl}-4-cyano-benzamide;

(±)-trans-N-{2-[4-(4-Chlorobenzyl)piperidin-1-yl]-cyclopentyl}-4-methoxy-benzamide;

(±)-trans-N-{2-[4-(4-Chlorobenzyl)piperidin-1-yl]-cyclopentyl}-3-nitro-benzamide;

(±)-trans-N-{2-[4-(4-Chlorobenzyl)piperidin-1-yl]-cyclopentyl}-4-nitro-benzamide;

(±)-trans-N-{2-[4-(4-Chlorobenzyl)piperidin-1-yl]-cyclopentyl}-3,5-dimethoxy-benzamide;

(±)-trans-3,4-Dichloro-N-{2-[4-(4-chlorobenzyl)piperidin-1-yl]-cyclopentyl}-benzamide;

(±)-trans-4-Bromo-N-{2-[4-(4-chlorobenzyl)piperidin-1-yl]-cyclopentyl}-benzamide; and (±)-trans-N-{2-[4-(4-Chlorobenzyl)piperidin-1-yl]-cyclopentyl}-4-iodo-benzamide.

Example 37

The Following Compounds were Prepared Following General Procedure I, Using the Appropriate Amine and Carboxylic Acid (±)-trans-N-{2-[4-(4-Chlorobenzyl)piperidin-1-yl]-cyclopentyl}-4-isopropyl-benzamide;

(±)-trans-N-{2-[4-(4-Chlorobenzyl)piperidin-1-yl]-cyclopentyl}-isophthalamic acid methyl ester;

(±)-trans-N-{2-[4-(4-Chlorobenzyl)piperidin-1-yl]-cyclopentyl}-4-methanesulfonyl-benzamide;

(±)-trans-3-Acetyl-N-{2-[4-(4-chlorobenzyl)piperidin-1-yl]-cyclopentyl}-benzamide;

(±)-trans-N-{2-[4-(4-Chlorobenzyl)piperidin-1-yl]-cyclopentyl}-2-o-tolyl-acetamide;

(±)-trans-N-{2-[4-(4-Chlorobenzyl)piperidin-1-yl]-cyclopentyl}-2-m-tolyl-acetamide;

(±)-trans-N-{2-[4-(4-Chlorobenzyl)piperidin-1-yl]-cyclopentyl}-2-p-tolyl-acetamide;

(±)-trans-N-{2-[4-(4-Chlorobenzyl)piperidin-1-yl]-cyclopentyl}-2-(4-fluoro-phenyl)-acetamide;

(±)-trans-N-{2-[4-(4-Chlorobenzyl)piperidin-1-yl]-cyclopentyl}-2-(3-methoxy-phenyl)-acetamide;

(±)-trans-N-{2-[4-(4-Chlorobenzyl)piperidin-1-yl]-cyclopentyl}-2-(4-methoxy-phenyl)-acetamide;

(±)-trans-N-{2-[4-(4-Chlorobenzyl)piperidin-1-yl]-cyclopentyl}-2-(3-chloro-phenyl)-acetamide;

(±)-trans-N-{2-[4-(4-Chlorobenzyl)piperidin-1-yl]-cyclopentyl}-2-(4-chloro-phenyl)-acetamide;

(±)-trans-5-Methyl-1H-indole-2-carboxylic acid {2-[4-(4-chlorobenzyl)piperidin-1-yl]-cyclopentyl}-amide;

(±)-trans-5-Fluoro-1H-indole-2-carboxylic acid {2-[4-(4-chlorobenzyl)piperidin-1-yl]-cyclopentyl}-amide;

(±)-trans-2-(3-Bromo-phenyl)-N-{2-[4-(4-chlorobenzyl)piperidin-1-yl]-cyclopentyl}-acetamide;

(±)-trans-N-{2-[4-(4-Chlorobenzyl)piperidin-1-yl]-cyclopentyl}-2-(3,4,5-trimethoxy-phenyl)-acetamide;

(±)-trans-1H-Indole-2-carboxylic acid {2-[4-(4-chlorobenzyl)piperidin-1-yl]-cyclopentyl}-amide;

(±)-trans-5-Methoxy-1H-indole-2-carboxylic acid {2-[4-(4-chlorobenzyl)piperidin-1-yl]-cyclopentyl}-amide; and (±)-trans-5-Chloro-1H-indole-2-carboxylic acid {2-[4-(4-chlorobenzyl)piperidin-1-yl]-cyclopentyl}-amide.

Example 38

The Following Compounds were Prepared Following General Procedure J, Using the Appropriate Amine and Isocyanate (±)-trans-1-{2-[4-(4-Chlorobenzyl)piperidin-1-yl]-cyclopentyl}-3-(4-chloro-phenyl)urea;

(±)-trans-1-{2-[4-(4-Chlorobenzyl)piperidin-1-yl]-cyclopentyl}-3-(4-fluoro-phenyl)urea;

(±)-trans-1-{2-[4-(4-Chlorobenzyl)piperidin-1-yl]-cyclopentyl}-3-o-tolyl-urea;

(±)-trans-1-{2-[4-(4-Chlorobenzyl)piperidin-1-yl]-cyclopentyl}-3-(2-chloro-phenyl)urea;

(±)-trans-1-{2-[4-(4-Chlorobenzyl)piperidin-1-yl]-cyclopentyl}-3-(3-chloro-phenyl)urea;

(±)-trans-1-(3-Bromo-phenyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-p-tolyl-urea;

(±)-trans-1-{2-[4-(4-Chlorobenzyl)piperidin-1-yl]-cyclopentyl}-3-m-tolyl-urea;

(±)-trans-1-{2-[4-(4-Chlorobenzyl)piperidin-1-yl]-cyclopentyl}-3-(4-methoxy-phenyl)urea;

(±)-trans-1-{2-[4-(4-Chlorobenzyl)piperidin-1-yl]-cyclopentyl}-3-(3-methoxy-phenyl)urea;

(±)-trans-1-{2-[4-(4-Chlorobenzyl)piperidin-1-yl]-cyclopentyl}-3-(2-methoxy-phenyl)urea;

(±)-trans-1-{2-[4-(4-Chlorobenzyl)piperidin-1-yl]-cyclopentyl}-3-cyclohexyl-urea;

(±)-trans-1-{2-[4-(4-Chlorobenzyl)piperidin-1-yl]-cyclopentyl}-3-(3-trifluoromethyl-phenyl)urea;

(±)-trans-1-{2-[4-(4-Chlorobenzyl)piperidin-1-yl]-cyclopentyl}-3-(4-trifluoromethyl-phenyl)urea;

(±)-trans-1-{2-[4-(4-Chlorobenzyl)piperidin-1-yl]-cyclopentyl}-3-(4-ethoxy-phenyl)urea;

(±)-trans-1-{2-[4-(4-Chlorobenzyl)piperidin-1-yl]-cyclopentyl}-3-(4-isopropyl-phenyl)urea;

(±)-trans-1-{2-[4-(4-Chlorobenzyl)piperidin-1-yl]-cyclopentyl}-3-(4-cyano-phenyl)urea;

(±)-trans-1-(3-Acetyl-phenyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(3-nitro-phenyl)urea;

(±)-trans-1-{2-[4-(4-Chlorobenzyl)piperidin-1-yl]-cyclopentyl}-3-(4-nitro-phenyl)urea;

(±)-trans-2-(3-{2-[4-(4-Chlorobenzyl)piperidin-1-yl]-cyclopentyl}-ureido)-benzoic acid methyl ester;

(±)-trans-1-{2-[4-(4-Chlorobenzyl)piperidin-1-yl]-cyclopentyl}-3-(3,5-dimethoxy-phenyl)urea;

(±)-trans-1-{2-[4-(4-Chlorobenzyl)piperidin-1-yl]-cyclopentyl}-3-(2,4-dichloro-phenyl)urea;

(±)-trans-1-{2-[4-(4-Chlorobenzyl)piperidin-1-yl]-cyclopentyl}-3-(3,5-dichloro-phenyl)urea;

(±)-trans-1-{2-[4-(4-Chlorobenzyl)piperidin-1-yl]-cyclopentyl}-3-(3,4-dichloro-phenyl)urea;

(±)-trans-1-(4-Bromo-phenyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(2-fluoro-phenyl)urea;

(±)-trans-1-{2-[4-(4-Chlorobenzyl)piperidin-1-yl]-cyclopentyl}-3-(3-fluoro-phenyl)urea;

(±)-trans-1-{2-[4-(4-Chlorobenzyl)piperidin-1-yl]-cyclopentyl}-3-(2,4-difluoro-phenyl)urea;

(±)-trans-1-{2-[4-(4-Chlorobenzyl)piperidin-1-yl]-cyclopentyl}-3-(2,3-dichloro-phenyl)urea;

(±)-trans-1-{2-[4-(4-Chlorobenzyl)piperidin-1-yl]-cyclopentyl}-3-(4-ethyl-phenyl)urea;

(±)-trans-1-{2-[4-(4-Chlorobenzyl)piperidin-1-yl]-cyclopentyl}-3-naphthalen-1-yl-urea;

(±)-trans-1-(3,5-Bis-trifluoromethyl-phenyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(2-nitro-phenyl)urea; and (±)-trans-1-{2-[4-(4-Chlorobenzyl)piperidin-1-yl]-cyclopentyl}-3-(4-iodo-phenyl)urea.

Example 39

The Following Compounds were Prepared Following General Procedure K, Using the Appropriate Amine and Isocyanate (±)-trans-1-(4-Acetyl-phenyl)-3-{2-[4-(4-chlorobenzyl)piperidin-1-yl]-cyclopentyl}-urea;(±)-trans-1-{2-[4-(4-Chlorobenzyl)piperidin-1-yl]-cyclopentyl}-3-phenyl-urea;

(±)-trans-1-Benzyl-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(3-chloro-2-methyl-phenyl)urea;

(±)-trans-1-{2-[4-(4-Chlorobenzyl)piperidin-1-yl]-cyclopentyl}-3-phenethyl-urea;

(±)-trans-1-{2-[4-(4-Chlorobenzyl)piperidin-1-yl]-cyclopentyl}-3-phenethyl-urea;

(±)-trans-1-{2-[4-(4-Chlorobenzyl)piperidin-1-yl]-cyclopentyl}-3-(2,5-dimethyl-phenyl)urea;

(±)-trans-1-{(1R,2R)-2-[4-(4-Chlorobenzyl)piperidin-1-yl]-cyclopentyl}-3-((S)-1-phenyl-ethyl)urea;

(±)-trans-1-{2-[4-(4-Chlorobenzyl)piperidin-1-yl]-cyclopentyl}-3-(3,4-dimethoxy-phenyl)urea;

(±)-trans-1-{2-[4-(4-Chlorobenzyl)piperidin-1-yl]-cyclopentyl}-3-(2-trifluoromethoxy-phenyl)urea;

(±)-trans-1-{2-[4-(4-Chlorobenzyl)piperidin-1-yl]-cyclopentyl}-3-(4-trifluoromethoxy-phenyl)urea;

(±)-trans-1-{2-[4-(4-Chlorobenzyl)piperidin-1-yl]-cyclopentyl}-3-(2-trifluoromethyl-phenyl)urea;

(±)-trans-1-(4-tert-Butyl-phenyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(2-thiophen-2-yl-ethyl)urea;

(±)-trans-1-{2-[4-(4-Chlorobenzyl)piperidin-1-yl]-cyclopentyl}-3-(4-methyl-benzyl)urea;

(±)-trans-1-{2-[4-(4-Chlorobenzyl)piperidin-1-yl]-cyclopentyl}-3-(4-chloro-3-nitro-phenyl)urea;

(±)-trans-1-{2-[4-(4-Chlorobenzyl)piperidin-1-yl]-cyclopentyl}-3-(4-fluoro-benzyl)urea;

(±)-trans-1-{2-[4-(4-Chlorobenzyl)piperidin-1-yl]-cyclopentyl}-3-(2-methyl-benzyl)urea;

(±)-trans-1-{2-[4-(4-Chlorobenzyl)piperidin-1-yl]-cyclopentyl}-3-(3-methyl-benzyl)urea;

(±)-trans-1-(2-Chlorobenzyl)-3-{2-[4-(4-chlorobenzyl)piperidin-1-yl]-cyclopentyl}-urea;

(±)-trans-1-{2-[4-(4-Chlorobenzyl)piperidin-1-yl]-cyclopentyl}-3-(4-methoxy-benzyl)urea; and (±)-trans-1-{2-[4-(4-Chlorobenzyl)piperidin-1-yl]-cyclopentyl}-3-(3,4-dichlorobenzyl)urea.

Example 40

The Following Compounds were Prepared Following General Procedure L, Using the Appropriate Aniline and Phoxime Resin (±)-trans-1-{2-[4-(4-Chlorobenzyl)piperidin-1-yl]-cyclopentyl}-3-(3-ethoxy-phenyl)urea;

(±)-trans-1-{2-[4-(4-Chlorobenzyl)piperidin-1-yl]-cyclopentyl}-3-naphthalen-2-yl-urea;

(±)-trans-1-{2-[4-(4-Chlorobenzyl)piperidin-1-yl]-cyclopentyl}-3-isoquinolin-3-yl-urea;

(±)-trans-1-{2-[4-(4-Chlorobenzyl)piperidin-1-yl]-cyclopentyl}-3-(2-methylquinolin-6-yl)urea;

(±)-trans-1-{2-[4-(4-Chlorobenzyl)piperidin-1-yl]-cyclopentyl}-3-(3-methylamino-phenyl)urea;

(±)-trans-1-{2-[4-(4-Chlorobenzyl)piperidin-1-yl]-cyclopentyl}-3-quinolin-3-yl-urea;

(±)-trans-1-{2-[4-(4-Chlorobenzyl)piperidin-1-yl]-cyclopentyl}-3-quinolin-2-yl-urea;

(±)-trans-1-{2-[4-(4-Chlorobenzyl)piperidin-1-yl]-cyclopentyl}-3-(5-hydroxy-naphthalen-2-yl)urea;

(±)-trans-1-{2-[4-(4-Chlorobenzyl)piperidin-1-yl]-cyclopentyl}-3-(8-hydroxy-quinolin-2-yl)urea; and (±)-trans-1-{2-[4-(4-Chlorobenzyl)piperidin-1-yl]-cyclopentyl}-3-(5,7-dimethyl-[1,8]naphthyridin-2-yl)urea.

Example 41

The Following Compounds were Prepared Following General Procedure M, Using the Appropriate Aniline (±)-trans-1-{2-[4-(4-Chlorobenzyl)piperidin-1-yl]-cyclopentyl}-3-quinolin-6-yl-urea;

(±)-trans-N-[3-(3-{2-[4-(4-Chlorobenzyl)piperidin-1-yl]-cyclopentyl}-ureido)-phenyl]-acetamide;

(±)-trans-1-{2-[4-(4-Chlorobenzyl)piperidin-1-yl]-cyclopentyl}-3-(2,3,4-trimethoxy-phenyl)urea; and (±)-trans-1-{2-[4-(4-Chlorobenzyl)piperidin-1-yl]-cyclopentyl}-3-(3-methanesulfonyl-phenyl)urea.

Example 42

The Following Compounds were Prepared Following General Procedure N, Using the Appropriate Thioisocyanate (±)-trans-1-{2-[4-(4-Chlorobenzyl)piperidin-1-yl]-cyclopentyl}-3-o-tolyl-thiourea;

(±)-trans-1-{2-[4-(4-Chlorobenzyl)piperidin-1-yl]-cyclopentyl}-3-m-tolyl-thiourea;

1-{2-[4-(4-Chlorobenzyl)piperidin-1-yl]-cyclopentyl}-3-(3-chloro-phenyl)-thiourea;

(±)-trans-1-{2-[4-(4-Chlorobenzyl)piperidin-1-yl]-cyclopentyl}-3-p-tolyl-thiourea;

(±)-trans-1-{2-[4-(4-Chlorobenzyl)piperidin-1-yl]-cyclopentyl}-3-(4-fluoro-phenyl)-thiourea; and (±)-trans-1-{2-[4-(4-Chlorobenzyl)piperidin-1-yl]-cyclopentyl}-3-(4-methoxy-phenyl)-thiourea.

Example 43

The Following Compounds were Prepared Following General Procedure O, Using the Appropriate Succinimide (±)-trans-{2-[4-(4-Chlorobenzyl)piperidin-1-yl]-cyclopentyl}-carbamic acid 4-fluoro-benzyl ester;

(±)-trans-{2-[4-(4-Chlorobenzyl)piperidin-1-yl]-cyclopentyl}-carbamic acid 3-chlorobenzyl ester;

(±)-trans-{2-[4-(4-Chlorobenzyl)piperdin-1-yl]-cyclopentyl}-carbamic acid 4-chlorobenzyl ester;

(±)-trans-{2-[4-(4-Chlorobenzyl)piperidin-1-yl]-cyclopentyl}-carbamic acid 2-chlorobenzyl ester;

(±)-trans-{2-[4-(4-Chlorobenzyl)piperidin-1-yl]-cyclopentyl}-carbamic acid 3-nitro-benzyl ester;

(±)-trans-{2-[4-(4-Chlorobenzyl)piperidin-1-yl]-cyclopentyl}-carbamic acid 3-trifluoromethyl-benzyl ester;

(±)-trans-{2-[4-(4-Chlorobenzyl)piperidin-1-yl]-cyclopentyl}-carbamic acid 3,4-dichlorobenzyl ester;

(±)-trans-{2-[4-(4-Chlorobenzyl)piperidin-1-yl]-cyclopentyl}-carbamic acid 3,5-dichlorobenzyl ester;

(±)-trans-{2-[4-(4-Chlorobenzyl)piperidin-1-yl]-cyclopentyl}-carbamic acid benzyl ester; and (±)-trans-{2-[4-(4-Chlorobenzyl)piperidin-1-yl]-cyclopentyl}-carbamic acid 4-nitro-benzyl ester.

(±)-trans-{2-[4-(4-Chlorobenzyl)piperidin-1-yl]-cyclopentyl}-carbamic acid benzyl ester (±)-trans-{2-[4-(4-Chlorobenzyl)piperidin-1-yl]-cyclopentyl}-carbamic acid benzyl ester (±)-trans-{2-[4-(4-Chlorobenzyl)piperidin-1-yl]-cyclopentyl}-carbamic acid benzyl ester

Example 44

Formulation Examples

The following are representative pharmaceutical Formulations containing a compound of Formula (I).

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |

-continued

| Ingredient | Amount |
| --- | --- |
| propyl paraben | 0.05 g |
| granulated sugar | 25.5 g |
| sorbit (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable Formulation.

| Ingredient | Amount |
| --- | --- |
| compound of this invention | 0.2 g |
| sodium acetate buffer solution, | 0.4 M 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal Formulation.

| Ingredient | Amount |
| --- | --- |
| compound of this invention | 10 mg |
| L-.alpha.-phosphatidylcholine | 150 mg |
| tert-butanol | 4 ml |

Freeze dry the sample and lyophilize overnight. Reconstitute the sample with 1 ml 0.9% saline solution. Liposome size can be reduced by sonication.

Example 45

CCR-3 Receptor Binding Assay—In Vitro

The CCR-3 antagonistic activity of the compounds of the invention was determined by their ability to inhibit the binding of $^{125}I$ eotaxin to CCR-3 L1.2 transfectant cells (see Ponath, P. D. et al., J. Exp. Med., Vol. 183, 2437–2448, (1996)).

The assay was performed in Costar 96-well polypropylene round bottom plates. Test compounds were dissolved in DMSO and then diluted with binding buffer (50 mM HEPES, 1 mM CaCl.sub.2, 5 mM $MgCl_2$, 0.5% bovine serum albumin (BSA), 0.02% sodium azide, pH 7.24) such that the final DMSO concentration was 2%. 25 μl of the test solution or only buffer with DMSO (control samples) was added to each well, followed by the addition of 25 μl of $^{125}I$-eotaxin (100 pmol) (NEX314, New England Nuclear, Boston, Mass.) and $1.5 \times 10^5$ of the CCR-3 L1.2 transfected cells in 25 μl binding buffer. The final reaction volume was 75 μl.

After incubating the reaction mixture for 1 hour at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 minutes. 25 μl/well of Microscint-20® scintillation fluid (Packard) was added and the radioactivity retained on the filters was determined by using the Packard TopCount®.

Compounds of this invention were active in this assay.

| Compound Number from Table 1 | IC50 ($\mu$M) |
|---|---|
| 1 | 0.5574 |
| 2 | 0.0185 |
| 3 | 1.1438 |
| 4 | 0.8644 |
| 5 | 2.6906 |
| 6 | 1.8558 |
| 7 | 1.4841 |
| 8 | 6.0949 |
| 9 | 5.1191 |
| 10 | 0.5122 |

Example 46

Inhibition of Eotaxin Mediated Chemotaxis of CCR-3 L1.2 Transfectant Cells—In Vitro Assay The CCR-3 antagonistic activity of the compounds of this invention can be determined by measuring the inhibition of eotaxin mediated chemotaxis of the CCR-3 L1.2 transfectant cells, using a slight modification of the method described in Ponath, P. D. et al., J. Clin. Invest. 97: 604–612 (1996). The assay is performed in a 24-well chemotaxis plate (Costar Corp., Cambridge, Mass.). CCR-3 L1.2 transfectant cells are grown in culture medium containing RPMI 1640, 10% Hyclone® fetal calf serum, 55 mM 2-mercaptoethanol and Geneticin 418 (0.8 mg/ml). 18–24 hours before the assay, the transfected cells are treated with n-butyric acid at a final concentration of 5 mM/1×10$^6$ cells/ml, isolated and resuspended at 1×10$^7$ cells/ml in assay medium containing equal parts of RPMI 1640 and Medium 199 (M 199) with 0.5% bovine serum albumin.

Human eotaxin suspended in phosphate buffered saline at 1 mg/ml is added to bottom chamber in a final concentration of 100 nm. Transwell culture inserts (Costar Corp., Cambridge, Mass.) having 3 micron pore size are inserted into each well and L1.2 cells (1×10$^6$) are added up to the top chamber in a final volume of 100 μl. Test compounds in DMSO are added both to the top and bottom chambers such that the final DMSO volume is 0.5%. The assay is performed against two sets of controls. The positive control contained cells with no test compound in the top chamber and only eotaxin in the lower chamber. The negative control contains cells with no test compound in the top chamber and neither eotaxin nor test compound in lower chamber. The plate is incubated at 37° C. After 4 hours, the inserts are removed from the chambers and the cells that have migrated to the bottom chamber are counted by pipetting out 500 μl of the cell suspension from the lower chamber to 1.2 ml Cluster tubes (Costar) and counting them on a FACS for 30 seconds.

Example 47

Inhibition of Eotaxin Mediated Chemotaxis of Human Eosinophils—In Vitro Assay

The ability of compounds of the invention to inhibit eotaxin mediated chemotaxis of human eosinophils can be assessed using a slight modification of procedure described in Carr, M. W. et al., Proc. Natl. Acad. Sci. USA, 91: 3652–3656 (1994). Experiments are performed using 24 well chemotaxis plates (Costar Corp., Cambridge, Mass.). Eosinophils are isolated from blood using the procedure described in PCT Application, Publication No. WO 96/22371. The endothelial cells used are the endothelial cell line ECV 304 obtained from European Collection of Animal Cell Cultures (Porton Down, Salisbury, U.K.). Endothelial cells are cultured on 6.5 mm diameter Biocoat.R™. Transwell tissue culture inserts (Costar Corp., Cambridge, Mass.) with a 3.0 μM pore size. Culture media for ECV 304 cells consists of M199, 10% Fetal Calf Serum, L-glutamine and antibiotics. Assay media consists of equal parts RPMI 1640 and M199, with 0.5% BSA. 24 hours before the assay 2×10$^5$ ECV 304 cells are plated on each insert of the 24-well chemotaxis plate and incubated at 37° C. 20 nM of eotaxin diluted in assay medium is added to the bottom chamber. The final volume in bottom chamber is 600 μl. The endothelial coated tissue culture inserts are inserted into each well. 10$^6$ eosinophil cells suspended in 100 μl assay buffer are added to the top chamber. Test compounds dissolved in DMSO are added to both top and bottom chambers such that the final DMSO volume in each well was 0.5%. The assay is performed against two sets of controls. The positive control contains cells in the top chamber and eotaxin in the lower chamber. The negative control contains cells in the top chamber and only assay buffer in the lower chamber. The plates are incubated at 37° C. in 5% $CO_2$/95% air for 1–1.5 hours.

The cells that migrate to the bottom chamber are counted using flow cytometry. 500 μl of the cell suspension from the lower chamber are placed in a tube, and relative cell counts are obtained by acquiring events for a set time period of 30 seconds.

Example 48

Inhibition of Eosinophil Influx Into the Lungs of Ovalbumin Sensitized Balb/c Mice by CCR-3 Antagonist—In Vivo Assay The ability of the compounds of the invention to inhibit leukocyte infiltration into the lungs can be determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g are sensitized with OA (10 μg in 0.2 ml aluminum hydroxide solution) intraperitoneally on days 1 and 14. After a week, the mice are divided into ten groups. Test compound or only vehicle (control group) or anti-eotaxin antibody (positive control group) is administered either intraperitoneally, subcutaneously or orally. After 1 hour, the mice are placed in a Plexiglass box and exposed to OA aerosol generated by a PARISTAR.™. nebulizer (PARI, Richmond, Va.) for 20 minutes. Mice which have not been sensitized or challenged are included as a negative control. After 24 or 72 hours, the mice are anesthetized (urethane, approx. 1 g/kg, i.p.), a tracheal cannula (PE 60 tubing) is inserted and the lungs are lavaged four times with 0.3 ml PBS. The BAL fluid is transferred into plastic tubes and kept on ice. Total leukocytes in a 20 μl aliquot of the BAL fluid is determined by Coulter Counter.™. (Coulter, Miami, Fla.). Differential leukocyte counts are made on Cytospin.™. preparations which have been stained with a modified Wright's stain (DiffQuick.™.) by light microscopy using standard morphological criteria.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention

What is claimed:

1. A compound of Formula (I):

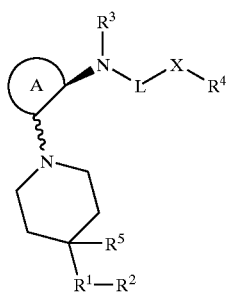

(I)

wherein:
R$^1$ is (C$_1$–C$_2$)alkylene;
R$^2$ is optionally substituted phenyl;
R$^3$ is hydrogen, alkyl, acyl, aryl, or arylalkyl;
ring A and the two carbons it is attached to form, a ring selected from cyclopropyl, cyclobutyl, or cyclopentyl and cyclohexyl;
L is —C(=O)—, —C(=S)—, —SO$_2$—, —C(=O)N(R$_a$)—, —C(=S)N(R$_a$)—, —SO$_2$N(R$_a$)—, —C(=O)O—, —C(=S)O—, —S(=O)$_2$O—;
    where R$_a$ is hydrogen, alkyl, acyl, aryl, arylalkyl, alkoxycarbonyl, or benzyloxycarbonyl;
X is absent, —(CR'R")O—, —(CR'R")S—, —(CR'R")NR$_b$— or alkylene;
    where R' and R" are independently hydrogen or alkyl, and R$_b$ is hydrogen or alkyl;
R$^4$ is optionally substituted aryl or optionally substituted heteroaryl; and
R$^5$ is hydrogen or alkyl;
provided that when R$^1$ is —CH$_2$—, R$^2$ is phenyl, R$^3$ is hydrogen, R$^5$ is hydrogen, A is phenyl, L is —C(=O)NH— and X is absent, then R$^4$ is not 2,5-difluorophenyl; or individual isomers, racemic and non-racemic mixtures of isomers, and pharmaceutically acceptable salts thereof.

2. The compound of claim 1, which is a compound of Formula (II):

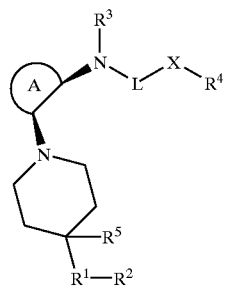

(II)

wherein R$^1$–R$^5$, A, L, and X have any of the values described in claim 1.

3. The compound of claim 1, which is a compound of Formula (III):

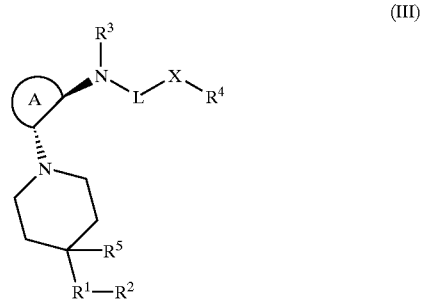

(III)

wherein R$^1$–R$^5$, A, L, and X have any of the values described in claim 1.

4. The compound of any one of claims 1–3 wherein R$^1$ is methylene.

5. The compound of any one of claims 1–3 wherein R$^2$ is 4-chlorophenyl or 3,4-dichlorophenyl.

6. The compound of any one of claims 1–3 wherein R$^3$ is hydrogen.

7. The compound of any one of claims 1–3 wherein L is —C(=O)—, —SO$_2$—, —C(=O)N(R$_a$), —C(=S)N(R$_a$)—, or —C(=O)O—.

8. The compound of any one of claims 1–3 wherein L is —C(=O)—.

9. The compound of any one of claims 1–3 wherein L is —C(=O)N(R$_a$)—.

10. The compound of claim 1, which is a compound of Formula (IV):

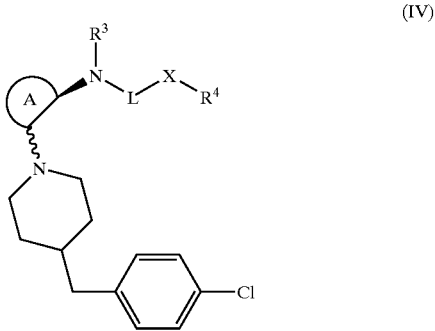

(IV)

wherein R$^3$, R$^4$, A, L, and X have any of the values described in claim 1.

11. The compound of claim 1, which is a compound of Formula (V):

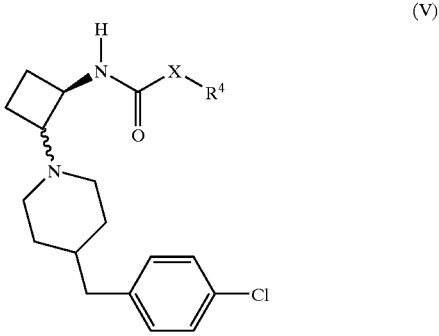

(V)

wherein X and R$^4$ have any of the values defined in claim 1.

12. The compound of claim 1, which is a compound of Formula (VI):

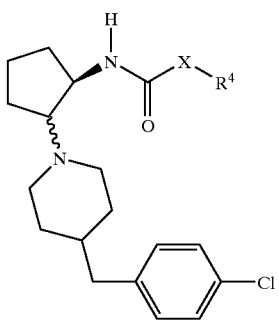

(VI)

wherein X and $R^4$ have any of the values defined in claim 1.

13. The compound of claim 1, which is a compound of Formula (VII):

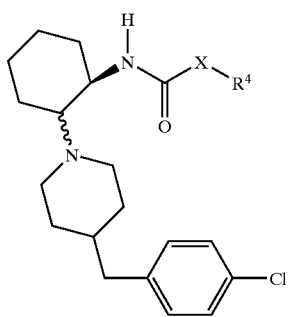

(VII)

wherein X and $R^4$ have any of the values defined in claim 1.

14. The compound of claim 7 wherein X is absent, methylene, 1,2-ethanediyl, 1,3-propanediyl, or 1,4-butanediyl.

15. The compound of claim 14, wherein $R^4$ is optionally substituted aryl.

16. The compound of claim 14, wherein $R^4$ is optionally substituted heteroaryl.

17. The compound of claim 15, wherein $R^4$ is indol-2-yl, 5-methoxyindol-2-yl, 5-chloroindol-2-yl, 2-thienyl, 3-isoquinolyl, 2-methylquinolin-6-yl, 3-quinolyl, 2-quinolyl, 8-hydroxyquinolin-2-yl, 5,7-dimethyl-[1,8]naphthyridin-2-yl, or 6-quinolyl.

18. The compound of claim 15 wherein $R^4$ is 3,4-dichlorophenyl, 3,4,5-trimethoxyphenyl, 4-methanesulfonylphenyl, 3-methanesulfonylphenyl, 4-methoxynaphthalen-2-yl, 5-(3,4-dimethoxyphenyl)pyrimidin-2-yl, phenyl, 3-fluorophenyl, 4-ethylphenyl, 3-methoxyphenyl, 2,4-difluorophenyl, 3-trifluoromethylphenyl, 4-methylphenyl, 4-fluorophenyl, 2-fluorophenyl, 4-carboxamidophenyl, 3-carboxamidophenyl, 4-acetylphenyl, 4-nitrophenyl, 2-methylphenyl, 2-chloro-4-fluorophenyl, 3,4-dimethoxyphenyl, 2,5-dimethoxyphenyl, 2,3-dichlorophenyl, 2,4-dichlorophenyl, 4-bromophenyl, 4-chloro-3-nitrophenyl, 2-nitrophenyl, 2-nitro-4-trifluoromethylphenyl, 4-chlorophenyl, 3-chlorophenyl, 2-chlorophenyl, 3-methylphenyl, 2-trifluoromethylphenyl, 2-methoxyphenyl, 3-bromophenyl, 4-trifluoromethylphenyl, 3-trifluoromethylphenyl, 3,5-bis-trifluoromethylphenyl, 4-tert-butylphenyl, 4-ethoxyphenyl, 3-cyanophenyl, 4-cyanophenyl, 4-methoxyphenyl, 3-nitrophenyl, 3,5-dimethoxyphenyl, 4-iodophenyl, 4-isopropylphenyl, 3-methoxycarbonylphenyl, 3-acetylphenyl, 2-methylphenyl, 2-methoxycarbonylphenyl, 3,5-dichlorophenyl, 1-naphthyl, 3-chloro-2-methylphenyl, 2,5-dimethylphenyl, 3-ethoxyphenyl, 3-methylaminophenyl, 5-hydroxynaphthalen-2yl, 3-(acetylamino)phenyl, or 2,3,4-trimethoxyphenyl.

19. The compound of claim 18 wherein $R^4$ is 3,4,5-trimethoxyphenyl, 4-acetyl-phenyl, 3-carboxamidophenyl, 4-carboxamidophenyl, 3-methanesulfonylphenyl or 4-methanesulfonylphenyl.

20. The compound of claim 8, wherein X is —CH$_2$S— and $R^4$ is 5-(3,4-dimethoxyphenyl)-pyrimidin-2-yl, 5-(3,4-methylenedioxyphenyl)-pyrimidin-2-yl or 5-(4-methoxyphenyl)pyrimidin-2-yl, and a salt thereof.

21. The compound of claim 1, wherein $R^2$ is substituted phenyl.

22. A composition containing a therapeutically effective amount of a compound as described in any one of claims 1–21, or a salt thereof; and an excipient.

23. A method of treatment of a disease in a mammal treatable by administration of a CCR-3 receptor antagonist, comprising administering to the mammal a therapeutically effective amount of a compound of Formula (I) as described in any one of claims 1–13 or 17–20 or a salt thereof, wherein said disease is asthma.

* * * * *